(12) United States Patent
Chaplin et al.

(10) Patent No.: US 8,716,335 B2
(45) Date of Patent: May 6, 2014

(54) SUBSTITUTED BENZOFURANS, BENZOTHIOPHENES, BENZOSELENOPHENES AND INDOLES AND THEIR USE AS TUBULIN POLYMERISATION INHIBITORS

(75) Inventors: Jason Hugh Chaplin, Thornbury (AU); Gurmit Singh Gill, Craigieburn (IN); Damian Wojciech Grobelny, Watsonia North (AU); Bernard Luke Flynn, Vermont (AU); Gabriel Kremmidiotis, Flagstaff Hill (AU)

(73) Assignee: Bionomics Limited (AU)

( * ) Notice: Subject to any disclaimer, the term of this patent is extended or adjusted under 35 U.S.C. 154(b) by 106 days.

(21) Appl. No.: 13/461,213

(22) Filed: May 1, 2012

(65) Prior Publication Data
US 2012/0214770 A1    Aug. 23, 2012

Related U.S. Application Data

(63) Continuation of application No. 12/162,917, filed as application No. PCT/AU2007/000101 on Feb. 2, 2007, now Pat. No. 8,198,466.

(60) Provisional application No. 60/765,337, filed on Feb. 3, 2006.

(51) Int. Cl.
*A61K 31/343* (2006.01)
*C07D 307/80* (2006.01)

(52) U.S. Cl.
CPC .................................. *C07D 307/80* (2013.01)
USPC ............................................. 514/469; 549/471

(58) Field of Classification Search
CPC ....................................................... C07D 307/80
USPC .......................................................... 549/471
See application file for complete search history.

(56) References Cited

U.S. PATENT DOCUMENTS

| | | | |
|---|---|---|---|
| 6,538,038 B1 | 3/2003 | Pero et al. | |
| 2003/0195244 A1 | 10/2003 | Hsieh et al. | |
| 2004/0044059 A1 | 3/2004 | Pinney et al. | |
| 2005/0245489 A1 | 11/2005 | Pinney et al. | |
| 2005/0267108 A1 | 12/2005 | Hsieh et al. | |
| 2006/0148801 A1 | 7/2006 | Hsieh et al. | |
| 2010/0004208 A1 | 1/2010 | Chaplin et al. | |

FOREIGN PATENT DOCUMENTS

| | | |
|---|---|---|
| EP | 0587377 | 3/1994 |
| EP | 0937459 | 8/1999 |
| EP | 1400244 | 3/2004 |
| WO | WO 93/23040 | 11/1993 |
| WO | WO 93/23041 | 11/1993 |
| WO | WO 98/39323 | 9/1998 |
| WO | WO 00/39108 | 7/2000 |
| WO | WO 01/19794 | 3/2001 |
| WO | WO 01/28557 | 4/2001 |
| WO | WO 01/51456 | 7/2001 |
| WO | WO 01/68654 | 9/2001 |
| WO | WO 01/77099 | 10/2001 |
| WO | WO 02/00651 | 1/2002 |
| WO | WO 02/16340 | 2/2002 |
| WO | WO 02/46178 | 6/2002 |
| WO | WO 02/060872 | 8/2002 |
| WO | WO 02/074768 | 9/2002 |
| WO | WO 03/004485 | 1/2003 |
| WO | WO 2004/099171 | 1/2004 |
| WO | WO 2005/113532 | 12/2005 |
| WO | WO 2006/084338 | 8/2006 |
| WO | WO 2007/087684 | 8/2007 |

OTHER PUBLICATIONS

"Cancer," Retrieved from the internet, URL: http://en.wikipedia.org/wiki/Cancer, Retrieved on Jul. 6, 2007, 2 pages.
"Cancer," Retrieved from the internet, URL: http://www.nlm.nih.gov/medlineplus/cancer.html>, Retrieved on Jul. 6, 2007, 10 pages.
Golub et al., "Molecular classification of cancer: class discovery and class prediction by gene expression monitoring," Science, Oct. 1999, 286(5439), 531-537.
Lala et al., "Role of nitric oxide in tumor progression: lessons from experimental tumors," Cancer and Metastasis Reviews, Mar. 1998, 17(1), 91-106.
Astoin, J. et al., "Study of benzofuran. LIX. Orientation of the aroylation of 2-ethylbenzofuran depending on the aroyl chloride used," Journal of Heterocyclic Chemistry, Aug. 1977, 14(5), 861-866.
Astoin, J. et al., "Study of benzofuran. LX. Orientation of the alkaline degradation of 3-aroyl-2-ethylbenzofurans depending on the aroyl group substituent," Journal of Heterocyclic Chemistry, Aug. 1977, 14(5), 867-869.
Baum, J.S. et al., "Diazotransfer Reactions with p-Acetamidobenzenesulfonyl Azide," Synthetic Communication, 1987, 17(14), 1709-1716.
Bishop, B.C. et al, "Synthesis of 3-Hydroxyalkylbenzobfuran Via the Palladium-Catalysed Heteroannulation of Silyl-Protected Alkynols With 2-Iodophenol," Synthesis, 1997, Issue 11, 1315-1320.
Buu-Hoi, N.P. et al., "Spasmolytic ketone derivatives of benzofuran," Comptes rendus hebdomaires des séances de l'Academie des sciences, 1961, 253, 1075-1076.
Chaplin, J.H. et al., "A multi-component coupling approach to benzo[b]furans and indoles," Chemical Communications, Aug. 2001, 17, 1594-1595.
Chemical Abstract corresponding to JP39010344 published Jun. 11, 1964 to Eisai Co., Ltd.
Collini, M.D. et al., "The Solid Phase Synthesis of Tri-Substituted Indoles," Tetrahedron Letters, Nov. 1997, 38(46), 7963-7966.
Davis, P.D. et al., "ZD6126: A Novel Vascular-targeting Agent That Causes Selective Destruction of Tumor Vasculature," Cancer Res., Dec. 2002, 62(24), 7247-7253.
Descamps, M. et al., "The benzofuran series XI. Synthesis of pyrazoles and isoxazoles from 3-oxobenzofurans," Bulletin des Societes Chimiques Belges, 1964, 73(5-6), 459-482.
Flynn, B.L. et al., "A Novel Palladium-Mediated Coupling Approach to 2,3-Disubstituted Benzo[b]thiophenes and Its Application to the Synthesis of Tubulin Binding Agents," Org. Lett., Mar. 2001, 3(5), 651-654.
Flynn, B.L. et al., "One-Pot Synthesis of Benzo{b]furan and Indole Inhibitors of Tubulin Polymerization," J. Med. Chem, Jun. 2002, 45(12), 2670-2673.

(Continued)

*Primary Examiner* — Shawquia Young
(74) *Attorney, Agent, or Firm* — Baker & Hostetler LLP

(57) ABSTRACT

The present invention relates generally to substituted benzofurans, benzothiophenes, and indoles and their use as tubulin polymerization inhibitors.

2 Claims, 3 Drawing Sheets

(56) References Cited

OTHER PUBLICATIONS

Fontana & Pignatti, "Synthesis of Brostallicin (PNU-166196A) Labelled with $^2$H and $^{14}$C", Journal of Label. Compd. Radiopharm., Oct. 2002, 45(11), 899-909.

Gottardo, C. et al., "Palladium-catalyzed carbon-carbon coupling reactions using aryl Grignards," Tetrahedron Letters, Sep. 2002, 43(39), 7091-7094.

Han Y. et al, "Solid Phase Parallel Synthesis of Highly Substituted Thiophene Derivatives and Identification of Novel Phosphodiesterase-4 (PDE-4) Inhibitors," Tetrahedron, Sep. 1999, 55(39), 11669-11685.

Hu, Y. et al., "Palladium-Catalyzed Carbonylative Annulation of o-Alkynylphenols: Syntheses of 2-Substituted -3-aroyl-benzo[b[furans," J. Org. Chem., Apr. 2002, 67(7), 2365-2368.

Johnson, M.G., et al., "Solid Phase Chemistry Approach to the SAR Development of a Novel Class of Active Site-Directed Thrombin Inhibitors," Tetrahedron, Sep. 1999, 55(39), 11641-11642.

Karaseva, M.G. et al., "Synthesis of some benzoylbenzofurans," Zhurnal Vsesoyeznogo Khimicheskogo Obshchestva im. D.I. Mendeleeva, 1967, 12(1), 108-109.

Liou, J-P. et al., "Concise Synthesis and Structure-Activity Relationships of Combretastatin A-4 Analogues, 1-Aroylindoles and 3-Aroylindoles, as Novel Classes of Potent Antitubulin Agents," Journal of Medicinal Chemistry, Aug. 2004, 47(17), 4247-4257.

Patent Abstracts of Japan; Abstract for JP 03-142277 published Jun. 18, 1991 to Fuji Photo Film Co. Ltd.

Patent Abstracts of Japan; Abstract for JP 2002-371076 published Dec. 26, 2002 to Sumitomo Seika Chem Co. Ltd.

Pettit, G. R., et al, "Antineoplastic agents 322. Synthesis of combretastatin A-4 prodrugs," Anticancer Drug Des., Jun. 1995, 10(4), 299-309.

Romagnoli, R. et al., "Synthesis and preliminary biological evaluation of new anti-tubulin agents containing different benzoheterocycles," Bioorg. Med. Chem. Lett., Sep. 2005, 15(18), 4048-4052.

Rustin, J. et al., "Phase I Clinical Trial of Weekly Combretastatin A4 Phosphate: Clinical and Pharmacokinetic Results," J. Clin. Oncol., Aug. 2003, 21(15), 2815-2822.

Thompson, M.J. et al., "Studies on the Two-Phase Nitration of Phenols (part 2)," Tetrahedron, 1990, 46(7), 2661-2674.

Tozer, G.M. et al., "Disrupting Tumour Blood Vessels," Nature Rev., Jun. 2005, 5(6), 423-435.

SUBSTITUTED BENZOFURANS, BENZOTHIOPHENES, BENZOSELENOPHENES AND INDOLES AND THEIR USE AS TUBULIN POLYMERISATION INHIBITORS

CROSS-REFERENCE TO RELATED APPLICATIONS

This application is a continuation of U.S. Ser. No. 12/162,917, filed May 28, 2009 (now allowed) as the United States national stage application of International Application No. PCT/AU2007/000101, filed Feb. 2, 2007, which claims the benefit of U.S. Provisional Application No. 60/765,337, filed Feb. 3, 2006, the entire disclosures of each of which are incorporated herein by reference.

FIELD OF THE INVENTION

The present invention relates generally to chemical compounds and methods for their use and preparation. In particular, the invention relates to chemical compounds which may possess useful therapeutic activity, use of these compounds in methods of therapy and the manufacture of medicaments as well as compositions containing these compounds.

BACKGROUND OF THE INVENTION

Tubulin is an important target in controlling disease states associated with cell proliferation such as cancer and inflammation (eg, psoriasis). Tubulin is composed of a heterodimer of two related proteins called α and β tubulin. Tubulin polymerises to form structures called microtubules. Compounds that inhibit tubulin's ability to polymerise to form microtubules interrupt cell division which is dependent on the formation of microtubules to form mitotic spindles. Examples of such compounds include the Vinca alkaloids such as vincristine and vinblastine.

Furthermore, compounds that inhibit the depolymerisation of microtubules can also prevent cell division since they often disrupt the proper formation of mitotic spindles which must also disassemble in order for cell division to be completed. Interruption of the mitotic process in this manner often induces cell death by an apoptotic mechanism. Examples of compounds which act in this manner include the taxoids such as paclitaxel.

For these antimitotic agents, selectivity for diseased versus non-diseased tissue is based on relative rates of proliferation, where the diseased tissue more rapidly proliferates. Accordingly, diseased tissue is generally more sensitive to the effect of these agents because it is more likely to be in a state of mitosis which is the stage of a cell's life cycle affected by agents that target tubulin. Unfortunately however, a number of normal, healthy tissues also have quite high rates of proliferation (for example hair follicles and the lining of the gastro-intestinal tract) and accordingly, these tissues can be damaged during chemotherapy with these agents.

Tubulin is also a target for treating disease states that are dependent or result from the abnormal formation of blood vessels (neovascularisation) such as in cancerous tumours and in ocular myopathy. In these cases the cytoskeleton of the vascular endothelial cells are disrupted through depolymerisation of microtubules, which results from inhibiting the polymerisation of tubulin to form microtubules. Microtubule length is dependent on the rate of depolymerisation versus polymerisation. Depolymerising microtubules through inhibition of polymerisation leads to a change in endothelial cell morphology, which then causes a blockage or shutdown in blood flow. In the case of cancerous tumours, blood flow to the diseased tissue is stopped, depriving the tumour of oxygen and nutrients leading to necrotic cell death. Neovascular systems are more sensitive to these agents because they are more dependent on microtubule cytoskeletons than normal, healthy, vascular endothelial cells which are also supported by actin based cytoskeletal structures. For a number of tubulin polymerisation inhibitors (TPIs) that target the colchicine binding site of tubulin, the vascular targeting modality can be achieved at a lower in vivo concentration than the antiproliferative modality. In theory though, agents that target the colchicine binding domain of tubulin are potentially dual mode agents (i.e. antimitotic and antivascular).

One of the most potent inhibitors of tubulin polymerisation that binds to the colchicine binding domain of tubulin is the cis-stilbene, combretastatin A4 (CA4) (1). Due to its insolubility CA4 is administered as its prodrug equivalent combretastatin A4 disodium phosphate (CA4P) (2), where the phosphate is rapidly cleaved in vivo. CA4P is currently undergoing phase I and II clinical trials and is the most advanced vascular targeting agent being trialed. In view of some of the draw-backs associated with CA4P, such as, instability (can isomerise to the inactive trans-stilbene), toxicity and rapid clearance, a number of synthetic groups have sought to prepare more stable analogues that could be designed to exhibit an improved therapeutic index and exhibit improved pharmacokinetics. Recently, a number of TPIs have been identified that contain the benzofuran, indole or benzothiophene ring systems (see for example, WO 1998/39323, WO 2001/19794 and WO 2001/68654) or chromene and dihydronapthalene ring systems (see for example, WO 2005/113532, and WO 1998/39323). Such ring systems are quite stable and should over come the stability issues associated with CA4P. Unfortunately, such compounds only exhibit moderate tubulin binding and anti-mitotic activity. Accordingly, there exists a need to identify other compounds which are more stable than CA4 and exhibit satisfactory pharmacological properties and/or activity.

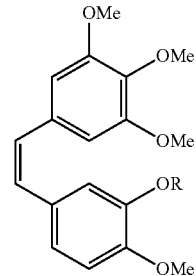

(1) CA4: R = H
(2) CA4P: R = —P(O)O$_2$Na$_2$

The present invention provides compounds of formula (I) and salts thereof;

SUMMARY

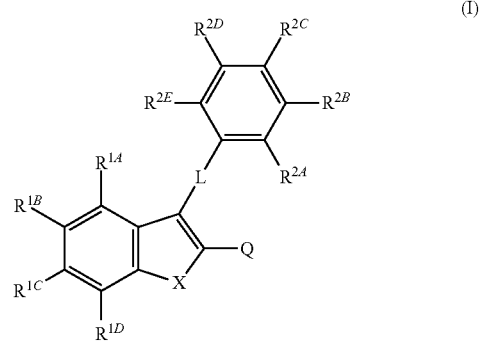

wherein;

X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, SO$_2$, Se, SeO, SeO$_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

The present invention also provides a method for treating a disease state by inhibiting tubulin polymerisation including the step of administering to a patient in need thereof a compound of formula (I) or a pharmaceutically acceptable salt thereof;

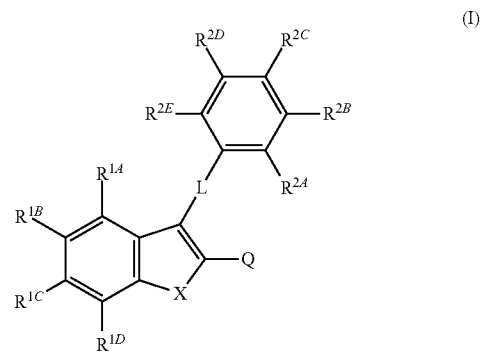

wherein;

X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl.

The present invention also provides the use of a compound of formula (I) or a pharmaceutically acceptable salt thereof:

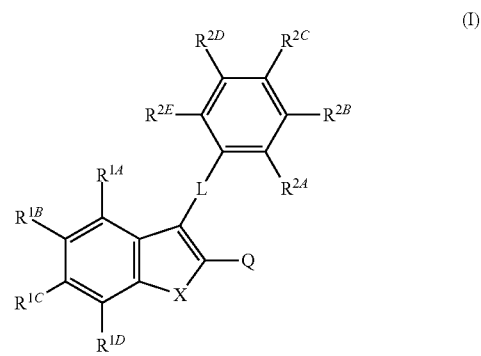

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; or NR' where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl;

in the manufacture of a medicament for the treatment of a disease state by inhibiting tubulin polymerisation.

DESCRIPTION OF THE PREFERRED EMBODIMENTS

Figure 1:
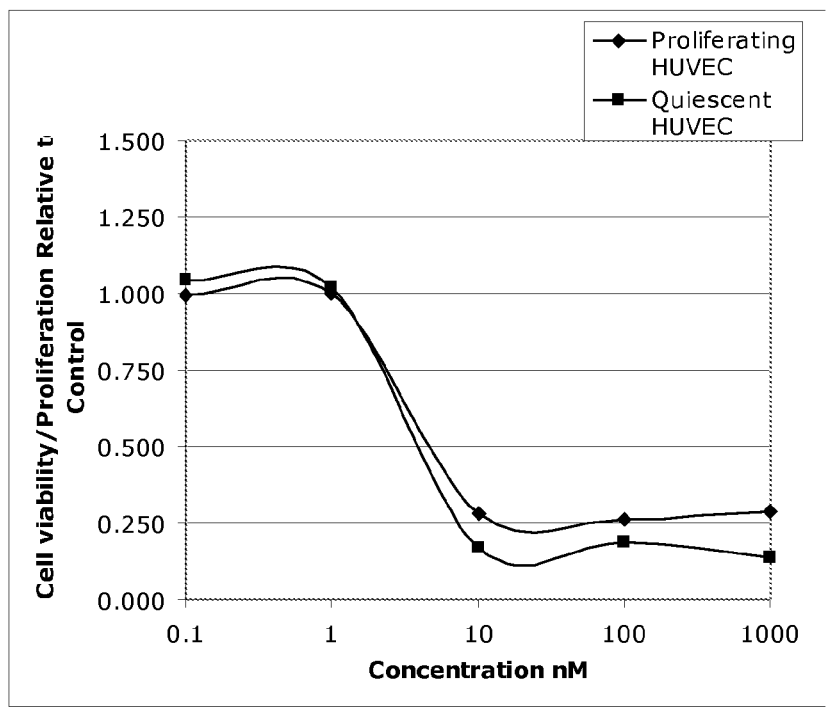
FIG. 1 depicts a graph of cell viability/proliferation relative to control against concentration of CA4(1)(nM) in relation to proliferating and quiescent endothelial cells.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

"Alkyl" refers to monovalent alkyl groups which may be straight chained or branched and preferably have from 1 to 10 carbon atoms or more preferably 1 to 6 carbon atoms, and even more preferably 1 to 3 carbon atoms. Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms, and even more preferably 1 to 3 carbon atoms. Examples of such alkylene groups include methylene (—$CH_2$—), ethylene (—$CH_2CH_2$—), and the propylene isomers (e.g., —$CH_2CH_2CH_2$— and —$CH(CH_3)CH_2$—), and the like.

"Aryl" refers to an unsaturated aromatic carbocyclic group having a single ring (e.g., phenyl) or multiple condensed rings (e.g., naphthyl or anthryl), preferably having from 6 to 14 carbon atoms. Examples of aryl groups include phenyl, naphthyl and the like.

"Arylene" refers to a divalent aryl group wherein the aryl group is as described above.

"Aryloxy" refers to the group aryl-O— wherein the aryl group is as described above.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH═CH$_2$), n-propenyl (—CH$_2$CH═CH$_2$), iso-propenyl (—C(CH$_3$)═CH$_2$), but-2-enyl (—CH$_2$CH═CHCH$_3$), and the like.

"Alkenyloxy" refers to the group alkenyl-O— wherein the alkenyl group is as described above.

"Alkenylene" refers to divalent alkenyl groups preferably having from 2 to 8 carbon atoms and more preferably 2 to 6 carbon atoms. Examples include ethenylene (—CH═CH—), and the propenylene isomers (e.g., —CH$_2$CH═CH— and —C(CH$_3$)═CH—), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—CH$_2$C≡CH), pent-2-ynyl (—CH$_2$C≡CH$_2$—CH$_3$), and the like.

"Alkynyloxy" refers to the group alkynyl-O— wherein the alkynyl groups is as described above.

"Alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Aminoacylamino" refers to the group —NR*C(O)NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Acylamino" refers to the group —NR*C(O)R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Acyloxy" refers to the groups —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O)NR*-alkyl, —OC(O)NR*-aryl, —OC(O)NR*-heteroaryl, and —OC(O)NR*-heterocyclyl where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR*C(O)O-alkyl, —NR*C(O)O-aryl, —NR*C(O)O-heteroaryl, and NR*C(O)O-heterocyclyl where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O-heteroaryl, and —OC(O)O-heterocyclyl where alkyl, cycloalkyl, aryl, heteroaryl, and heterocyclyl are as described herein.

"Acylimino" refers to the groups —C(NR*)—R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR*)—R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR*)—OR* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 8 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

"Cycloalkenyl" refers to cyclic alkenyl groups having a single cyclic ring and at least one point of internal unsaturation, preferably incorporating 4 to 8 carbon atoms. Examples of suitable cycloalkenyl groups include, for instance, cyclobut-2-enyl, cyclopent-3-enyl, cyclohex-4-enyl, cyclooct-3-enyl and the like.

"Halo" or "halogen" refers to fluoro, chloro, bromo and iodo.

"Heteroaryl" refers to a monovalent aromatic heterocyclic group which fulfils the Hückel criteria for aromaticity (i.e. contains $4n+2\pi$ electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (e.g., pyridyl, pyrrolyl or N-oxides thereof or furyl) or multiple condensed rings (e.g., indolizinyl, benzoimidazolyl, coumarinyl, quinolinyl, isoquinolinyl or benzothienyl).

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR*—P(O)(R)(OR*) where R* represents H, alkyl, cycloalkyl, alkenyl, or aryl, R represents OR* or is hydroxy or amino and R*** is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR*—, alkyl-S(O)—NR*—, cycloalkyl-S(O)—NR*—, aryl-S(O)—NR*—, heteroaryl-S(O)—NR*—, and heterocyclyl-S(O)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR*—, alkyl-S(O)$_2$—NR*—, cycloalkyl-S(O)$_2$—NR*—, aryl-S(O)$_2$—NR*—, heteroaryl-S(O)$_2$—NR*—, and heterocyclyl-S(O)$_2$—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR*—, alkylO—S(O)—NR*—, cycloalkylO—S(O)—NR*—, arylO—S(O)—NR*—, heteroarylO—S(O)—NR*—, and heterocyclylO—S(O)—NR*—, where R* is independently hydrogen, alkyl, cycloalkyl, aryl, heteroaryl, and heterocy-clyl and where each of alkyl, cycloalkyl, aryl, heteroaryl and heterocyclyl is as described herein.

"Oxysulfonylamino" refers to groups HO—S(O)$_2$—NR*—, alkylO—S(O)$_2$—NR*—, cycloalkylO—S(O)$_2$—NR*—, arylO—S(O)$_2$—NR*—, heteroarylO—S(O)$_2$—NR*—, and heterocyclylO—S(O)$_2$—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R*R*N—C(S)—, where each R* is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR*—, alkyl-C(S)—NR*—, cycloalkyl-C(S)—NR*—, aryl-C(S)—NR*—, heteroaryl-C(S)—NR*—, and heterocyclyl-C(S)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R*R*N—S(O)—, where each R* is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R*R*N—S(O)$_2$—, where each R* is independently hydrogen, alkyl, cycloalkyl, aryl, heteroaryl, and heterocyclic and where each of alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxy, acyl, alkyl, alkoxy, alkenyl, alkenyloxy, alkynyl, alkynyloxy, amino, aminoacyl, thio, arylalkyl, arylalkoxy, aryl, aryloxy, acylamino, cyano, halogen, nitro, sulfo, phosphono, phosphorylamino, phosphinyl, heteroaryl, heteroaryloxy, heterocyclyl, heterocyclyloxy, oxyacyl, oxime, oxime ether, hydrazone, —NHC(NH)NH$_2$, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di- (substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like, and may also include a bond to a solid support material, (for example, substituted onto a polymer resin).

An optionally substituted amino group may also include amino acid and peptide residues.

In some embodiments $R^{1A}$-$R^{1B}$ and $R^{2A}$-$R^{2E}$ are independently selected from the following groups:

alkyl group, preferably methyl and ethyl;

substituted alkyl group, preferably 1-hydroxyethyl, 1-thioethyl, methoxyiminomethyl, ethoxyiminomethyl, 1-(hydroxyimino)ethyl, 1-(hydroxyimino)propyl, 1-hydrazino ethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;

acyl group, preferably formyl acetyl, propionyl, benzoyl (optionally substituted with methyl, methoxy, halogen, nitro, trifluoromethyl or cyano);

alkoxy group, preferably methoxy and ethoxy;

oxyacyl group, preferably methoxycarbonyl, ethoxycarbonyl, propoxycarbonyl, butyloxycarbonyl, isobutyloxycarbonyl;

acyloxy group, preferably acetoxy and propioxy;

substituted arylalkyl group, preferably 1-hydroxybenzyl, and 1-thiobenzyl;

sulfinyl group, preferably methylsulfinyl, ethylsulfinyl, benzene sulfinyl (optionally substituted with methyl, methoxy, halogen, nitro, trifluoromethane or cyano), methoxysulfinyl, ethoxysulfinyl;

sulfonyl group, preferably methylsulfonyl, ethylsulfonyl, benzenesulfonyl (optionally substituted with methyl, methoxy, halogen, nitro, trifluoromethane or cyano), methoxycarbo, trifluoromethane;

oxyacylamino group, preferably methoxycarbonylamido, and ethoxycarbonyl amido;

oxythioacyl group, preferably methoxythiocarbonyl and ethoxythiocarbonyl;

thioacyloxy group, preferably thionoacetoxy and thionopropionoxy;

sulphinylamino group, preferably methylsulfinylamino, ethylsulfinylamino, and benzenesulfinylamino (optionally substituted with methyl, methoxy, halogen, nitro, trifluoromethane or cyano);

amino group;

substituted amino groups, preferably residues of L-valine, D-valine, L-alanine, D-alanine, aspartic acid, and alanylserine, N-methylamino, and N,N'-dimethylamino;

sulphonylamino group, preferably methylsulfonylamino, ethylsulfonylamino and benzene sulfonylamino (optionally substituted with methyl, methoxy, halogen, nitro, trifluoromethane or cyano);

oxysulfinylamino group, preferably methoxysulfinylamino and ethoxysulfinylamino; oxysulfonylamino group, preferably methoxysulfonylamino and ethoxysulfonylamino;

optionally substituted alkenyl group, preferably, 1-propenyl, vinyl, nitrovinyl, cyano vinyl, or trifluorovinyl and styryl (optionally substituted with methyl, methoxy, halogen, nitro, trifluoromethane or cyano);

alkynyl group, preferably 1-propynyl, ethynyl or trimethylsilylethynyl.

In one embodiment $R^{2D}$, $R^{2C}$, and $R^{2B}$ are methoxy and L is a carbonyl group (C=O).

Accordingly, in this embodiment the compounds of the present invention are represented by formula (Ia)

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

$R^{2A}$ and $R^{2E}$ independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

In another embodiment, $R^{1A}$, $R^{1B}$, $R^{2A}$ and $R^{2E}$ represent H and $R^{1C}$ represents $C_{1-3}$ alkoxy.

Accordingly, in this embodiment the compounds of the present invention are represented by formula (Ib)

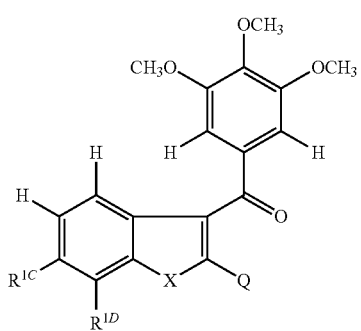

(Ib)

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1C}$ represents $C_{1-3}$ alkoxy;

$R^{1D}$ represents hydroxy or amino;

Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

In a preferred embodiment $R^{1C}$ represents methoxy.

For the compounds represented by formulae I, Ia and Ib, X is preferably selected from O, S and NR. More preferably X is O or NR and most preferably X is O.

Accordingly, in another embodiment the present invention provides novel benzofurans and pharmaceutically acceptable salts thereof of formula II:

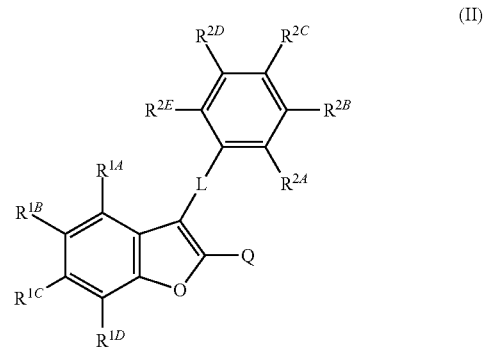

(II)

wherein;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl.

In this embodiment it is preferred that L is a carbonyl group (C=O). Also, preferably at least one of $R^{2D}$, $R^{2C}$ or $R^{2B}$ represents a hydroxy or $C_{1-3}$ alkoxy group. More preferably when X=O, L is a carbonyl group an $R^{2D}$, $R^{2C}$ and $R^{2B}$ represent methoxy. Even more preferably when X=O, L is a carbonyl group, $R^{2D}$, $R^{2C}$, and $R^{2B}$ represent methoxy and $R^{1A}$, $R^{1B}$, $R^{2A}$, $R^{2E}$ are H.

Furthermore, for the compounds of formula (I), (Ia), (Ib) and (II) it is preferred that Q represents H, CN, optionally substituted $C_{2-4}$ alkynyl, optionally substituted $C_{2-6}$ alkenyl, optionally substituted $C_{1-4}$ alkyl, hydroxy, optionally substituted oxyacyl, NR"R", SR" (where each R" is independently H, optionally substituted $C_{1-4}$alkyl, optionally substituted heterocyclyl, optionally substituted heteroaryl), NR'"NR'" (where each R'" is independently H, $C_{1-3}$ alkyl), optionally substituted acylamino, or halogen.

In some embodiments Q is independently selected from the following groups:

H;

CN;

halogen, preferably Br or Cl;

alkyl group, preferably methyl, ethyl, propyl, butyl;

substituted alkyl group, preferably amino, oxyacylaminoalkyl and oxysulphonylaminoalkyl;

optionally substituted alkenyl, preferably ethenyl, 2-alkylethenyl, 2-oxyacylethenyl, 2-aminoacylethenyl;

optionally substituted alkynyl, preferably ethynyl, 2-alkylethynyl;

optionally substituted oxyacyl;

OR", hydroxy, methoxy, ethoxy;

NR"R", preferably $NH_2$, alkylamino, dialkylamino, heteroarylamino, aminoalkylamino, hydroxyalkylamino, alkoxyalkylamino, oxyacylalkylamino, oxyacylaminoalkylamino, guanidinoalkylamino;

SR", preferably alkylthio, aminoalkylthio, heteroarylthio, aminoalkylthio, hydroxyalkylthio, alkoxyalkylthio, oxyacylalkylthio, oxyacylaminoalkylthio, guanidinoalkylthio; hydrazine.

The compounds of the present invention can be prepared by the multicomponent reaction system which has been described in PCT/AU02/00099 (WO 02/060872), the entire contents of which is incorporated herein by reference. In particular the compounds of the present invention can be prepared by the reaction sequence depicted in Scheme 1 below:

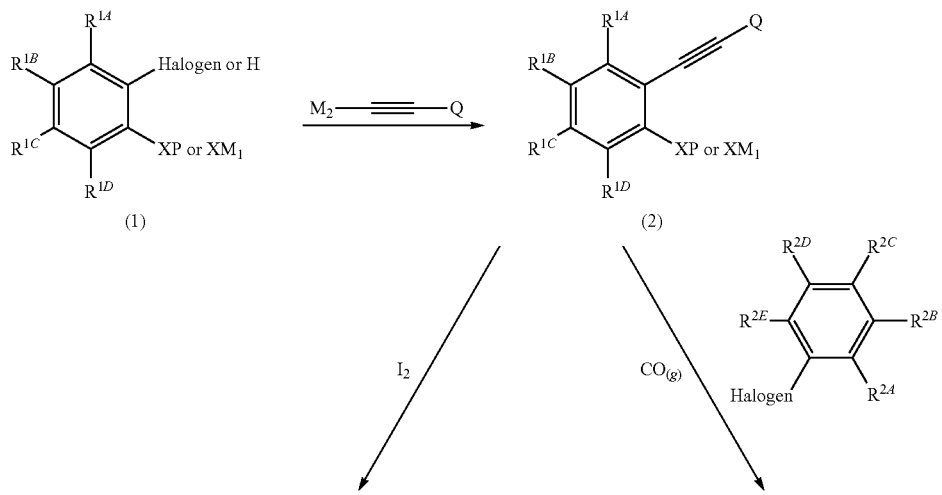

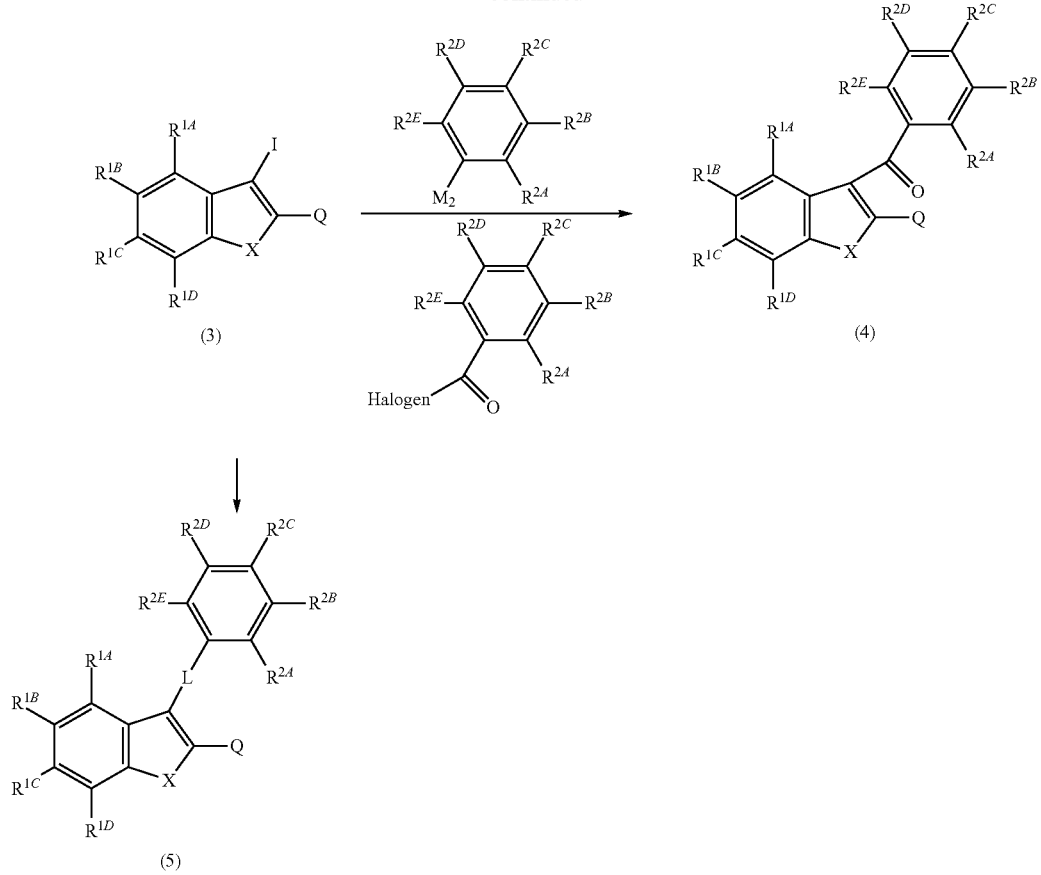

Where Q is for example optionally substituted alkyl, optionally substituted alkenyl, optionally substituted alkynyl, OR'', SR'', NR''R'' or NR'''NR''';

X is S, NR, O or Se, and

L is O, S, Se, or NR'.

As shown above in Scheme 1, the compounds of formula I in which X is NR or O can be derived from reacting together a phenol or protected amine and terminal alkyne respectively. The starting phenol or aniline and terminal alkyne can be coupled together under conditions which allow for heteroannulation to spontaneously occur so as to form the target benzo[b]furan or indole in a "one-pot" synthetic strategy. Thus, the metal based compound required to form (2) (when $XM_1$) should be such that the phenol or protected amine is deprotonated to form the group —$OM_1$ or $NHM_1$.

Suitable $M_1$ are based on Li, Na, K, Mg, Cs and Ba as well as species formed therefrom, for example from Grignard reagents $C_{1-4}$alkyl MgHal (Hal=I, Cl or Br). Suitable metal species include MgCl, MgBr or MgI. Formation of (1) can be effected by treating the corresponding phenol or protected amine with, for example, $Li_2CO_3$, $Na_2CO_3$, $K_2CO_3$, $MgCO_3$, $Cs_2CO_3$, $BaCO_3$, MeMgCl, EtMgCl, MeMgBr, EtMgBr, MeMgI and EtMgI.

$M_2$ can be a hydrogen atom or metal species used in any palladium or nickel cross-coupling protocols known in the art, for example, Stille, Sonogashira, Suzuki or Negishi cross-coupling reactions using stannanes (eg, aryl or alkylstannanes, boronic acids/esters or zinc based compounds e.g. $ZnCl$, $ZnI_2$, $ZnBr_2$, $ZnOTf_2$) for example based on Mg, Zn, Cu, B, Si, Mn, Sn, Ge or Al. Particularly suitable $M_2$ include ZnCl, $(alkyl)_3Sn$, $(aryl)_3Sn$, $B(OR)_2$ (R is, eg, H alkyl, alkenyl or alkynyl), MgBr, MgCl and MgI. Preferably the palladium catalysed coupling reactions may also include a co-catalyst, for instance, CuI, in the presence of a suitable base such as a trialkyl amine base.

In a particularly preferred form of this aspect of the invention both $M_1$ and $M_2$ are derived from a Grignard reagent such as an alkyl magnesium halide e.g. $C_{1-4}$alkylMgBr, (Cl) or (I). Suitable $M_1$ and $M_2$ thus include MgCl, MgBr and MgI.

Where X is NR, the nitrogen atom of the starting aniline is suitably protected by a nitrogen protecting group or as an imine. Suitable nitrogen protecting groups are known to those skilled in the art of organic synthesis and include acyl groups (eg acetyl, trifluoroacetyl), phenyl, benzyl and benzoyl. Other suitable nitrogen protecting groups may be found in *Protective Groups in Organic Synthesis*, T. W. Greene and P. Wutz, John Wiley & Son, 3rd Edition.

The coupling agent used in this first step to form (2) is preferably a nickel or palladium based coupling agent. Suitable coupling agents are known in the art and include $Pd(PPh_3)_2Cl_2$, $Pd(PPh_3)_4$, $Pd(dibenzylideneacetone)_3$ and $PdCl_2(CH_3CN)_2$.

Such coupling reactions are generally performed at temperatures below room temperature, most preferably at 0° C. and below. It is also preferred that such reactions are carried out under an inert atmosphere of either nitrogen or argon. Suitable solvents include ether solvents such as THF and diethyl ether.

The metallated (2) can be reacted, in situ, with Halogen-$R^2$ in the presence of a palladium catalyst in an atmosphere of CO to form (4). This may be accomplished by evacuating the inert reaction gas present in the initial coupling step and replacing said gases with CO. In this system it is also preferred that the initial reaction solvent is replaced with a more polar solvent such as, for instance, DMSO. Removal of the initial reaction solvent may be achieved in vacuo.

The preparation of benzo[b]thiophenes and benzo[b]selenophenes of formule (I), (Ia) or (Ib) are constructed using a variation of the methods described for the benzo[b]furans and indoles. In particular, the sulfur or selenium atom, X, must be protected by a suitable protecting group (P) to circumvent competitive coupling of a thiolate or selenoate to the aryl halide to afford xanthones or selenones. Suitable sulfur and selenium protecting groups are those which are capable of sustaining a positive charge. Examples include benzyl, allyl, and alkyl. This method can also be used as an alternative method for the formation of benzo[b]furans and indoles where X=O or NR and P=benzyl, allyl, and alkyl or where XP is an imine.

As used herein a Hal$^+$ producing agent is an agent which can effectively act as a Hal$^+$ source. Examples of Hal$^+$ producing agents include $I_2$, $Br_2$, $Cl_2$, IBr, ICl, chloroacetamide, iodoacetamide, N-chlorosuccinamide, N-bromosuccinamide and N-iodosuccinamide. Preferably, as shown in Scheme 1, the Hal$^+$ producing agent is $I_2$. Cyclisation of (2) can be effected by treating (2) with Hal$^+$ to afford (3). Such reactions may be carried out in a variety of solvents including ionic liquids.

The coupling of (3) with the moiety $M^1$-aryl or $R_2$—C(O)—Hal to produce (4) can be carried out via palladium-mediated coupling and/or metallation techniques as known in the art. For example, lithiation of (3) (eg using nBuLi) allows for coupling with

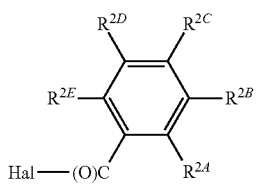

(Hal is I, Br or Cl, preferably Cl). In another embodiment, a carbonylation reaction can be carried out to access (4) by reacting (3) and

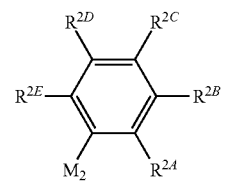

with a palladium catalyst in the presence of CO.

Compounds (5) can be prepared by reacting (3) with a phenolate, phenothiolate or phenoselenoate anions or with an appropriately activated aniline in the presence of a base and palladium or copper catalyst. SO, $SO_2$, SeO and $SeO_2$ derivatives can be prepared by controlled oxidation of the corresponding sulphides (i.e., where L=S) and selenides (i.e. where L=Se), respectively.

Scheme 2 represents an alternative approach to the compounds of the present invention.

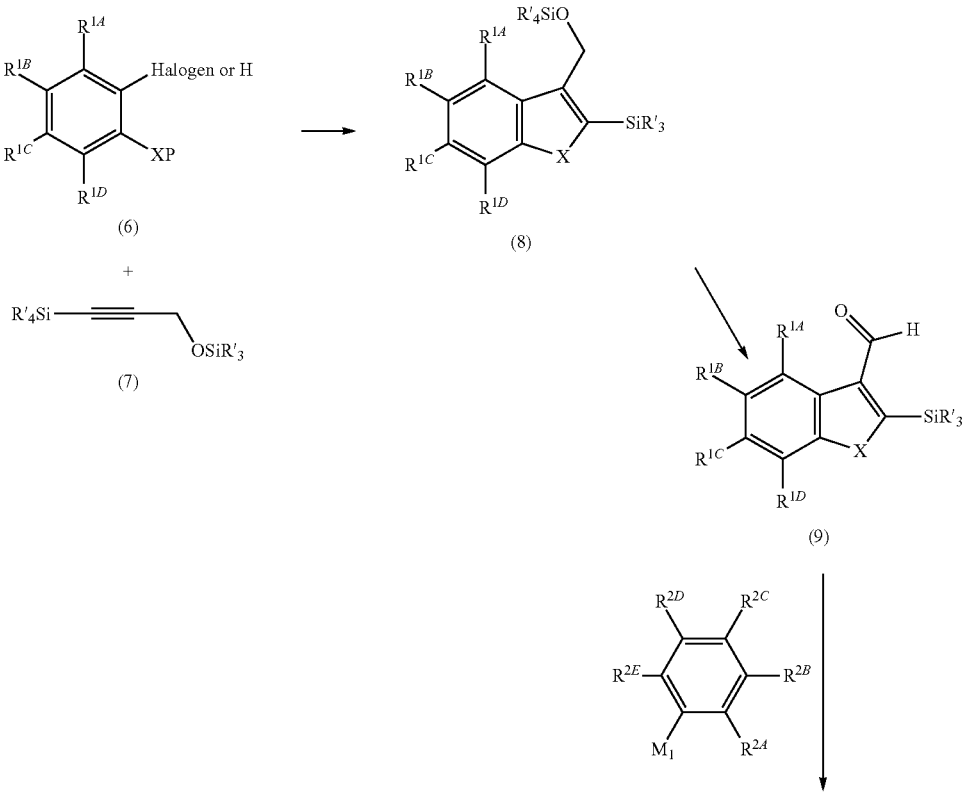

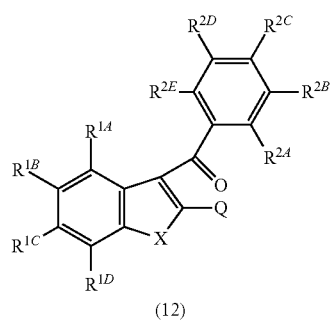 (12)

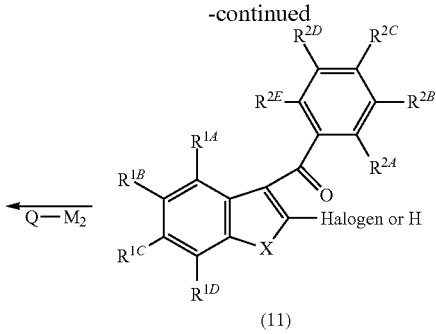 (11)

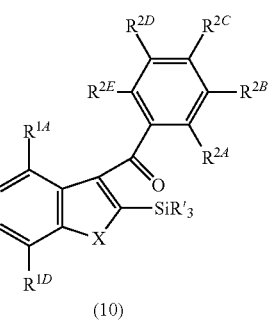 (10)

where Q is for example H, optionally substituted alkyl, optionally substituted alkenyl, optionally substituted alkynl, OR", SR", NR"R" or NR"'NR"', and X is S, NR', O or Se.

The compounds of the present invention represented by (12) can alternatively be prepared by palladium coupling compounds (6) with an alkyne (7) to form (8) under the conditions described by Bishop, B. C., et al, Synthesis, 1997, 1315. The reaction sequence involves the desilylation and oxidation of the C-3 silyl ether to afford a formyl group. Desilylation can be carried out with the use of either an aqueous acid (for e.g. hydrochloric acid) or by using a fluoride source. Oxidation can be carried out using $CrO_3$, $MnO_2$, dichlorodicyanoquinone (DDQ) or under Swern conditions. Addition of

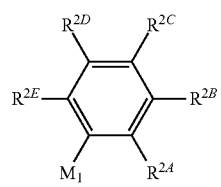

to (9) can be carried out under standard 1,2-addition conditions (for example where $M_1$=Li or Mg) followed by oxidation of the tertiary alcohol to ketone (10). Suitable oxidants include $CrO_3$, $MnO_2$, dichorodicyanoquinone (DDQ) or under Swern conditions. Conversion of the C-2 silyl group of (10) to a group suitable for Q addition can be carried out with ICl, IBr or Br (for when (11) bears a halogen which is I or Br) or TBAF (for when (11) is H).

If the C-2 position bears a suitable halogen, (11) can be reacted with $Q-M_2$ by either Suzuki coupling conditions (e.g. $M_2$=B(OH$_2$)), Negishi coupling conditions (e.g. $M_2$=Zn), Stille coupling conditions (e.g. $M_2$=Sn(alkyl)$_3$), or other palladium mediated couplings where $M_2$=Cu, Zr, Al. These reactions provide for connection of Q to the C-2 position of (12) through a C—C bond. Connection of Q to the C-2 position of (12) through a C—N bond is also possible by direct nucleophilic substitution of a deprotonated amine or by reaction of an amine with (11) in the presence of a base (e.g. trialkylamine, pyridine, $Na_2CO_3$, $K_2CO_3$, etc).

Scheme 3 represents a further approach to the compounds of the present invention.

Scheme 3

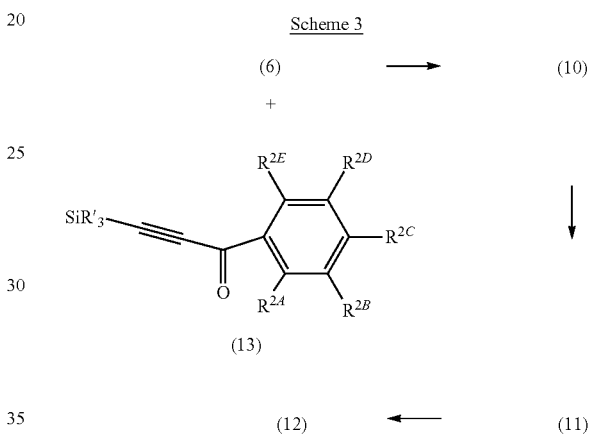

where Q is for example H, for example optionally substituted alkyl, optionally substituted alkenyl, optionally substituted alkynl, OR", SR", NR"R", CN, or NR"'NR"'; and X is S, NR', O or Se.

Compound (10) can be prepared by palladium coupling compounds (6) with an alkyne (13) under the conditions discussed previously in relation to the analogous reaction depicted in Scheme 2. Conversion of the C-2 silyl group of (10) to a halogen substituent (11) can be carried out with ICl, IBr, or $Br_2$. Subsequent coupling of (11) with a Q group may be carried out by reacting (11) with nucleophilic CN, NR"R", SR" or OR" anions.

For both schemes 2 and 3 compounds where Q=H can be prepared by protodesilylation of either compound (9) or (10).

An important aspect of the present invention relates to compounds which possess tubulin binding activity, as well as possessing selectivity and/or better solubility. In particular it has been found that the introduction of acyclic groups into the C2-position of benzofuran, indole, benzothiophene or benzoselenophene based TPIs, can give rise to improved anticancer properties over the same compounds which bear aryl groups at C-2. Furthermore, it has been shown that the potency of such compounds can be further increased by the introduction of a polar heteroatom in the C-7 position ($R^{1D}$) where an electron donating group exists at C-6 ($R^{1C}$).

Figure 2:
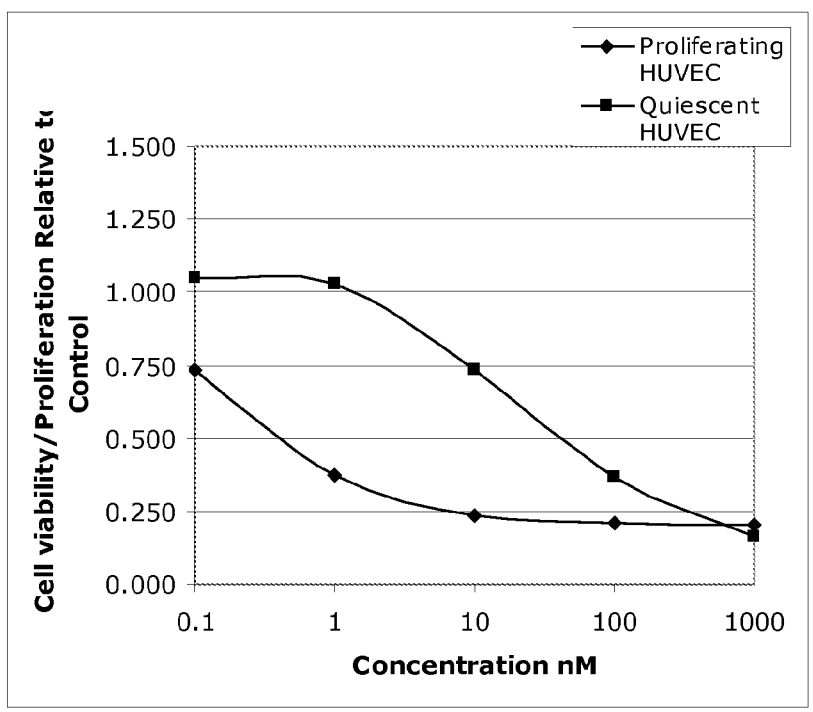
FIG. 2 depicts a graph of cell viability/proliferation relative to control against concentration of compound example 11 (nM) against proliferating and quiescent endothelial cells.

TPI compounds are important in the treatment of cancers primarily as a result of their capacity to selectively shut down blood flow through a tumour. Compounds that inhibit tumour blood flow are generally referred to as vascular disrupting agents (VDAs) (Tozer, G. M.; Kanthou, C.;

Baguley, B. C. *Nature Rev.*, Vol. 5, 2005, 423). TPIs are VDAs because they inhibit a certain cell signalling pathway associated with microtubules, leading to interference in the regulation of the cytoskeleton of the endothelial cells that line the blood vessels of the tumour. As a result, these usually flat cells become more rounded, ultimately occluding blood flow through the vessels. The selectivity associated with these agents results from the fact that tumour vasculature is weaker and more prone to collapse than normal vasculature. Nonetheless, a number of the dose limiting toxicities associated with VDAs are due to a reduction in blood flow in healthy tissues. An important aspect of the present invention is the combination of the specific $R^{1D}$ and $R^{1C}$ groups together with the Q-group confers greater potency and selectivity upon TPI compounds (see Table 1). In these preferred compounds selectivity is not simply reliant on the predisposition of tumour vasculature towards collapse when challenged with a VDA but on a capacity of the VDA to distinguish between tumour endothelial cells and normal endothelial cells. Normal endothelial cells, found in healthy tissues, are in a "quiescent" state and tumour endothelial cells are in an "activated" state. Most VDAs do not distinguish between these two states, for example CA4 (1) is equally potent against quiescent and activated endothelial cells (see FIG. 1). However, it has been discovered that certain acyclic Q-groups in conjunction with specific $R^{1D}$ and $R^{1C}$ groups may confer selectivity upon the compounds of the formulae I, Ia, Ib and II (see FIG. 2). These compounds (see, for instance, compound examples 9, 11 and 15 in Table 1) show higher potency towards tumour endothelial cells (activated) over normal endothelial cells (quiescent).

Figure 3:
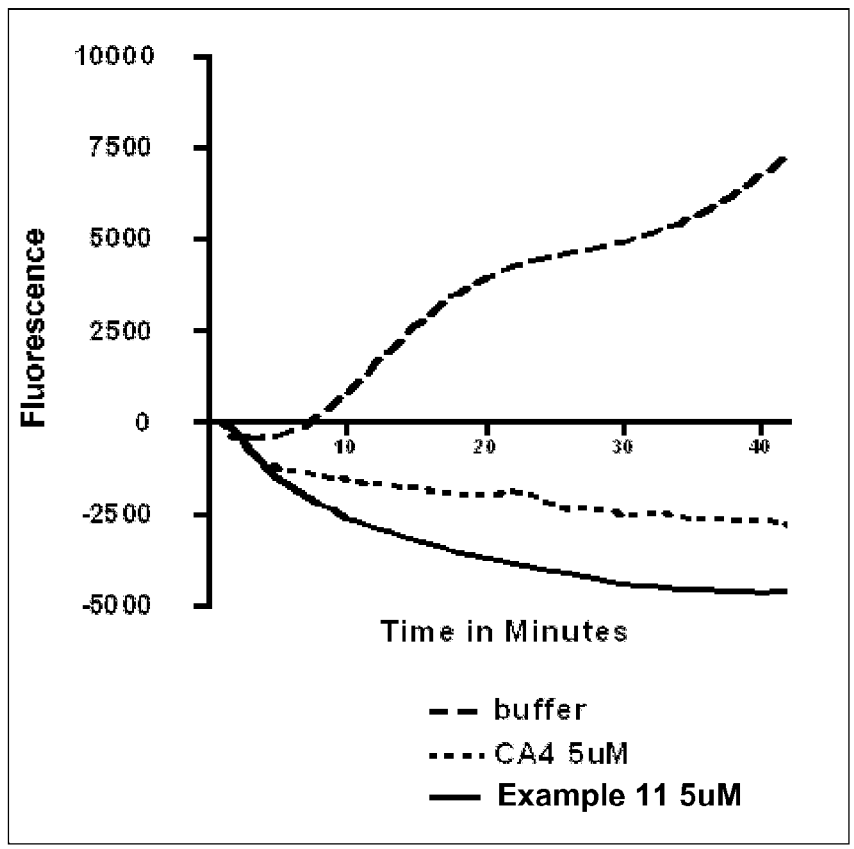
FIG. 3 depicts a graph of fluorescence against time (mins) in relation to inhibition of tubulin polymerisation by CA4 (1), compound example 11, and a buffer solution.
Figure 4:
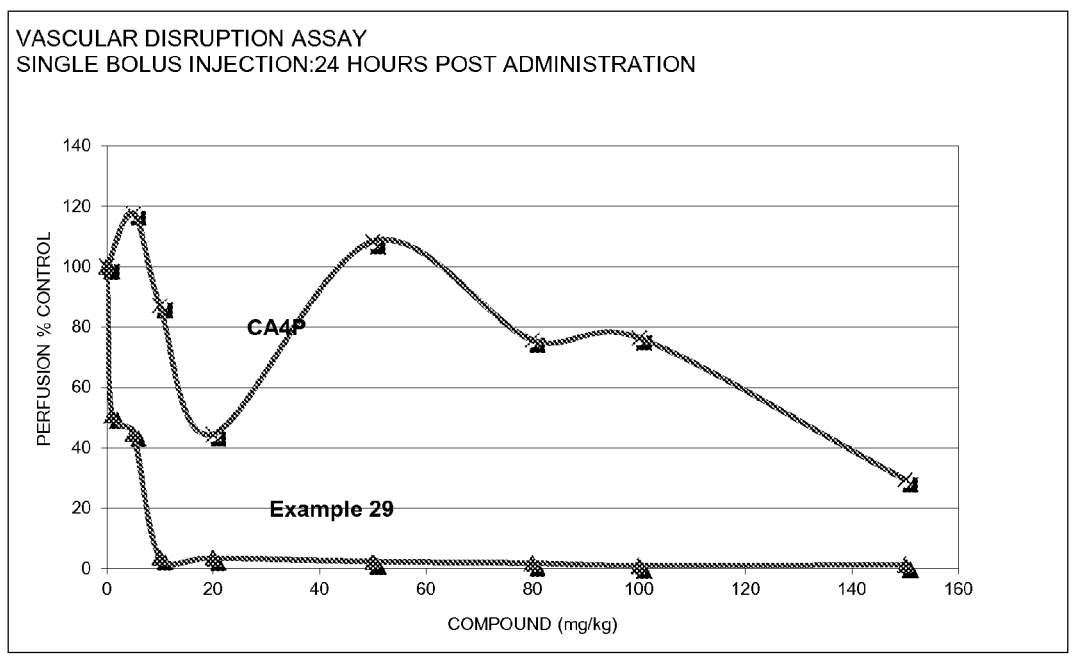
FIG. 4 depicts a graph of % perfusion control against an amount of compound (mg/kg) in relation to comparative levels of vascular shutdown (reduction in tumour perfusion) between CA4P (2) and compound example 29 of the present invention.

Compound examples 11 and 29 demonstrated significantly greater potency than CA4 (1) in inhibiting tubulin polymerisation and at shutting-down tumour vasculature (see FIGS. 3 and 4).

In another beneficial aspect the invention allows for the capacity to introduce an acyclic Q group in compounds of formulae I, Ia, Ib and II to affect the solubility and ADMET (absorption, distribution, metabolism excretion and toxicity) properties of the TPI compound. These pharmacokinetic properties of the drug are also important in attaining the maximum therapeutic index for a VDA. It has been reported that a low volume of distribution (concentration of the drug in the vasculature) and short half-life are desirable for a VDA (Rustin, J et al. *J. Clin. Oncol.* 2003, 21, 2815; Davies P. D. et al. *Cancer Res.* 2002, 62, 7247). A low volume of distribution maximises drug exposure to the target tissue, vasculature endothelium, and minimises exposure to other tissues (outside the vasculature) that may be adversely affected by TPIs. Also, tumour vasculature shuts down very quickly upon exposure to a VDA, so that ongoing exposure systemically is undesirable as it will not further affect the tumour and may lead to side-effects. A low volume of distribution can be achieved by increasing the hydrophilicity of a compound (introduction of polar, acidic and/or basic groups). Short-half life can be achieved by a high rate of clearance (hepatic or renal clearance), which in turn can be achieved by incorporating readily metabolised groups and/or in the introduction of very polar groups (polar compounds are more readily cleared through the kidneys). Compounds of formulae I, Ia, Ib and II are able to tolerate large variations in the acyclic nature of Q whilst retaining considerable potency (see Table 1). These compounds include systems that contain polar functionalities (carboxylates, amine and amides etc) and that contain metabolically labile groups (e.g. OH and NH groups that can be glucuronidated.

As mentioned previously, the preferred compounds of the invention having increased tubulin binding activity or anti-tumour vasculature activity, can be useful in methods of therapy. In particular these compounds may be used for treating tumours. As used herein the term "tumour" is used to define any malignant cancerous growth, and may include leukemias, melanomas, colon, lung, ovarian, skin, breast, prostate, CNS, and renal cancers, as well as other cancers.

The compounds of the invention having tubulin binding activity may also be used in the treatment of solid tumours, e.g. breast cancer.

The invention also provides for the use of a compound of formulae (I), (Ia), (Ib), or (II) in the manufacture of a medicament for treating tumours.

There is also provided a method of treatment of solid tumours comprising the administration of an effective amount of a compound of formula (I), (Ia), (Ib) or (II) to a subject in need thereof.

However, it will be understood that the compounds of the invention can be used in the treatment of any disease state for which tubulin polymerisation plays a crucial role.

In particular, the present compounds can be used in treating inflammation. Such inflammatory conditions may include acute and chronic inflammatory conditions such as rheumatoid arthritis, inflammatory bowel disease, Crohn's disease, psoriasis, and the like.

Compounds of the invention which possess bioactivity, such as tubulin binding activity, can be formulated as a composition, particularly a pharmaceutical composition, together with a pharmaceutically acceptable additive.

The compounds of the invention are administered to the subject in a treatment effective amount. As used herein, a treatment effective amount is intended to include at least partially attaining the desired effect, or delaying the onset of, or inhibiting the progression of, or halting or reversing altogether the onset or progression of the particular disease of condition being treated.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages may lie within the range of about 0.1 ng per kg of body weight to 1 g per kg of body weight per dosage. A typical dosage is in the range of 1 μg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

Suitable dosage amounts and dosing regimens can be determined by the attending physician and may depend on the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyl-dodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The novel bioactive compounds of the invention can be administered to a subject as a pharmaceutically acceptable salt thereof. It will be appreciated however that non-pharmaceutically acceptable salts also fall within the scope of the present invention since these may be useful as intermediates in the preparation of pharmaceutically acceptable salts. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

It will be appreciated that any compound that is a prodrug of a compound of formule (I) or (II) is also within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group (for instance at the C-7 position or $R^{1D}$) is converted into an ester, such as an acetate or phosphate ester, or where a free amino group (for instance at the C-7 position or $R^{1D}$) is converted into an amide (e.g. α-aminoacid amide). Procedures for esterifying, e.g. acylating, the compounds of the invention are well known in the art and may include treatment of the compound with an appropriate carboxylic acid, anhydride or chloride in the presence of a suitable catalyst or base. A particularly preferred prodrug is a disodium phosphate ester. The disodium phosphate ester of novel compounds of the invention may be useful in increasing the solubility of the compounds. This would, for instance, allow for delivery of the compound in a benign vehicle like saline. The disodium phosphate ester may be prepared in accordance with the methodology described in Pettit, G. R., et al, *Anticancer Drug Des.*, 1995, 10, 299.

Alternatively, the choice of an appropriate hydrophilic group as Q may also provide the compound with better solubility properties. This may not only serve to avoid the need to prepare prodrugs (to increase solubility) but may also lead to an increase in targeting tumor vasculature pharmacokinetically. Examples of solubilizing groups which may be present as Q include substituted amino, amino acids, tetrazoles, sulphonamides, and so on.

The compounds of the invention may be in crystalline form either as the free compounds or as solvates (e.g. hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, e.g., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

The mode of proliferative diseases, such as solid tumors, is multi-factorial. In the treatment of such diseases drugs with different mechanisms may be combined (i.e. combination therapies). The compounds of the invention may be particularly useful in combination therapy, e.g. combining the treatment with other chemotherapeutic or radiation treatments.

For instance in order to potentiate anti-tumor treatments using the compounds of the present invention one or more other cytotoxic compounds including 5-FU, oxaliplatin, paclitaxel, gemcitabine, docetaxel, cisplatin, and doxorubicin may also be administered. The combination therapy may also include the addition of an angiogensis inhibitor (e.g., Avastin) or another agent or therapy (e.g., radiotherapy).

Compounds that are vascularly active may be preferably administered in combination with antihypertensive (e.g. sublingual glyceryl trinitrite) or antihypotensive agents.

The combination partners in such therapies may be administered together, one after the other, separately in one combined unit dosage or in separate unit dosage forms.

The synthetic methods and processes described herein to prepare the compounds of the present invention are amenable to solid phase synthetic techniques and/or combinatorial chemistry to produce individual compounds or libraries of compounds.

Traditionally, drug candidates have been synthesised individually, this being a time consuming and laborious process if the synthetic sequence contains even just a few steps and large numbers of compounds are to be evaluated for their biological activity. Combinatorial synthesis is an emerging technique for effecting the generation of large libraries of molecules and has been successfully exploited in the synthesis and evaluation of small organic libraries. These libraries and their starting substrates may exist as molecules in free solution or preferably, linked to a solid support, for example, beads, pins, microtitre plates (wells) or microchips which can be polymeric, glass, silica or other suitable substrate. Chemical diversity can be achieved by either parallel or split (split and mix) syntheses wherein each step has the potential to afford a multitude of compounds. Solution phase libraries may be prepared via parallel syntheses wherein different compounds are synthesised in separate reaction vessels in parallel, often in an automated fashion. Alternatively, attachment of the individual components employed in a synthetic sequence to an appropriate solid phase support allows for the further creation of chemical diversity by utilising not only parallel synthesis but also split synthesis wherein the solid support containing the compounds prepared in the prior step can be split into a number of batches, treated with the appropriate reagent and recombined.

The substrates can be attached to a solid support surface by any linkers known in the art. The linkers may be any component capable of being cleaved to release the substrate or final compound from the support.

Preferably, the solid support is a polymer support. Examples of polymeric supports currently used in solid phase synthesis include: alkenyl resins: e.g. REM resins; BHA resins: e.g. benzhydrylamine (polymer-bound hydrochloride, 2% crosslinked), benzhydryl chloride (polymer bound); Br-functionalised resins: e.g. brominated PPOA resin, brominated Wang resin; Chloromethyl resins: e.g. 4-methoxybenzhydryl chloride (polymer bound); CHO-functionalised resins: e.g. indole resin, formylpolystyrene; Cl-functionalised resins: e.g. Merrifield's resin, chloroacetyl (polymer bound); $CO_2H$-functionalised resins: e.g. carboxypolystyrene; 1-functionalised resins: e.g. 4-iodophenol (polymer bound); Janda Jels™; MBHA resins: e.g. 4-methylbenzhydrylamine hydrochloride (polymer bound), 4-hydroxymethylbenzoic acid-4-methyl benzhydrylamine (polymer bound); Amine-functionalised resins: e.g. (aminomethyl)polystyrene, PAL resin, Sieber amide resin; Nitrophenyl carbonate resins: e.g. 4-nitrophenyl carbonate (polymer bound); OH-functionalised resins: e.g. 4-benzyloxybenzyl alcohol (polymer bound); Hydroxy methyl resins: e.g. benzyl alcohol (polymer bound); HMBA resin; Oxime resins; Rink acid resin; Triazine-based resin; Trityl amine resins; Trityl resins: e.g. trityl-chloride (polymer bound), 2-chlorotrityl alcohol, 1,3-diaminepropane trityl.

Thus, individual compounds or libraries of compounds can be synthesised by initially attaching the first compound substrate to a solid support surface which can be performed by providing a plurality of solid support surfaces, suitably derivatising each of the surfaces with groups capable of reacting with either the compound substrate or a linker moiety attached thereto. The various support surfaces with the attached first compound substrate can then be subjected to various reaction conditions and second compound substrates to provide a library of attached compounds, which may, if necessary, be reacted further with third and subsequent compound substrates or varying reactions conditions. Attachment and detachment of substrates and products can be performed under conditions similar to those as described in Johnson, M. G., et al., *Tetrahedron,* 1999, 55, 11641; Han Y., et al. *Tetrahedron* 1999, 55, 11669; and Collini, M. D., et al., *Tetrahedron Lett.,* 1997, 58, 7963.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Biological Data (i) In Vitro Studies

TABLE 1

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%. Entries 1-4, 13, 36, 39, and 45 provided for comparison, all other entries are compounds of the invention.

| Entry | Example/ Comparator | Structure | Cancer cell line[a]: $IC_{50}$, nM | HUVECs[c] Tum: $IC_{50}$, nM Norm: $IC_{50}$, nM |
|---|---|---|---|---|
| | Comparator A | (structure) | 5 | Tum: 1-10 Norm: 1-10 |
| | Comparator B | (structure) | 5 | Tum: 1-10 Norm: 1-10 |
| | Comparator C Example 5 | (structure) | 55 | Tum: 10-100 Norm: 10-100 |

TABLE 1-continued

*In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%. Entries 1-4, 13, 36, 39, and 45 provided for comparison, all other entries are compounds of the invention.*

| Entry | Example/ Comparator | Structure | Cancer cell line[a]: $IC_{50}$, nM | HUVECs[c] Tum: $IC_{50}$, nM Norm: $IC_{50}$, nM |
|---|---|---|---|---|
| | Comparator D Example 3 | | 500 | Tum: 100-1000 Norm: 100-1000 |
| | Example 6 | | 45 | Tum: 10-100 Norm: 10-100 |
| | Example 52 | | 35 | Tum: 100-1000 Norm: 100-1000 |
| | Example 53 | | 800 | Tum: >1000 Norm: >1000 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%. Entries 1-4, 13, 36, 39, and 45 provided for comparison, all other entries are compounds of the invention.

| Example/ Entry Comparator | Structure | Cancer cell line[a]: $IC_{50}$, nM | HUVECs[c] Tum: $IC_{50}$, nM Norm: $IC_{50}$, nM |
|---|---|---|---|
| Example 18 | | 3.5 | Tum: 1-10<br>Norm: 0.1-1 |
| Example 9 | | 1.2 | Tum: 0.1-1<br>Norm: 1-10 |
| Example 8 | | 3.3 | Tum: 1-10<br>Norm: 1-10 |
| Example 10 | | 35 | Tum: 1-10<br>Norm: 10-100 |

TABLE 1-continued

*In Vitro Data for Compounds: These are the results for growth inhibition studies of compounds using the Sulforhodamine B (SRB) or Systmex cell counting (CC) assays. IC$_{50}$ is the concentration required to inhibit net cell growth by 50%. Entries 1-4, 13, 36, 39, and 45 provided for comparison, all other entries are compounds of the invention.*

| Example/ Entry Comparator | Structure | Cancer cell line[a]: IC$_{50}$, nM | HUVECs[c] Tum: IC$_{50}$, nM Norm: IC$_{50}$, nM |
|---|---|---|---|
| Example 11 | | 2.0 | Tum: 0.1-1 Norm: 10-100 |
| Comparator E Example 30 | | 575 | Tum: 100-1000 Norm: 100-1000 |
| Example 23 | | 260 | Tum: 100-1000 Norm: 100-1000 |
| Example 14 | | 2.0 | Tum: 0.1-1 Norm: 1-10 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%. Entries 1-4, 13, 36, 39, and 45 provided for comparison, all other entries are compounds of the invention.

| Example/ Entry Comparator | Structure | Cancer cell line[a]: $IC_{50}$, nM | HUVECs[c] Tum: $IC_{50}$, nM Norm: $IC_{50}$, nM |
|---|---|---|---|
| Example 13 | | 8.0 | Tum: 1-10 Norm: 1-10 |
| Example 2 | | 1-10[b] | Tum: 1-10 Norm: 1-10 |
| Example 15 | | 1-10[b] | Tum: 1-10 Norm: 1-10 |
| Example 21 | | 10-100[b] | Tum: 10-100 Norm: 10-100 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%. Entries 1-4, 13, 36, 39, and 45 provided for comparison, all other entries are compounds of the invention.

| Entry | Example/ Comparator | Structure | Cancer cell line[a]: $IC_{50}$, nM | HUVECs[c] Tum: $IC_{50}$, nM Norm: $IC_{50}$, nM |
|---|---|---|---|---|
| | Example 20 | | $1-10^b$ | Tum: 1-10 Norm: 1-10 |
| | Example 16 | | $0.1-1^b$ | Tum: 1-10 Norm: 1-10 |
| | Example 17 | | $1-10^b$ | Tum: 1-10 Norm: 1-10 |
| | Example 19 | | $0.1-1^b$ | Tum: 1-10 Norm: 1-10 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%. Entries 1-4, 13, 36, 39, and 45 provided for comparison, all other entries are compounds of the invention.

| Example/ Entry Comparator | Structure | Cancer cell line$^a$: $IC_{50}$, nM | HUVECs$^c$ Tum: $IC_{50}$, nM Norm: $IC_{50}$, nM |
|---|---|---|---|
| Example 24 | | 1-10$^b$ | Tum: 1-10 Norm: 1-10 |
| Example 25 | | 1-10$^b$ | Tum: 1-10 Norm: 1-10 |
| Example 22 | | 1-10$^b$ | Tum: 1-10 Norm: 1-10 |
| Example 26 | | | Tum: 1-10 Norm: 1-10 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%. Entries 1-4, 13, 36, 39, and 45 provided for comparison, all other entries are compounds of the invention.

| Entry | Example/ Comparator | Structure | Cancer cell line[a]: $IC_{50}$, nM Norm: $IC_{50}$, nM | HUVECs[c] Tum: $IC_{50}$, nM Norm: $IC_{50}$, nM |
|---|---|---|---|---|
| | Example 27-HCl | | | Tum: 100-1000 Norm: 100-1000 |
| | Example 28 | | | Tum: 100-1000 Norm: 10-100 |
| | Example 31 | | | Tum: 1-10 Norm: 1-10 |
| | Example 32 | | | Tum: 0.1-1.0 Norm: 0.1-1.0 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%. Entries 1-4, 13, 36, 39, and 45 provided for comparison, all other entries are compounds of the invention.

| Entry | Example/ Comparator | Structure | Cancer cell line[a]: $IC_{50}$, nM Norm: $IC_{50}$, nM | HUVECs[c] Tum: $IC_{50}$, nM Norm: $IC_{50}$, nM |
|---|---|---|---|---|
| | Example 34 | | | Tum: 1-10<br>Norm: 1-10 |
| | Example 35 | | | Tum: 1-10<br>Norm: 1-10 |
| | Example 36 | | | Tum: 1-10<br>Norm: 1-10 |
| | Example 37 | | | Tum: 10-100<br>Norm: 10-100 |

TABLE 1-continued

In Vitro Data for Compounds: These are the results for growth inhibition studies of compounds using the Sulforhodamine B (SRB) or Systmex cell counting (CC) assays. IC$_{50}$ is the concentration required to inhibit net cell growth by 50%. Entries 1-4, 13, 36, 39, and 45 provided for comparison, all other entries are compounds of the invention.

| Entry | Example/ Comparator | Structure | Cancer cell line[a]: IC$_{50}$, nM | HUVECs[c] Tum: IC$_{50}$, nM Norm: IC$_{50}$, nM |
|---|---|---|---|---|
|  | Comparator F Example 50 | 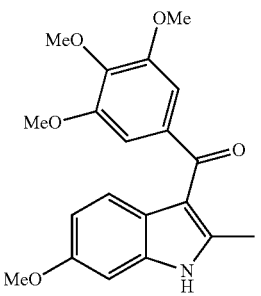 [SMILES: COc1ccc2c(C(=O)c3cc(OC)c(OC)c(OC)c3)c(C)[nH]c2c1] |  | Tum: 0.1-1 Norm: 0.1-1 |
|  | Example 39 | 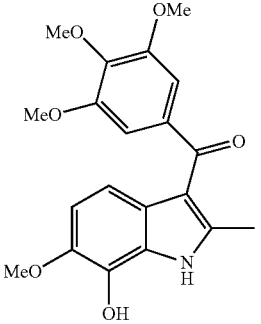 [SMILES: COc1cc(C(=O)c2c(C)[nH]c3c(O)c(OC)ccc23)cc(OC)c1OC] |  | Tum: 0.01-0.1 Norm: 0.1-1 |
| 38. | Example 40 | 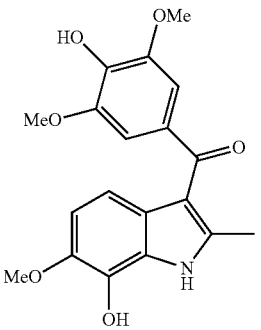 [SMILES: COc1cc(C(=O)c2c(C)[nH]c3c(O)c(OC)ccc23)cc(OC)c1O] |  | Tum: 1-10 Norm: 10-100 |
|  | Comparator G Example 51 | 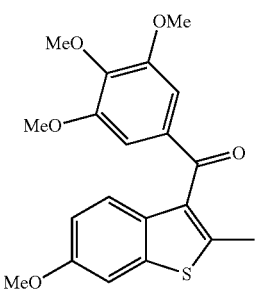 [SMILES: COc1ccc2c(C(=O)c3cc(OC)c(OC)c(OC)c3)c(C)sc2c1] |  | Tum: 1-10 Norm: 1-10 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%. Entries 1-4, 13, 36, 39, and 45 provided for comparison, all other entries are compounds of the invention.

| Entry | Example/ Comparator | Structure | Cancer cell line[a]: $IC_{50}$, nM Norm: $IC_{50}$, nM | HUVECs[c] Tum: $IC_{50}$, nM Norm: $IC_{50}$, nM |
|---|---|---|---|---|
| | Example 42 | | | Tum: 0.1-1 Norm: 1-10 |
| | Example 43 | | | Tum: 1-10 Norm: 1-10 |
| | Example 44 | | | Tum: 10-100 Norm: 10-100 |
| | Example 45 | | | Tum: 1-10 Norm: 1-10 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%. Entries 1-4, 13, 36, 39, and 45 provided for comparison, all other entries are compounds of the invention.

| Entry | Example/ Comparator | Structure | Cancer cell line[a]: $IC_{50}$, nM | HUVECs[c]: Tum: $IC_{50}$, nM Norm: $IC_{50}$, nM |
|---|---|---|---|---|
| | Example 46 | 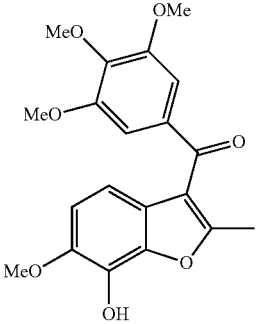 [SMILES: COc1cc(C(=O)c2c(C)oc3c(O)c(OC)ccc23)cc(OC)c1OC] | | Tum: 10-100 Norm: 100-1000 |
| | Comparator H | 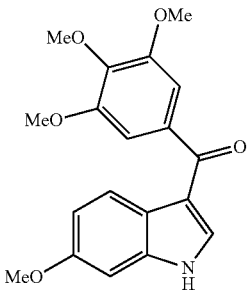 [SMILES: COc1ccc2c(C(=O)c3cc(OC)c(OC)c(OC)c3)c[nH]c2c1] | | Tum: 1-10 Norm: 1-10 |

[a] Unless otherwise stated the cancer cell line is MCF-7.
[b] The cancer cell line is MDA-MB-231.
[c] Human umbilical vein endothelial cells (HUVECs) tumour type activated endothelial cells (Tum) and normal quiescent type endothelial cells (Norm).

General Description of Biological Experiments:

Tubulin Polymerisation Assay:

Tubulin polymerisation inhibition assays were performed using a fluorescent-based detection kit (#BK011, Cytoskeleton) according to the instructions of the manufacturer. The test compound was added to a 2 mg/ml tubulin solution containing 20% glycerol and 1 mM GTP in 1×Buffer 1 (Buffer 1: 80 mM piperazine-N,N'-bis[2-ethanesulfonic acid]sequisodium salt; 2 mM magnesium chloride; 0.5 mM Ethylene glycol-bis(b-amino-ethyl ether)N,N,N',N'-tetra-acetic acid, pH 6.9, 10 uM fluorescent reporter). Fluorescence was measured over a period of 42 minutes at 1 minute intervals. Increased fluorescence indicates increase in tubulin polymerisation. There is a ten-fold increase in the affinity of the fluorescent reporter for polymerised tubulin compared to monomeric tubulin subunits. The result is a fluorescence signal that closely follows tubulin polymerisation.

Proliferation Assay—Quiescent Endothelium:

Human umbilical vein endothelial cells (CC-2519, Clonetics) were plated at 15000 cells/well in EBM2 (CC-3156, Clonetics)+0.5% FBS (CC-4101A, Clonetics)+GA-1000 (CC-4381A, Clonetics) in a 96 well plate in triplicate. Cells were cultured overnight at 37° C. 5% $CO_2$. Medium was subsequently replaced with fresh medium including the compound or negative control. Cells were cultured for a period of 48 hrs. An MTT assay was performed to measure changes in cell numbers. Briefly, 20 µl of MTT reagent was added to cells containing 100 µl of EBM2+0.5% FBS and incubated at 37° C. for 2 hours. Absorbance was measured at 492 nm.

Proliferation Assay—Activated Endothelium:

Human umbilical vein endothelial cells (CC-2519, Clonetics) were plated at 2500 cells/well in EGM2 (CC-3162, Clonetics) in a 96 well plate in triplicate. Cells were cultured overnight at 37° C. 5% $CO_2$. Medium was subsequently replaced with fresh medium including the compound or negative control. Cells were cultured for a period of 48 hrs. An MTT assay was performed to measure changes in cell numbers. Briefly, 20 µl of MTT reagent was added to cells containing 100 µl of EGM2 and incubated at 37° C. for 2 hours. Absorbance was measured at 492 nm.

(ii) In Vivo Studies

Vascular Disruption Assay: Female athymic BALB/c-nu/nu mice (nude mice) were used for this study. Mice were between 6-8 weeks old and were purchased from the Animal Resource Centre, Perth, Western Australia and allowed to acclimatize for a couple of days. All the animals were housed under pathogen-free conditions and cared for in accordance with Flinders University of South Australia and NH&MRC guidelines and the Australian Code of Practice for the care and use of animals for scientific purposes. The human breast cancer MDA MB 231 was grown as orthotopic xenografts in the mammary fat pad of nude mice. Each mouse was injected with $2\times10^6$ cells in 50 µl Dulbecco's PBS subcutaneously just above the mammary fat pad, below the right forward limb. Tumors were selected for treatment when they reached a diameter of 100-150 $mm^3$ (3 weeks after implantation). The test compound (Example 29) was dissolved in saline solution and injected intravenously at concentrations ranging from 150 mg/kg-1 mg/kg in a total volume of 400 ul. Tumor bearing animals were injected intravenously with 10 mg/kg Hoechst 33342, 24 hours after the injection of the test compound. Animals were euthanised 1 minute after the Hoechst 33342 injection. Tumors were recovered for histochemical analysis. Tumor perfusion analysis was performed by assessing the amount of Hoechst 33342 staining across an entire tumor cross-section. 10 micron sections of frozen tumor biopsies were viewed under an ultraviolet light filter. Using a 4× objective lens, 8-bit monochromatic images were captured in succession, representing the total area of the tumor section. Composite images of the total tumor section were generated by overlaying common areas of the monochromatic images. Hematoxylin and Eosin-Y staining of the same tumor section was performed to identify non-tumor regions. Non-tumor regions were mapped on Hoechst 33342 composite images and excluded from the quantitation analysis. Quantitation was performed by measuring the pixel area of Hoechst 33342 staining and the total pixel area of the tumor region. Perfusion was expressed as a percentage of Hoechst 33342 stained area to total tumor area (see FIG. 4).

Tumor Growth Inhibition:

Balb/c nu/nu mice bearing MDA-MB-231 solid orthotopic tumors were treated with compound Example 29 at 40 mg/kg. Animals were i.v. dosed with a total of two cycles of Example 29 treatment. Each cycle was dosing on days and 8 followed by a three week no-dosing period. Tumor growth represented as a ratio to initial tumor volume is shown over a total of 72-days.

Figure 5:
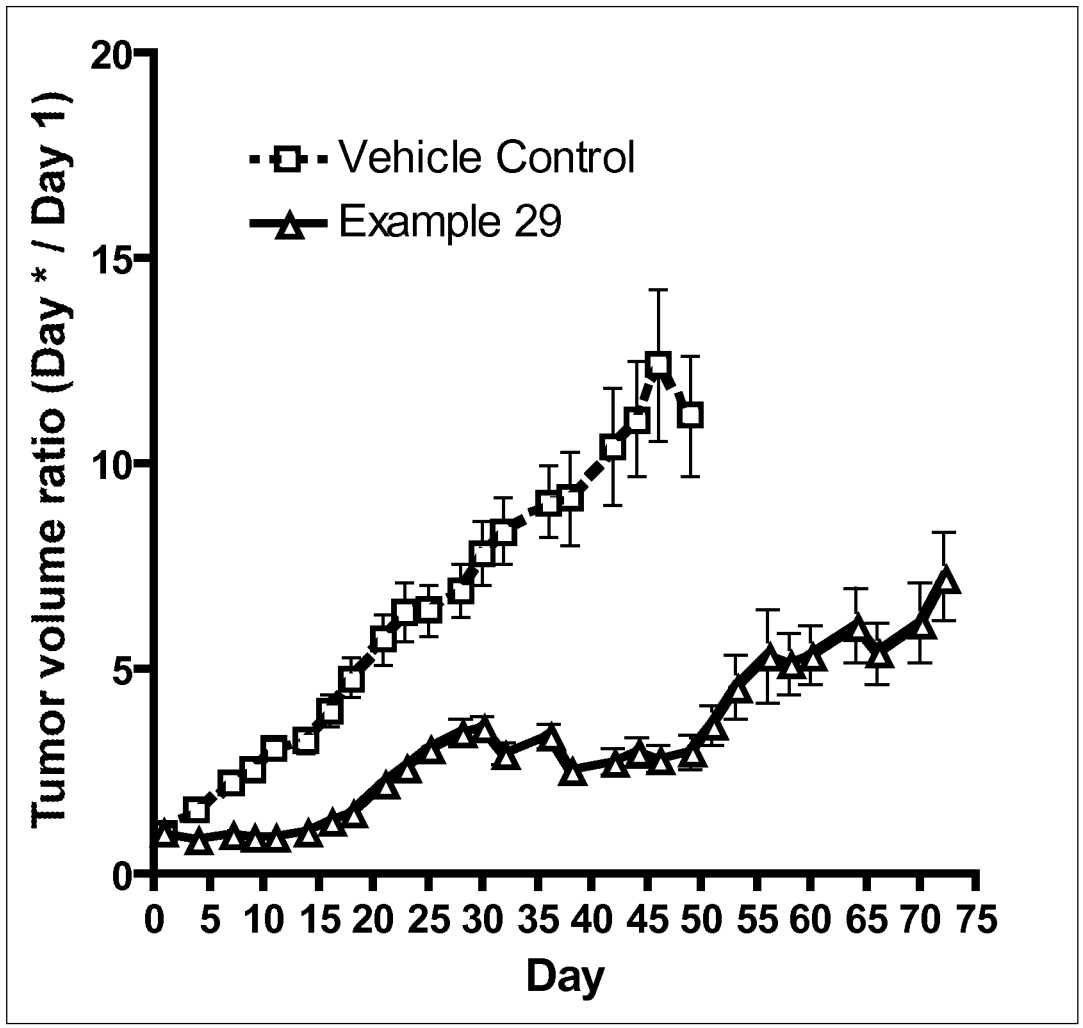
FIG. 5 depicts a graph of Tumor Volume ratio (Day*/Day 1) against time (Days) in relation to tumor growth inhibition of compound example 29 in Balb/c nu/nu mice bearing MDA-MB-231 orthotopic breast solid tumors.

Tumor growth as well as animal health were monitored for up to 72 days post-day 1 of treatment. The results seen in this experiment (see FIG. 5) clearly show tumor growth inhibition in animals treated with two cycles of Example 29. Significant differences in tumor growth between Example 29 treated (n=64) and vehicle treated (n=20) animals were observed as early as day 4 (p<0.001; unpaired t-test; Prism® analysis) through to Day 70.

Synthetic Protocols

Example 1

Preparation of (6-Methoxy-7-nitrobenzofuran-3-yl)(3,4,5-trimethoxyphenyl)methanone

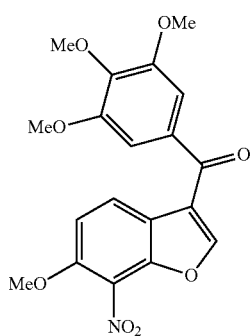 [SMILES: COc1cc(C(=O)c2coc3c([N+](=O)[O-])c(OC)ccc23)cc(OC)c1OC]

Step 1: 2-Nitro-3-methoxyphenol

To a mixture of 2.01 g (1.3 mmol) of 2-nitroresorcinol in 15 ml of dry pyridine 0.28 ml (1.36 mmol) of acetic anhydride was added dropwise at 0° C. The resulting mixture was allowed to warm to room temperature. After 1 h of stirring at room temperature the solvent was removed by evaporation in vacuo and the residue diluted to 10 ml with anhydrous acetonitrile. To this 2 g of anhydrous potassium carbonate was added followed by the addition of 1.5 ml of methyl iodide. The resulting suspension was stirred overnight at room temperature, filtered off and filtrate evaporated to dryness under reduced pressure to give 2.63 g of crude 3-methoxy-2-nitrophenyl acetate. This was dissolved in 15 ml of acetonitrile and 2 ml of concentrated ammonium hydroxide was added. The resulting mixture was allowed to stand for 30 minutes at room temperature and evaporated to dryness under reduced pressure. The residue was purified by flash column chromatography to give 1.36 g (62% yield) of pure title compound as red crystals; $^1$H NMR (CDCl$_3$) 3.92 (s, 3H, OMe); 6.51 (d, 1H, CH, J=8.5 Hz); 6.68 (d, 1H, CH, J=8.5 Hz); 7.35 (m, 1H, CH); 10.18 (s, 1H, OH).

Step 2: 6-Iodo-3-methoxy-2-nitrophenol

A mixture of 1.36 g (8 mmol) of the product of Step 1 and 0.68 g (8 mmol) of sodium bicarbonate was sonicated at room temperature until it become homogenous. The resulting mixture was cooled to 0° C. and 2.04 g (8 mmol) of iodine was added. After stirring for 1 h at room temperature the precipitate formed was filtered off, dried and recrystallized from ethyl ether to give 2.28 g (96% yield of pure title compound as an orange crystals; $^1$H NMR (CDCl$_3$) 3.92 (s, 3H, OMe); 6.41 (d, 1H, CH J=9 Hz); 7.82 (d, 1H, J=9 Hz); 10.37 (s, 1H, OH).

Step 3: 3-Methoxy-2-nitro-6-((trimethylsilyl)ethynyl)phenol

A modified procedure of Gottardo and Aguirre, Tetrahedron Letter, 2002(43), 7091-7094 was used.

A mixture of 0.0982 g (0.33 mmol) of the product of Step 2, 8.7 mg of copper iodide, 13.8 mg of palladium dichlorobis(triphenyl)phosphine and 0.5 ml of anhydrous triethylamine in 1.5 ml of anhydrous acetonitrile was degassed under reduced pressure and saturated with anhydrous nitrogen at 0° C. After stirring for about 10 minutes at 0° C., 0.07 ml (0.495 mmol) of trimethylsilylacetylene was added dropwise over 10 minutes. The resulting mixture was stirred overnight at room temperature and filtered through Celite. The filtrate was evaporated under reduced pressure and the residue was purified by flash column chromatography (silica gel; methylene chloride:ethyl acetate 1:1) to give 0.05 g (57% yield of pure title product as a yellowish crystals; $^1$H NMR (CDCl$_3$) 0.25 (s, 9H, SiMe); 3.9 (s, 3H, OMe); 6.5 (d, 1H, CH, J=8.8 Hz); 7.46 (d, 1H, CH, J=8.8 Hz); 8.81 (s, 1H, OH).

Step 4: (6-Methoxy-7-nitrobenzofuran-3-yl)(3,4,5-trimethoxyphenyl)methanone

A modified procedure of Hu et al, J. Org. Chem. 2002, 67, 2365-2368 was used.

A mixture of 0.04 g (0.151 mmol) of the title compound of Step 3 and 0.089 g (0.301 mmol) of 3,4,5,-trimethoxyiodobenzene, 0.1 g (0.73 mmol) of anhydrous potassium carbonate and 13.1 mg (0.0 µmol) of palladium tetrakis(triphenylphosphine) in 5 ml of anhydrous acetonitrile was degassed under reduced pressure and stirred for 24 hours at 80° C. under carbon monoxide balloon. The resulting mixture was cooled to room temperature, filtered through a pad of Celite and washed with 20 ml of methylene chloride. The combined filtrates were evaporated to dryness and the residue was purified by flash column chromatography to give 0.0295 g (50% yield) of pure title compound as a colorless solid.

¹H NMR (CDCl₃) 3.9 (s, 6H, OMe); 3.94 (s, 3H, OMe); 4.04 (s, 3H, OMe); 7.14 (s, 2H, CH aromatic); 7.15 (d, 1H, CH aromatic J=9 Hz); 8.1 (s, 1H, CH furan); 8.3 (d, 1H, J=9 Hz).

Example 2

Preparation of (7-Amino-6-methoxybenzofuran-3-yl) (3,4,5-trimethoxyphenyl)methanone

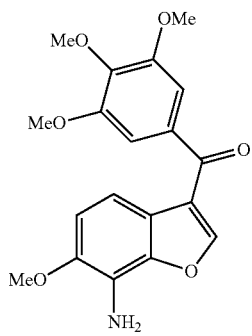 [SMILES: COc1cc(C(=O)c2coc3c(N)c(OC)ccc23)cc(OC)c1OC]

A mixture of 0.022 g (0.057 mmol) of (6-methoxy-7-nitrobenzofuran-3-yl)(3,4,5-trimethoxyphenyl)methanone, 0.1 g of ammonium formate and 0.1 g of 10% palladium on carbon in 5 ml of a mixture of 1,2-dimethoxyethane and methanol (4:1) was refluxed for 30 minutes (TLC controlled reaction). After cooling to room temperature the mixture was filtered through a pad of Celite and washed with methylene chloride. The filtrates were evaporated to dryness under reduced pressure and the residue was purified by flash column chromatography to give 0.011 g (55% yield) of pure title compound as a colorless solid; ¹H NMR (CDCl₃) δ 3.89 (s, 6H, OMe); 3.92 (s, 6H, OMe); 4.01 (broad s, 2H, NH₂); 6.95 (d, 1H, CH aromatic, J=8.54 Hz); 7.14 (s, 2H, CH aromatic); 7.46 (d, 1H, CH aromatic, J=8.54 Hz); 8.0 (s, 1H, CH furan).

Example 3

Comparator D

Preparation of 2-Bromo-3-(3,4,5-trimethoxybenzoyl)-6-methoxybenzofuran

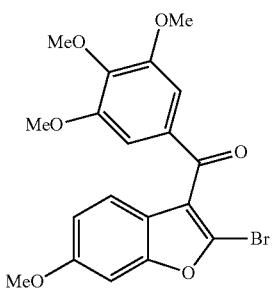

Step 1: tert-Butyldimethylsilyl-3-(t-butyldimethylsilyloxymethylene)-6-methoxybenzofuran (Larock coupling)

A suspension of 2-iodo-5-methoxyphenol (1.1 g, 4.41 mmol), 1-(tert-butyldimethylsilyl)-3-(tert-butyldimethylsilyloxy)propyne (1.5 g, 5.28 mmol), lithium chloride (189 mg, 4.45 mmol) and sodium carbonate (2.34 g, 22.08 mmol) in dry dimethylformamide (5 mL) at 100° C. was deoxygenated 4 times by evacuation and backfilling with nitrogen. Palladium acetate (135 mg, 0.60 mmol) was added and the reaction vessel was degassed twice with nitrogen. The reaction mixture was then stirred at this temperature for 4 hours (monitored by tlc) and the solvent was removed by distillation under vacuum. The residue was dissolved in ethyl acetate (75 mL), stirred well, filtered and treated with triethylamine (5 mL). The solution was concentrated onto silica gel (10 g) and purified by flash chromatography (silica gel, eluent=hexane/diethyl ether/triethylamine; 95:5:1%) to give the title compound as a yellow oil (1.09 g, 87%); ¹H NMR (300 MHz, CDCl₃) δ 7.52 (d, 1H, J=8.57 Hz), 6.97 (d, 1H, J=2.15 Hz), 6.83 (dd, 1H, J=8.54, 2.18 Hz), 4.81 (s, 2H, CH₂), 3.83 (s, 3H, OMe), 0.93 (s, 9H), 0.91 (s, 9H), 0.34 (s, 6H), 0.11 (s, 6H).

Step 2: 2-t-Butyldimethylsilyl-3-formyl-6-methoxybenzofuran

To a solution of 2-t-butyldimethylsilyl-3-(t-butyldimethylsilyloxymethylene)-6-methoxy-benzofuran (1.09 g, 2.69 mmol) in methanol (100 mL) was added concentrated hydrochloric acid (200 µL) and the reaction was stirred for 30 minutes (monitored by tlc), quenched with triethylamine (2 mL) and the solvent removed by distillation under vacuum. The residue was dissolved in dichloromethane (20 mL), washed with water (10 mL), dried over magnesium sulfate, concentrated under vacuum and co-distilled with toluene (20 mL); ¹H NMR (300 MHz, CDCl₃) δ 7.57 (d, 1H, J=8.57 Hz), 7.00 (d, 1H, J=2.17 Hz), 6.86 (dd, 1H, J=8.55, 2.22 Hz), 4.81 (s, 2H, CH₂), 3.84 (s, 3H, OMe), 0.94 (s, 9H), 0.37 (s, 6H). The crude yellow paste (~985 mg) was dissolved in dry dichloromethane (4 mL) and added to a stirred solution of Collin's reagent (chromium trioxide (1.01 g), pyridine (1.65 mL) in dry dichloromethane (30 mL)). The suspension was stirred for 10 minutes, filtered and the residue washed with diethyl ether (20 mL). The filtrate was concentrated onto silica (10 g) and purified by flash chromatography (silica gel, eluent=hexane/diethyl-ether/triethylamine (90:9:1) to afford the title compound as a light yellow oil which crystallized on standing (485 mg, 68%); ¹H NMR (300 MHz, CDCl₃) δ 10.25 (s, 1H, CHO), 8.06 (d, 1H, J=8.61 Hz), 7.03 (d, 1H, J=2.16 Hz), 6.95 (dd, 1H, J=8.60, 2.19 Hz), 3.84 (s, 3H, OMe), 0.97 (s, 9H), 0.46 (s, 6H); ¹³C NMR (75 MHz, CDCl₃) δ 186.91 (CHO), 174.18, 159.19, 159.17, 132.82, 122.77, 117.34, 113.56, 95.36, 55.60, 27.04, 17.09, −5.24.

Step 3: 2-t-Butyldimethylsilyl-3-(3,4,5-trimethoxybenzoyl)-6-methoxy-benzofuran

To a stirred solution of 3,4,5-trimethoxyiodobenzene (377 mg, 1.27 mmol) in dry tetrahydrofuran (1 mL) at −78° C. under nitrogen was added n-butyllithium (795 µL, 1.59 mmol, 2M solution in cyclohexane) and the reaction mixture was stirred at this temperature for 40 minutes. After this time a solution of 2-t-butyldimethylsilyl-3-formyl-6-methoxybenzofuran (310 mg, 1.07 mmol) in dry tetrahydrofuran (1 mL) was added to the reaction dropwise via syringe pipette.

The reaction mixture was stirred at −60° C. for 20 minutes and then allowed to warm to 0° C., stirred for 10 minutes, quenched with saturated ammonium chloride solution (2 mL) and diluted with ethyl acetate (20 mL). The organic layer was washed with water (10 mL), dried over magnesium sulfate and the solvent was removed under vacuum to give a residue that was co-distilled with toluene. The crude product (908 mg) was dissolved in dry tetrahydrofuran (10 mL) and treated with 2,3-dichloro-5,6-dicyano-1,4-benzoquinone (900 mg, 1.59 mmol) was added. The reaction mixture was stirred at room temperature for 16 hours (monitored by tlc) and then loaded onto silica (10 g) and purified by flash chromatography (silica gel, eluent=hexane/diethyl ether/triethylamine, 90:9:1) to afford the title compound as a light yellow paste that crystallised on standing (232 mg, 48%); $^1$H NMR (300 MHz, CDCl$_3$) δ 7.14 (s, 2H, benzoyl Hs), 7.05 (d, 1H, J=2.45 Hz), 6.77 (dd, 1H, J=8.76, 2.17 Hz), 6.56 (d, 1H, J=8.38 Hz), 3.94 (s, 3H, OMe), 3.85 (s, 6H, 2×OMe), 3.78 (s, 3H, OMe), 1.00 (s, 9H), 0.28 (s, 6H); $^{13}$C NMR (75 MHz, CDCl$_3$) δ 190.51 (CO), 164.77, 158.23, 158.12, 152.64, 142.35, 133.19, 131.37, 123.19, 121.04, 119.63, 112.26, 107.03, 104.96, 95.00, 60.47, 55.81, 55.60, 55.13, 26.43, 17.29, −6.09.

Step 4: 2-Bromo-3-(3,4,5-trimethoxybenzoyl)-6-methoxybenzofuran

To a stirred solution of 2-t-butyldimethylsilyl-3-(3,4,5-trimethoxybenzoyl)-6-methoxybenzofuran (200 mg, 0.44 mmol) in 1,2-dichloroethane (2 mL) at 0° C. under nitrogen was added bromine (23 μl, 0.44 mmol) dropwise and the reaction mixture was stirred for 10 minutes. After this time the reaction was quenched with saturated sodium thiosulfate solution, extracted with ethyl acetate (20 mL), dried over magnesium sulfate and the solvent removed by distillation under vacuum. The crude product was re-crystallised from acetonitrile to afford the title compound as a colourless crystalline solid (69 mg, 37%); $^1$H NMR (300 MHz, CDCl$_3$) δ 7.45 (d, 1H, J=8.78 Hz), 7.15 (s, 2H, benzoyl-Hs), 7.01 (d, 1H, J=2.18 Hz), 6.90 (dd, 1H, J=8.74, 2.27 Hz), 3.94 (s, 3H, OMe), 3.85 (s, 9H, 3×OMe); $^{13}$C NMR (75 MHz, CDCl$_3$) δ 188.21 (CO), 158.29, 155.80, 152.72, 142.55, 131.99, 130.69, 120.98, 119.97, 119.67, 112.90, 107.00, 95.30, 60.67, 55.94, 55.43.

Example 4

Preparation of 2-Bromo-7-acetoxy-3-(3,4,5-trimethoxybenzoyl)-6-methoxybenzofuran

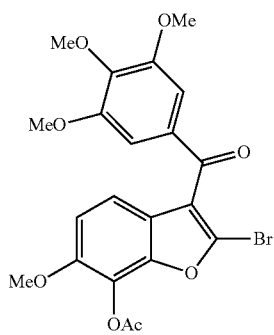 [SMILES: COc1cc(C(=O)c2c(Br)oc3c(OC(C)=O)c(OC)ccc23)cc(OC)c1OC]

Step 1: 2-t-Butyldimethylsilyl-3-(t-butyldimethylsilyloxymethylene)-6-methoxy-7-isopropoxybenzofuran (Larock Coupling)

A suspension of 2-isopropoxy-3-methoxy-5-iodophenol (4.41 mmol), 1-(tert-butyldimethylsilyl)-3-(tert-butyldimethylsilyloxy)propyne (1.5 g, 5.28 mmol), lithium chloride (189 mg, 4.45 mmol) and sodium carbonate (2.34 g, 22.08 mmol) in dry dimethylformamide (5 mL) at 100° C. was deoxygenated 4 times by evacuation and backfilling with nitrogen. Palladium acetate (135 mg, 0.60 mmol) was added and the reaction vessel was degassed twice with nitrogen. The reaction mixture was then stirred at this temperature for 4 hours (tlc) and the solvent was removed by distillation under vacuum. The residue was dissolved in ethyl acetate (75 mL), stirred well, filtered and treated with triethylamine (5 mL). The solution was concentrated onto silica gel (10 g) and purified by flash chromatography (silica gel, eluent=hexane/diethyl ether/triethylamine; 95:5:1%) to afforded the title compound as a yellow oil (1.45 g, 96%); $^1$H NMR (300 MHz, CDCl$_3$) δ 7.24 (d, 1H, J=8.45 Hz), 6.88 (d, 1H, J=8.47 Hz), 4.80 (s, 2H, CH$_2$), 4.73 (m, 1H), 3.88 (s, 3H, OMe), 1.36 (d, 6H, J=6.17 Hz), 0.94 (s, 9H), 0.92 (s, 9H), 0.35 (s, 6H), 0.12 (s, 6H).

Step 2: 2-t-Butyldimethylsilyl-3-formyl-6-methoxy-7-isopropoxybenzofuran

To a solution of 2-t-butyldimethylsilyl-3-(t-butyldimethylsilyloxymethylene)-6-methoxy-7-isopropoxybenzofuran (2.69 mmol) in methanol (100 mL) was added concentrated hydrochloric acid (200 μL) and the reaction was stirred for 30 minutes (monitored by tlc), quenched with triethylamine (2 mL) and the solvent removed by distillation under vacuum. The residue was dissolved in dichloromethane (20 mL), washed with water (10 mL), dried over magnesium sulfate, concentrated under vacuum and co-distilled with toluene (20 mL). The crude product was dissolved in dry dichloromethane (4 mL) and added to a stirred solution of Collin's reagent (chromium trioxide (1.01 g), pyridine (1.65 mL) in dry dichloromethane (30 mL)). The suspension was stirred for 10 minutes, filtered and the residue washed with diethyl ether (20 mL). The filtrate was concentrated onto silica (10 g) and purified by flash chromatography (silica gel, eluent=hexane/diethyl-ether/triethylamine (90:9:1) to afford the title compound as a light yellow oil (503 mg, 48%); $^1$H NMR (300 MHz, CDCl$_3$) δ 10.25 (s, 1H, CHO), 7.79 (d, 1H, J=8.45 Hz), 6.98 (d, 1H, J=8.46 Hz), 4.65 (m, 1H), 3.89 (s, 3H, OMe), 1.35 (d, 6H, J=6.17 Hz), 0.97 (s, 9H), 0.45 (s, 6H).

Step 3: 2-t-Butyldimethylsilyl-3-(3,4,5-trimethoxybenzoyD-6-methoxy-7-isopropoxybenzofuran To a stirred solution of 3,4,5-trimethoxyiodobenzene (377 mg, 1.27 mmol) in dry tetrahydrofuran (1 mL) at −78° C. under nitrogen was added n-butyllithium (795 mL, 1.59 mmol, 2M solution in cyclohexane) and the reaction mixture was stirred at this temperature for 40 minutes. After this time a solution of 2-t-butyldimethylsilyl-3-formyl-6-methoxy-7-isoproxybenzofuran (1.07 mmol) in dry tetrahydrofuran (1 mL) was added to the reaction dropwise via syringe pipette. The reaction mixture was stirred at −60° C. for 20 minutes and then allowed to warm to 0° C., stirred for 10 minutes, quenched with saturated ammonium chloride solution (2 mL) and diluted with ethyl acetate (20 mL). The organic layer was washed with water (10 mL), dried over magnesium sulfate and the solvent was removed under vacuum to give a residue that was co-distilled with toluene. The crude product (908 mg) was dissolved in dry tetrahydrofuran (10 mL) and treated with 2,3-dichloro-5,6-dicyano-1,4-benzoquinone (900 mg, 1.59 mmol) was added. The reaction mixture was stirred at room temperature for 16 hours (monitored by tlc) and then loaded onto silica (10 g) and purified by flash chromatography (silica gel, eluent=hexane/diethyl ether/triethylamine, 90:9:1) to afford the title compound as a light yellow oil (498 mg, 69%); $^1$H NMR (300 MHz, CDCl$_3$) δ 7.14 (s, 2H, benzoyl Hs), 6.81 (d, 1H, J=8.64 Hz), 6.77 (d, 1H, J=8.64 Hz) 4.74 (m, 1H), 3.93 (s, 3H, OMe), 3.86 (s, 3H, OMe), 3.78 (s, 6H, 2×OMe), 1.39 (d, 6H, J=6.14 Hz), 1.01 (s, 9H), 0.26 (s, 6H).

Step 4: 2-(tert-butyldimethylsilyloxy)-7-acetoxy-3-(3,4,5-trimethoxybenzoyl)-6-methoxybenzofuran To a stirred solution of 2-(t-butyldimethylsilyloxy)-7-isopropoxy-3-(3,4,5-trimethoxybenzoyl)-6-methoxy-benzofuran (160 mg, 0.31 mmol) in dry DCM (2 mL) at room temperature under nitrogen was added solid aluminium trichloride (83 mg, 0.62 mmol) and the reaction mixture was stirred for 15 minutes (monitored by tlc). The reaction was quenched with a saturated solution of ammonium chloride, extracted with dichloromethane and dried over magnesium sulfate. The solvent was removed by distillation and residue was dried by azeotropic removal of water with toluene. The crude product was dissolved in pyridine (2 mL), acetic anhydride (1 mL) was added and reaction mixture was stirred for 2 hours at room temperature. The solvent was distilled under vacuum and the residue was loaded onto silica gel (1 g) and purified by column chromatography (silica gel, eluent, hexane:diethyl-ether; 80:20) (134 mg, 84%); $^1$H NMR (300 MHz, CDCl$_3$) δ 7.14 (s, 2H, benzoyl Hs), 6.98 (d, 1H, J=8.72 Hz), 6.85 (d, 1H, J=8.72 Hz), 3.93 (s, 3H, OMe), 3.86 (s, 3H, OMe), 3.80 (s, 6H, 2×OMe), 2.41 (s, 3H), 0.99 (s, 9H), 0.25 (s, 6H).

Step 5: 2-Bromo-7-acetoxy-3-(3,4,5-trimethoxybenzoyl)-6-methoxybenzofuran

To a stirred solution of 2-t-butyldimethylsilyl-7-acetoxy-3-(3,4,5-trimethoxybenzoyl)-6-methoxybenzofuran (120 mg, 0.44 mmol) in 1,2-dichloroethane (1 mL) at room temperature under nitrogen was added bromine (12 μl, 0.44 mmol) dropwise and the reaction mixture was stirred at this temperature for 10 minutes. After this time the reaction was quenched with saturated sodium thiosulfate solution, extracted with ethyl acetate (20 mL), dried over magnesium sulfate and the solvent removed by distillation under vacuum. The crude product was purified by silica gel column chromatography (eluent=Hexane:diethyl ether; 8:2-7:3) to afford the title compound as a colourless crystalline solid (91 mg, 81%); $^1$H NMR (300 MHz, CDCl$_3$) δ 7.40 (d, 1H, J=8.70 Hz), 7.14 (s, 2H, benzoyl-Hs), 6.98 (d, 1H, J=8.75 Hz), 3.94 (s, 3H, OMe), 3.89 (s, 3H, OMe), 3.86 (s, 6H, 2×OMe), 2.43 (s, 3H); $^{13}$C NMR (75 MHz, CDCl$_3$) δ 187.95 (CO), 167.71, 152.75, 149.54, 147.49, 142.59, 131.92, 131.80, 123.91, 121.84, 119.89, 117.72, 109.89, 106.92, 60.69, 56.61, 56.00, 20.09.

Example 5

Comparator C

Preparation of 3-(3,4,5-Trimethoxybenzoyl)-6-methoxy-benzofuran

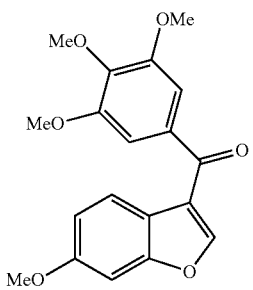 [SMILES: COc1ccc2c(C(=O)c3cc(OC)c(OC)c(OC)c3)coc2c1]

To a stirred solution of 2-t-butyldimethylsilyl-3-(3,4,5-trimethoxy-benzoyl)-6-methoxy-benzofuran (30 mg, 0.066 mmol) in tetrahydrofuran (1 mL) was added tetrabutylammoniumfluoride (76.5 μL, 0.076 mmol, 1M solution in tetrahydrofuran). The reaction mixture was stirred at room temperature for 20 minutes (monitored by tlc), diluted with ethyl acetate (10 mL) and washed with 1M hydrochloric acid (5 mL). The organic layer was dried over magnesium sulfate and the solvent was removed under vacuum. The crude product was purified by flash chromatography (silica gel, eluent=hexane/diethyl ether; 7:3) to afford the title product as a cream crystalline solid (19.3 mg, 86%); $^1$H NMR (300 MHz, CDCl$_3$) δ 8.02 (d, 1H, J=8.97 Hz), 8.01 (s, 1H, C$_2$H), 7.14 (s, 2H, benzoyl Hs), 7.05 (d, 1H, J=2.11 Hz), 7.00 (dd, 1H, J=8.63, 2.11 Hz), 3.93 (s, 3H, OMe), 3.90 (s, 6H, 2×OMe), 3.87 (s, 3H, OMe); $^{13}$C NMR (75 MHz, CDCl$_3$) δ 188.71 (CO), 158.64, 156.31, 152.82, 150.22, 141.72, 133.97, 122.58, 120.87, 118.12, 113.11, 106.07, 95.53, 60.63, 55.99, 55.40.

Example 6

Preparation of 3-(3,4,5-Trimethoxybenzoyl)-6-methoxy-7-hydroxybenzofuran

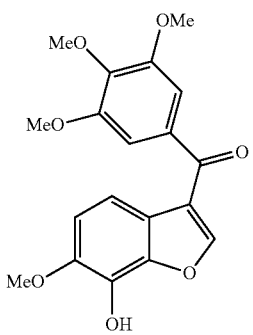 [SMILES: COc1cc(C(=O)c2coc3c(O)c(OC)ccc23)cc(OC)c1OC]

Step 1: 3-(3,4,5-Trimethoxybenzoyl)-6-methoxy-7-isopropoxybenzofuran

To a stirred solution of 2-t-butyldimethylsilyl-3-(3,4,5-trimethoxy-benzoyl)-6-methoxy-7-isopropoxy-benzofuran (0.066 mmol) in tetrahydrofuran (1 mL) was added tetrabutylammoniumfluoride (76.5 µl, 0.076 mmol, 1M solution in tetrahydrofuran). The reaction mixture was stirred at room temperature for 20 minutes (monitored by tlc), diluted with ethyl acetate (10 mL) and washed with 1M hydrochloric acid (5 mL). The organic layer was dried over magnesium sulfate and the solvent was removed under vacuum. The crude product was purified by flash chromatography (silica gel, eluent=hexane/diethyl ether; 7:3) to afford the title compound as a light yellow paste (23 mg) that was used directly in the next step; $^1$H NMR (300 MHz, CDCl$_3$) δ 8.00 (s, 1H, C$_2$H), 7.78 (d, 1H, J=8.60 Hz), 7.15 (s, 2H, benzoyl Hs), 7.04 (d, 1H, J=8.61 Hz), 4.73 (m, 1H), 3.93 (s, 3H, OMe), 3.92 (s, 3H, OMe), 3.90 (s, 6H, 2×OMe), 1.37 (d, 6H, J=6.14 Hz).

Step 2: 3-(3,4,5-Trimethoxybenzoyl)-6-methoxy-7-hydroxybenzofuran

A solution of 3-(3,4,5-trimethoxybenzoyl)-6-methoxy-7-isopropoxybenzofuran (23 mg, 0.058 mmol, co-distilled with toluene before use) in dry dichloromethane (1 mL) was treated with solid aluminum chloride (16 mg, 0.116 mmol). The reaction mixture was stirred for 20 minutes at room temperature (monitored by tlc) then quenched with saturated ammonium chloride solution and extracted with ethyl acetate (10 mL). The organic layer was washed with water (5 mL), dried over magnesium sulfate and concentrated under vacuum. The crude product was purified by flash chromatography (silica gel, eluent=hexane/diethyl ether/ethyl acetate; 80:19:1) to afford the title compound as a creamy white crystalline solid (18 mg, 86%); $^1$H NMR (300 MHz, CDCl$_3$) δ 8.04 (s, 1H, C$_2$H), 7.63 (d, 1H, J=8.53 Hz), 7.14 (s, 2H, benzoyl Hs), 7.02 (d, 1H, J=8.38 Hz), 3.97 (s, 3H, OMe), 3.93 (s, 3H, OMe), 3.89 (s, 6H, 2×OMe); $^{13}$C NMR (75 MHz, CDCl$_3$) δ 188.73 (CO), 152.82, 151.24, 144.54, 143.30, 141.76, 133.97, 130.87, 120.92, 120.62, 112.43, 109.16, 106.06, 60.62, 56.85, 55.97.

Example 7

Alternative Synthesis of 2-t-Butyldimethylsilyl-3-(3,4,5-trimethoxybenzoyl)-6-methoxy-7-isopropoxy-benzofuran

Step 1: 3-(tert-Butyldimethylsilyl)-1-(3,4,5-trimethoxyphenyl)propynone

N-Butyl-lithium (1.7 M in THF, 8.12 mL, 13.8 mmol) was added dropwise to a stirred solution of t-butyl-dimethyl-silyl-acetylene (2.5 mL, 13.39 mmol) in dry THF (10 mL) at −78° C. under nitrogen and the reaction mixture was stirred at between −78 to −60° C. for 1 hour. Solution of 3,4,5-trimethoxy-benzaldehyde (2.7 g, 13.8 mmol) in dry THF (5 mL) was added to the above stirred solution dropwise and stirring was continued for 20 minutes. The reaction was warmed to room temperature and stirred for one hour (monitored by tlc), quenched with saturated ammonium chloride solution and diluted with ethylacetate (100 mL). The organic layer was separated, dried over magnesium sulfate and the solvent was distilled and co-distilled with toluene to afford the crude product as creamy paste (4.47 g). The above product was dissolved in dry dichloromethane (200 mL), MnO$_2$ (2.5 g, 28.75 mmol) was added and the suspension was stirred for overnight (monitored by tlc). Reaction was filtered through celite, washed with dichloromethane (50 mL) and solvent was distilled to afford the crude product as creamy paste (4.16 g, 93%); $^1$H NMR (300 MHz, CDCl$_3$) δ 7.41 (s, 2H, benzoyl Hs), 3.89 (s, 3H, OMe), 3.87 (s, 6H, 2×OMe), 0.99 (s, 9H), 0.21 (s, 6H).

Step 2: 2-t-Butyldimethylsilanyl-3(3,4,5-trimethoxybenzoyl)-6-methoxy-7-isopropoxy-benzofuran Procedure similar to Larock coupling described above; (3.96 g, 60%), see above in Example 6 for spectral data.

Example 8

Preparation of 2-Ethynyl-7-hydroxy-6-methoxy-3-(3,4,5-trimethoxybenzoyl)-benzofuran

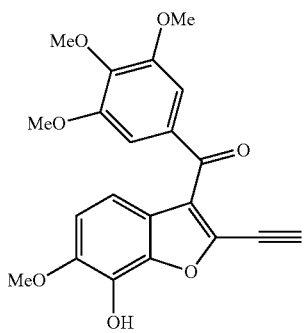 [SMILES: C#Cc1oc2c(O)c(OC)ccc2c1C(=O)c1cc(OC)c(OC)c(OC)c1]

To a stirred solution of 2-Bromo-7-acetoxy-3-(3,4,5-trimethoxybenzoyl)-6-methoxybenzofuran (50 mg, 0.10 mmol) in dichloromethane (1 ml) and triethylamine (0.5 ml) was added Pd(Ph$_3$P)$_2$Cl$_2$ (3.5 mg, 5 mol %) and the reaction vessel was evacuated and backfilled with nitrogen three times. Trimethylsilylacetylene (30 mg, 0.30 mmol) and copper (I) iodide (3 mg, 15 mol %) were added sequentially and the resulting dark mixture was stirred for two hours at room temperature. After this time the reaction was concentrated under vacuum and treated with methanol (1 ml) and potassium hydroxide (30 mg, excess). Stirring was continued for 0.5 hours then the crude mixture was concentrated onto silica and chromatographed (silica gel, gradient elution—2:1 hexanes:ethyl acetate, 1:1 hexanes:ethyl acetate) to afford the product as a tan solid (10 mg, 26%); $^1$H NMR (CDCl$_3$) δ 7.26 (d, J=8.6 Hz, 1H), 7.20 (s, 2H), 6.98 (d, J=8.6 Hz, 1H), 3.96 (s, 3H), 3.93 (s, 3H), 3.87 (s, 6H), 3.51 (s, 1H); LRMS (ESI) m/z=383 (M+H$^+$).

Example 9

Preparation of 7-Hydroxy-6-methoxy-2-methylsulfanyl-3-(3,4,5-trimethoxybenzoyl)benzofuran

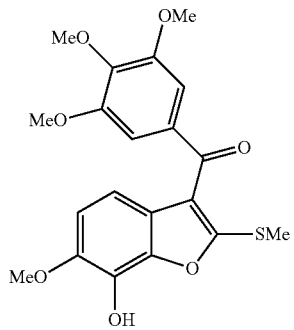 [SMILES: COc1cc(C(=O)c2c(SC)oc3c(O)c(OC)ccc23)cc(OC)c1OC]

To a suspension of 2-Bromo-7-acetoxy-3-(3,4,5-trimethoxybenzoyl)-6-methoxybenzofuran (22 mg, 0.046 mmol) in methanol (1 ml) in a screw cap vial was added sodium thiomethoxide (16 mg, 0.23 mmol) and the resulting orange solution was shaken for 20 minutes during which time the reaction became homogeneous. The crude reaction mixture was concentrated onto silica and chromatographed (silica gel, eluent=2:1 hexanes:ethyl acetate) to give the product as a resin (10 mg, 54%) that could be crystallised by standing in hexanes in the freezer overnight; $^1$H NMR (CDCl$_3$) δ 7.08 (s, 2H), 6.92 (d, J=8.3 Hz, 1H), 6.82 (d, J=8.3 Hz, 1H), 5.73 (br s, 1H), 3.93 (s, 3H), 3.92 (s, 3H), 3.84 (s, 6H), 2.66 (s, 3H).

Example 10

Preparation of 2-Hydrazino-7-hydroxy-6-methoxy-3-(3,4,5-trimethoxybenzoyl)-benzofuran

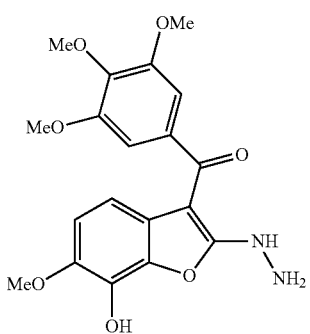 [SMILES: COc1cc(C(=O)c2c(NN)oc3c(O)c(OC)ccc23)cc(OC)c1OC]

To a solution of the 2-Bromo-7-acetoxy-3-(3,4,5-trimethoxybenzoyl)-6-methoxybenzofuran (30 mg, 0.062 mmol) in tetrahydrofuran (0.5 ml) was added hydrazine monohydrate (15 mL, 0.3 mmol). A yellow precipitate immediately formed and the heterogeneous mixture was heated to 60° C. for 1 hour during which time more solid separated from the reaction. After cooling, the solid product was collected by filtration, washed with ether and dried under vacuum (6 mg, 25%); $^1$H NMR (d$^6$-DMSO) δ 9.70 (br s, 1H), 9.27 (br s, 1H), 6.85 (s, 2H), 6.68 (d, J=8.5 Hz, 1H), 6.21 (d, J=8.5 Hz, 1H), 5.00 (br s, 2H), 3.73 (s, 6H), 3.71 (s, 3H), 3.70 (s, 3H).
LRMS (ESI) m/z=389 (M+H$^+$), 372 (M+H$^+$−NH$_3$).

Example 11

Preparation of 2-Methyl-7-hydroxy-3-(3,4,5-trimethoxybenzoyl)-6-methoxybenzofuran

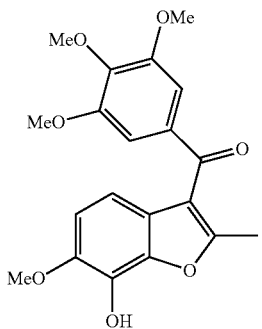

To a stirred solution of 2-Bromo-7-acetoxy-3-(3,4,5-trimethoxybenzoyl)-6-methoxybenzofuran (20 mg, 0.042 mmol), methyl-boronic acid (40 mg, 0.67 mmol), in 1,4-dioxane (2 mL) at 90° C. was added tetrakis-triphenylphosphine palladium (11 mg, 0.01 mmol) followed by the addition of a solution of sodium bicarbonate (40 mg, 0.48 mmol) in distilled water (0.5 mL). The reaction mixture turned red after 5 minutes. After 2 hours (tlc) the reaction mixture was brought to room temperature and was added saturated ammonium chloride (2 mL) and diluted with dichloromethane (20 mL). The organic layer was separated and washed with water, dried over magnesium sulfate and the solvent was removed by distillation under vacuum. The residue was purified by PTLC (eluent=Dichloromethane/Methanol, 1:1) to give the title compound (actate cleaved during reaction) as a fluffy white solid; (3 mg, 19%).

Example 12

Alternative Method for preparing 2-Methyl-7-hydroxy-3-(3,4,5-trimethoxybenzoyl)-6-methoxybenzofuran (Negishi Coupling)

To a stirred solution of zinc-bromide (592 mg, 2.63 mmol) in dry THF (1.5 mL) at 0° C. was added the solution of methyl lithium (1.6 M solution in diethyl-ether, 2.6 mL, 4.15 mmol) and the reaction mixture was stirred for 2 hours. Solid 2-bromo-7-acetoxy-3-(3,4,5-trimethoxybenzoyl)-6-methoxy-benzofuran (300 mg, 0.63 mmol) (compound of example 4) was added and the ether was removed under vacuum and to the rest suspension was added dichlorobis(triphenylphosphine)palladium catalyst (21 mg) and catalytic amount of copper (I) iodide. The reaction mixture was stirred at room temperature for 36 hours (monitored by tlc), quenched with saturated ammonium chloride solution and extracted with dichloromethane (10 mL), dried over magnesium sulfate and solvent distilled under vacuum and the product was purified by silica gel column (eluent=hexane/ethyl acetate; 8:2). The product was crystallized in methanol (106 mg, 46%); $^1$H NMR (300 MHz, CDCl$_3$) δ 7.09 (s, 2H, benzoyl Hs), 6.93 (d, 1H, J=8.54 Hz), 6.83 (d, 1H, J=8.56 Hz), 5.70 (bs, 1H, OH), 3.93 (s, 3H, OMe), 3.92 (s, 3H, OMe), 3.83 (s, 6H, 2×OMe), 2.54 (s, 3H, 2-Me)

Example 13

Preparation of [7-Hydroxy-6-methoxy-2-{(E)-pent-1-enyl)benzofuran-3-yl]-3,4,5-trimethoxy-phenyl)methanone

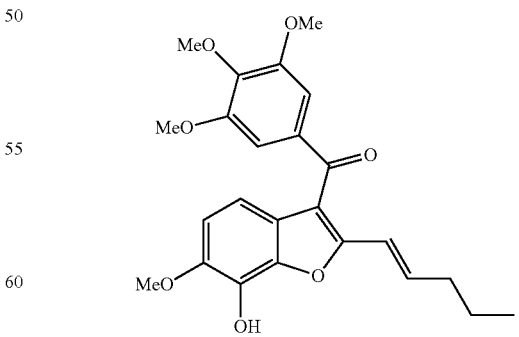

As for the Suzuki reaction above (see Example 11), except the methylboronic acid was replaced with trans-4,4,5,5-tetramethyl-2-pent-1-enyl-1,3,2-dioxaborolane the identical procedure afforded the title compound as light creamy solid (24 mg, 27%); $^1$H NMR (300 MHz, CDCl$_3$) δ 7.12 (s, 2H, benzoyl Hs), 6.97 (d, 1H, J=8.55 Hz), 6.83 (d, 1H, J=8.61 Hz), 6.87-6.78 (m, 1H), 6.45 (and 1H, J=14.44 Hz), 5.68 (b, 1H, OH), 3.93 (s, 6H, 2×OMe), 3.83 (s, 6H, 2×OMe), 2.2-2.15 (m, 2H), 1.50-1.41 (m, 2H), 0.92 (t, 3H, J=7.41 Hz).

Example 14

Preparation of (E)-3-[7-Hydroxy-6-methoxy-3-(3,4,5-trimethoxy-benzoyl)-benzofuran-2-yl]-acrylic acid methyl ester

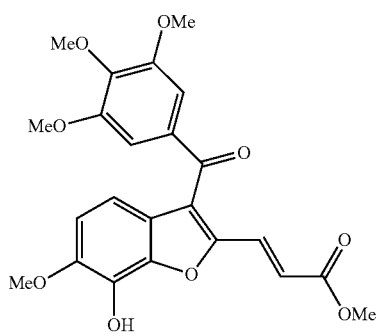 [SMILES: COC(=O)/C=C/c1oc2c(O)c(OC)ccc2c1C(=O)c1cc(OC)c(OC)c(OC)c1]

Mixture of 2-bromo-7-acetoxy-3-(3,4,5-trimethoxybenzoyl)-6-methoxy-benzofuran (50 mg, 0.10 mmol) and methylacrylate (0.5 mL, excess) in a mixture of acetonitrile: TEA; 1 mL:0.5 mL was degassed with nitrogen and palladium acetate (10 mg) was added to it. Reaction mixture was stirred for one hour under nitrogen at reflux, more palladium acetate (15 mg) was added and the refluxing was continued for 7 hours (monitored by tlc). Methanol (1 mL) was added followed by the addition of potassium carbonate (70 mg, 0.51 mmol) and stirring was continued for 1 hour. Solvent was distilled and the crude material was purified over silica gel column (eluent Hexane:diethylether; 1:1) to afford the title compound as yellow crystalline solid (17 mg, 37%); $^1$H NMR (300 MHz, CDCl$_3$) δ 7.61 (d, 1H, J=15.76 Hz), 7.14 (s, 2H, benzoyl Hs), 6.98 (d, 1H, J=8.64 Hz), 6.89 (d, 1H, J=8.69 Hz), 6.81 (d, 1H, J=15.78 Hz), 3.96 (s, 3H, OMe), 3.95 (s, 3H, OMe), 3.81 (s, 6H, 2×OMe), 3.77 (bs, 3H, OMe).

Example 15

Preparation of (E)-3-[7-Hydroxy-6-methoxy-3-(3,4,5-trimethoxy-benzoyl)benzofuran-2-yl]-acrylamide

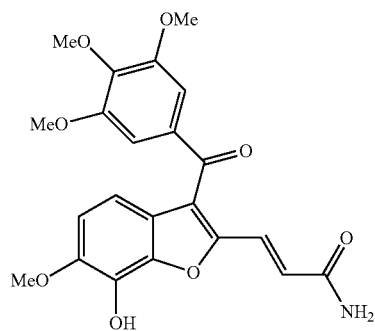 [SMILES: COc1cc(C(=O)c2c(/C=C/C(N)=O)oc3c(O)c(OC)ccc23)cc(OC)c1OC]

As for Example 14 above except methyl acrylate was substituted with acrylamide, gave the title compound as light yellow solid (5 mg, 17%); $^1$H NMR (300 MHz, CD$_3$OD) δ: 7.48 (d, 1H, J=15.5 Hz), 7.18 (s, 2H, benzoyl Hs), 7.00 (d, 1H, J=8.65 Hz), 6.94 (d, 1H, J=15.52 Hz), 6.88 (d, 1H, J=8.62 Hz), 4.55 (b, 2H, NH$_2$), 3.91 (s, 3H, OMe), 3.87 (s, 3H, OMe), 3.79 (s, 6H, 2×OMe).

Example 16

Preparation of 2-cyano-7-acetoxy-3-(3,4,5-trimethoxybenzoyl)-6-methoxy-benzofuran

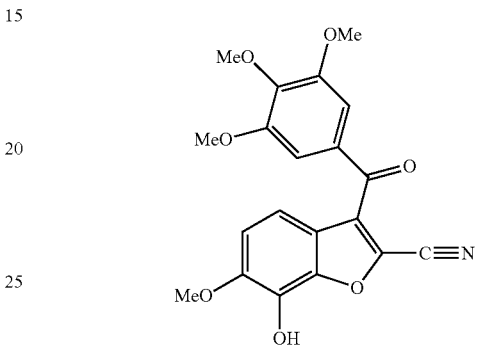

A mixture of 2-bromo-7-acetoxy-3-(3,4,5-trimethoxybenzoyl)-6-methoxybenzofuran (25 mg, 0.05 mmol) and sodium cyanide (15 mg, 0.38 mmol) in dry DMSO (1 mL) under nitrogen at room temperature was stirred for 3.5 hours (monitored by tlc), quenched with saturated ammonium chloride solution and diluted with ethylacetate (20 mL). The organic layer was separated, dried over magnesium sulfate and the solvent distilled to afford the crude material which was purified over silica gel column (eluent-Hexane: diethyl-ether 1:1 to 0:100) to afford the desired product as pale cream solid (13 mg, 65%); $^1$H NMR (300 MHz, CDCl$_3$) δ: 7.29 (d, 1H, J=8.71 Hz), 7.19 (s, 2H, benzoyl Hs), 6.06 (d, 1H, J=8.77 Hz), 5.82 (b, 1H, OH), 3.99 (s, 3H, OMe), 3.96 (s, 3H, OMe), 3.88 (s, 6H, 2×OMe).

Example 17

Preparation of 7-Hydroxy-6-methoxy-3-(3,4,5-trimethoxy-benzoyl)-benzofuran-2-methylcarboxylate

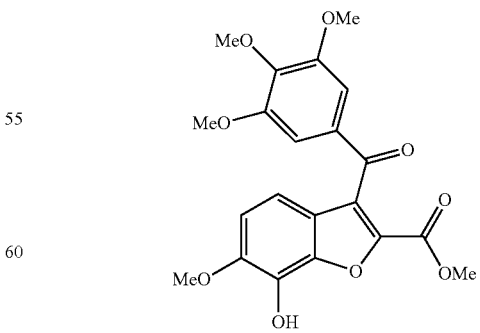

To a solution of 2-cyano-7-acetoxy-3-(3,4,5-trimethoxybenzoyl)-6-methoxy-benzofuran (20 mg, 0.05 mmol) in a mixture of methanol:acetonitrile; 2 mL: 1 mL was added potassium carbonate (50 mg, 0.36 mmol) and the reaction mixture was stirred for 16 hours at room temperature (monitored by tlc). Solvent was distilled and to the residue was added saturated ammonium chloride solution (2 mL) and ethyl acetate (15 mL) and the crude mixture was stirred for 15 minutes. The organic layer was separated and dried over magnesium sulfate. The crude material was purified over silica gel column (eluent-neat diethyl-ether to diethyl-ether:ethyl-acetate 80:20) to afford the title compound as pale cream solid (9 mg, 42%); $^1$H NMR (300 MHz, CDCl$_3$) δ: 7.12 (s, 2H, benzoyl Hs), 6.99 (d, 1H, J=8.57 Hz), 6.93 (d, 1H, J=8.72 Hz), 5.28 (b, 1H, OH), 3.96 (s, 3H, OMe), 3.93 (s, 3H, OMe), 3.81 (s, 6H, 2×OMe), 3.68 (bs, 3H, OMe).

Example 18

Preparation of 2-(N-Methylamino)-7-hydroxy-3-(3,4,5-trimethoxybenzoyl)-6-methoxy-benzofuran

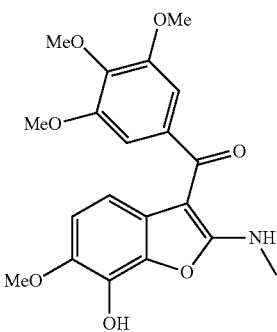 [SMILES: CNc1oc2c(O)c(OC)ccc2c1C(=O)c1cc(OC)c(OC)c(OC)c1]

To a stirred solution of 2-bromo-7-acetoxy-3-(3,4,5-trimethoxybenzoyl)-6-methoxy-benzofuran (20 mg, 0.066 mmol) in acetonitrile (3 mL) was added the solution of methyamine (1 mL, excess as reactant and base), and the reaction mixture was stirred at room temperature for 1 hour when the precipitates appeared. The solvent was distilled under vacuo and the crude was dissolved in tetrahydrofuran (2 mL), 1M hydrochloric acid (1 mL) was added and the reaction mixture was stirred for 1 hour then diluted with dichloromethane (10 mL) and washed with water. The organic layer was dried over magnesium sulfate and solvent was distilled under vacuo. The crude was purified by PTLC (eluent=Hexane:ethylacetate:triethylamine; 2:8:1%) to gave the title compound as a yellow-green solid (5 mg, 29%); $^1$H NMR (300 MHz, CDCl$_3$) δ 8.91 (broad, 1H, NH), 6.93 (s, 2H, benzoyl Hs), 6.59 (d, 1H, J=8.56 Hz), 6.46 (d, 1H, J=8.51 Hz), 5.61 (bs, 1H, OH), 3.91 (s, 3H, OMe), 3.86 (s, 3H, OMe), 3.84 (s, 6H, 2×OMe), 3.28 (d, 3H, J=5.28 Hz).

Example 19

Preparation of (2-Amino-7-hydroxy-6-methoxy-benzofuran-3-yl)-(3,4,5-trimethoxyphenyl)-methanone

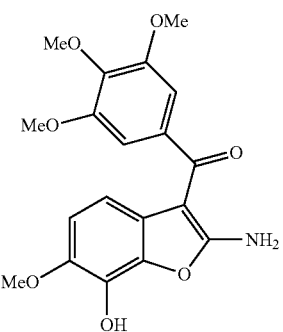

Step 1: (2-Benzylamino-7-hydroxy-6-methoxy-benzofuran-3-yl)-(3,4,5-trimethoxy-phenyl)-methanone 2-bromo-7-acetoxy-3-(3,4,5-trimethoxybenzoyl)-6-methoxy-benzofuran (140 mg, 0.29 mmol) was dissolved in dry pyridine (2 mL) and benzylamine (500 µL, excess) was added to it and the reaction mixture was stirred at 80° C. for 1 hour. Solvent was distilled and the crude product was purified over silica gel column to afford the title compound as light yellow solid (112 mg, 83%); $^1$H NMR (300 MHz, CDCl$_3$) δ: 9.27 (b, 1H, NH), 7.39-7.32 (m, 5 Hs, Ar Hs), 6.96 (s, 2H, benzoyl Hs), 6.61 (d, 1H, J=8.47 Hz), 6.50 (d, 1H, J=8.10 Hz), 4.83 (d, 2H, J=4.95 Hz, Benzyl Hs), 3.91 (s, 3H, OMe), 3.85 (s, 3H, OMe), 3.84 (s, 6H, 2×OMe).

Step 2: (2-Amino-7-hydroxy-6-methoxy-benzofuran-3-yl)-(3,4,5-trimethoxy-phenyl)methanone A mixture of 2-benzylamino-7-hydroxy-6-methoxy-benzofuran-3-yl)-(3,4,5-trimethoxy-phenyl)-methanone (105 mg, 0.23 mmol) and Pd/C (10%, 100 mg) in a mixture of solvents ethylacetate/THF/water/HCl (3 mL:2 mL:1 mL) 2 drops was stirred at room temperature for 2.5 hours under the atmosphere of hydrogen (monitored by tlc). The mixture was filtered through celite, washed with dichloromethane (5 mL×3) and solvent was distilled to afford the product as green yellow solid which was purified by flash column to gave the crystalline yellow green solid (79 mg, 93%); $^1$H NMR (300 MHz, CDCl$_3$) δ: 6.98 (s, 2H, benzoyl Hs), 6.93 (bs, 2H, NH2), 6.63 (d, 1H, J=8.18 Hz), 6.52 (d, 1H, J=8.41 Hz), 5.65 (bs, 1H, OH), 3.92 (s, 3H, OMe), 3.86 (s, 3H, OMe), 3.84 (s, 6H, 2×OMe).

Example 20

Preparation of [7-Hydroxy-2-(2-hydroxy-ethylamino)-6-methoxy-benzofuran-3-yl]-(3,4,5-trimethoxy-phenyl)methanone

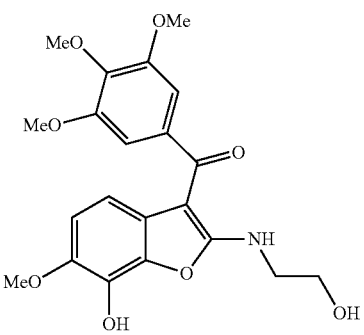 [SMILES: COc1cc(C(=O)c2c(NCCO)oc3c(O)c(OC)ccc23)cc(OC)c1OC]

When benzylamine was substituted with ethanolamine as in Example 19 (see step 1) the same procedure gave the title compound as greenish yellow solid (29 mg, 67%); $^1$H NMR (300 MHz, CDCl$_3$) δ: 9.13 (b, 1H, NH), 6.94 (s, 2H, benzoyl Hs), 6.60 (d, 1H, J=8.54 Hz), 6.47 (d, 1H, J=8.55 Hz), 3.94-3.89 (m, 4H), 3.91 (s, 3H, OMe), 3.85 (s, 3H, OMe), 3.83 (s, 6H, 2×OMe).

Example 21

Preparation of [2-(2-Dimethylamino-ethylamino)-7-hydroxy-6-methoxy-benzofuran-3-yl-(3,4,5-trimethoxy-phenyl)methanone

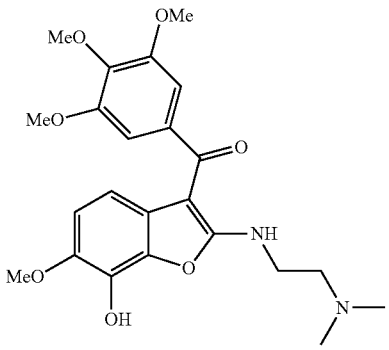 [SMILES: COc1cc(C(=O)c2c(NCCN(C)C)oc3c(O)c(OC)ccc23)cc(OC)c1OC]

When benzylamine was substituted with N,N'-dimethyl-ethylenediamine as in Example 20 (see step 1) the same procedure gave the title compound as greenish yellow solid (25 mg, 54%); $^1$H NMR (300 MHz, CDCl$_3$) δ 9.1 (b, 1H, NH), 6.95 (s, 2H, benzoyl Hs), 6.60 (d, 1H, J=8.44 Hz), 6.48 (d, 1H, J=8.48 Hz), 3.90 (s, 3H, OMe), 3.84 (s, 3H, OMe), 3.83 (s, 6H, 2×OMe), 3.82-3.83 (m, 2H), 2.65 (t, 2H, J=5.63 Hz), 2.34 (s, 6H).

Example 22

Preparation of (2-N,N'-Dimethylamino-7-hydroxy-6-methoxy-benzofuran-3-yl)-(3,4,5-trimethoxy-phenyl)-methanone

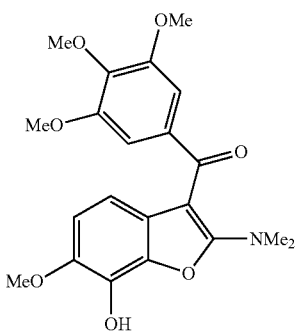 [SMILES: COc1cc(C(=O)c2c(N(C)C)oc3c(O)c(OC)ccc23)cc(OC)c1OC]

The 2-bromo-7-acetoxy-3-(3,4,5-trimethoxybenzoyl)-6-methoxy-benzofuran (40 mg, 0.084 mmol) was dissolved in THF (1 mL) and solution of N,N'-dimethyl-amine (2M solution in THF, 0.5 mL) was added to it. The reaction mixture was stirred for overnight. Solvent was distilled and the crude was purified over silica gel plate to afford the title compound as yellow solid (18 mg, 54%); $^1$H NMR (300 MHz, CDCl$_3$) δ 7.11 (s, 2H, benzoyl Hs), 6.61 (d, 1H, J=8.55 Hz), 6.44 (d, 1H, J=8.51 Hz), 3.91 (s, 3H, OMe), 3.86 (s, 3H, OMe), 3.84 (s, 6H, 2×OMe).

Example 23

Preparation of [7-hydroxy-6-methoxy-3(3,4,5-trimethoxy-benzoyl)-benzofuran-2-ylamino]-acetic acid

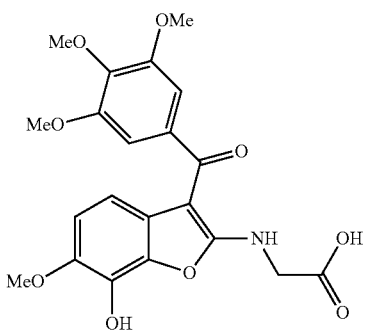 [SMILES: COc1cc(C(=O)c2c(NCC(=O)O)oc3c(O)c(OC)ccc23)cc(OC)c1OC]

A mixture of 2-bromo-7-acetoxy-3-(3,4,5-trimethoxybenzoyl)-6-methoxy-benzofuran (50 mg, 0.10 mmol), glycine (18 mg, 0.29 mmol) and potassium carbonate (29 mg, 0.21 mmol) in a mixture of MeCN/water 80:20 (5 mL) was refluxed for six hours. Solvent was distilled and the residue was taken in water:dichloromethane 1:2 (30 mL) and stirred for 20 minutes. Aqueous layer was separated, washed with dichloromethane (20 mL) and acidified with 2 drops of concentrated HCl and was diluted with dichloromethane (50 mL) and was stirred for 30 minutes. The organic layer was separated and dried over magnesium sulfate and solvent was distilled to afford the title compound as yellow powder (23 mg, 51%); $^1$H NMR (300 MHz, Acetone d$_6$) δ 9.09 (b, 1H, NH), 6.97 (s, 2H, benzoyl Hs), 6.74 (d, 1H, J=8.53 Hz), 6.45 (d, 1H, J=8.48 Hz), 4.48 (d, 2H, J=4.28 Hz), 3.82 (s, 6H, 2×OMe), 3.79 (s, 3H, OMe), 3.78 (s, 3H, OMe).

Example 24

Preparation of [7-Hydroxy-6-methoxy-3-(3,4,5-trimethoxy-benzoyl)-benzofuran-2-ylamino]-acetic acid methyl ester

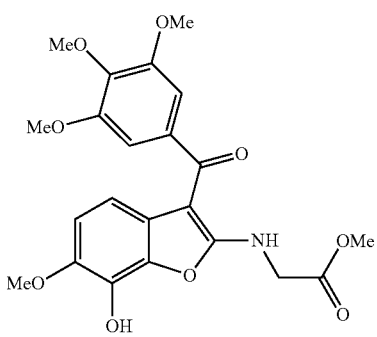 [SMILES: COC(=O)CNc1oc2c(O)c(OC)ccc2c1C(=O)c1cc(OC)c(OC)c(OC)c1]

[7-hydroxy-6-methoxy-3-(3,4,5-trimethoxy-benzoyl)-benzofuran-2-ylamino]acetic acid (30 mg, 0.07 mmol) was dissolved in dry methanol (5 mL) and trimethylsilyl chloride (100 μL) was added to it. The reaction was stirred at room temperature for 6 hours (monitored by tlc). Solvent was distilled under vacuum and the crude was purified over silica gel plate to afford the title compound as yellow solid (23 mg, 79%); $^1$H NMR (300 MHz, CDCl$_3$) δ 9.11 (b, 1H, NH), 6.97 (s, 2H, benzoyl Hs), 6.62 (d, 1H, J=8.56 Hz), 6.51 (d, 1H, J=8.49 Hz), 4.42 (d, 1H, J=6.09 Hz), 3.91 (s, 3H, OMe), 3.86 (s, 3H, OMe), 3.84 (s, 6H, 2×OMe), 3.81 (s, 3H, OMe).

Example 25

Preparation of [7-Hydroxy-6-methoxy-2-(pyridin-3-ylamino)-benzofuran-3-yl]-(3,4,5-trimethoxy-phenyl)-methanone

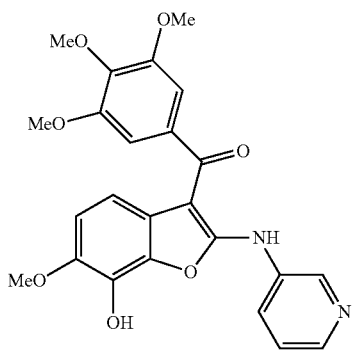 [SMILES: COc1cc(C(=O)c2c(Nc3cccnc3)oc3c(O)c(OC)ccc23)cc(OC)c1OC]

A mixture of 2-bromo-7-acetoxy-3-(3,4,5-trimethoxybenzoyl)-6-methoxy-benzofuran (50 mg, 0.10 mmol) and 3-amino-pyridine (30 mg, 0.30 mmol) in a mixture of solvent acetonitrile:water (8:2, 5 mL) was refluxed with stirring for 6 hours. The solvent was distilled under vacuum and the residue was purified over silica gel column to afford the title compound as yellow solid (11 mg, 23%); $^1$H NMR (300 MHz, CDCl$_3$) δ 11.22 (s, 1H), 8.77 (b, 1H), 8.42 (b, 1H), 8.01 (bd, 1H), 7.28 (b, 1H), 7.03 (s, 2H, benzoyl Hs), 6.71 (d, 1H, J=8.82 Hz), 6.63 (d, 1H, J=8.37 Hz), 3.94 (s, 3H, OMe), 3.90 (s, 3H, OMe), 3.86 (s, 6H, 2×OMe).

Example 26

Preparation of tert-Butyl-2-(7-hydroxy-6-methoxy-3-(3,4,5-trimethoxybenzoyl)benzofuran-2-ylamino) ethyl carbamate

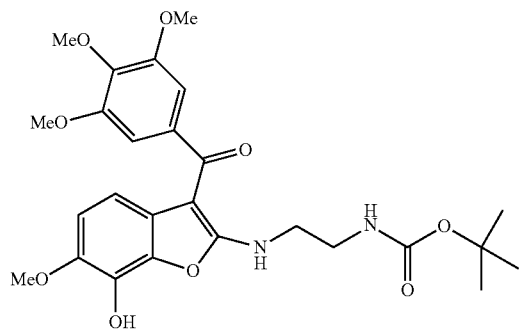 [SMILES: COc1cc(C(=O)c2c(NCCNC(=O)OC(C)(C)C)oc3c(O)c(OC)ccc23)cc(OC)c1OC]

A mixture of 0.05 g (0.1 mmol) of 2-bromo-6-methoxy-3-(3,4,5-trimethoxybenzoyl)-benzofuran-7-yl acetate and 0.057 g (0.35 mmol) of tert-butyl 2-aminoethylcarbamate (Fontand & Pignatti J. Label. Compd. Radiopharm., 2002, 45, 899-909) in 0.5 ml of anhydrous pyridine was stirred overnight at room temperature under nitrogen atmosphere. After evaporation of solvent in vacuo, the residue was diluted to 10 ml with ethyl acetate and washed with saturated ammonium chloride, water and dried over anhydrous magnesium sulfate. Filtration and evaporation of solvent gave 0.054 g of residue, which was purified by flash column chromatography to give the title compound as a creamy solid (0.031 g, 59%); $^1$H NMR (CDCl$_3$) δ 1.42 (s, 9H, Me BOC); 3.45 (m, 2H, CH$_2$); 3.75 (m, 2H, CH$_2$); 3.84 (s, 6H, OMe); 3.86 (s, 3H, OMe); 3.91 (s, 3H, OMe); 4.86 (broad s, 1H, NH); 5.76 (broad s, 1H, OH); 6.47 (d, 1H, CH aromatic, J=8.52 Hz); 6.6 (d, 1H, CH aromatic, J=8.52 Hz); 6.94 (s, 2H, CH aromatic); 9.04 (m, 1H, NH).

Example 27

Preparation of [2-(2-aminoethylamino)-7-hydroxy-6-methoxybenzofuran-3-yl](3,4,5-trimethoxyphenyl) methanone Trifluoroacetate Salt

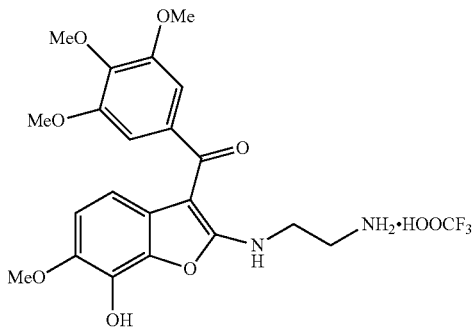

0.026 g (0.05 mmol) of [2-(2-aminoethylamino)-7-hydroxy-6-methoxybenzofuran-3-yl](3,4,5-trimethoxyphenyl) methanone was dissolved in 1 ml of anhydrous trifluoroacetic acid. After stirring for 1 h at room temperature the solvent was removed under reduced pressure and the residue was suspended in 2 ml of anhydrous methylene chloride and evaporated under reduced pressure. The residue was washed with 2 ml of anhydrous methylene chloride to give the title compound as a yellowish solid (0.011 g, 42%); $^1$H NMR (CD$_3$OD) δ 3.31 (tr, 2H, CH$_2$, J=%0.84 Hz); 3.8 (s, 9H, OMe); 3.83 (s, 3H, OMe); 3.92 (tr, 2H, CH, J=5.84 Hz); 6.33 (d, 1H CH aromatic, J=8.52 Hz); 6.69 (d, 1H, CH aromatic, J=8.52 Hz); 6.95 (s, 2H, CH aromatic).

Example 28

Preparation of 1-[2-(7-hydroxy-6-methoxy-3-(3,4,5-trimethoxybenzoyl)benzofuran-2-ylamino)ethyl] guanidine

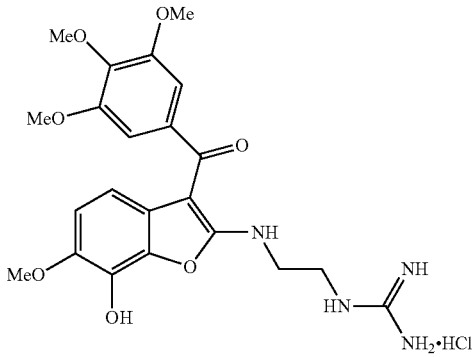

To a mixture of 0.02 g (0.046 mmol) of 2-bromo-7-acetoxy-3-(3,4,5-trimethoxybenzoyl)-6-methoxybenzofuran and 0.02 g (0.11 mmol) of N-(2-aminoethyl)guanidine dihydrochloride (prepared by Fontand & Pignatti, *J. Label. Compd. Radiopharm.*, 2002, 45, 899-909) in 0.5 ml of anhydrous dimethylacetamide 0.032 ml (0.184 mmol) of N,N-diisopropylethylamine was added at room temperature under nitrogen atmosphere. The resulting mixture was stirred for 30 h at room temperature, then evaporated to dryness in vacuo. The residue was purified by flash column chromatography (silica gel, acetonitrile/water 9:1) to give the title compound as a yellowish solid (0.006 g, 28%); $^1$H NMR (CD$_3$OD) δ 3.55 (tr, 2H, CH$_2$, J=6 Hz); 3.7-3.86 (m, 14H, OMe×4, CH$_2$); 4.82 (s, H$_2$O); 6.32 (d, 1H, CH aromatic, J=8.47 Hz); 6.69 (d, 1H, CH aromatic, J=8.47 Hz); 6.94 (s, 2H, CH aromatic). MS (m/z) 458.9; 459.9, 460.9.

Example 29

Preparation of Disodium 6-methoxy-2-methyl-3-(3,4,5-trimethoxybenzoyl)benzofuran-7-yl phosphate

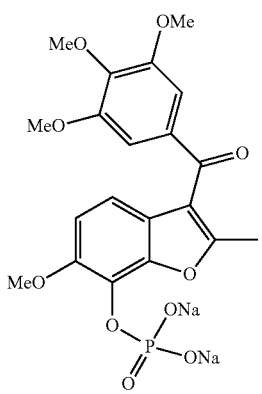

Step 1: Dibenzyl 6-methoxy-2-methyl-3-(3,4,5-trimethoxybenzoyl)benzofuran-7-yl phosphate To a mixture of 0.081 g (0.22 mmol) of (7-hydroxy-6-methoxy-2-methylbenzofuran-3-yl)(3,4,5-trimethoxyphenyl)methanone, 0.086 g (0.261 mmol) of carbon tetrabromide and 0.063 ml (0.283 mmol) of dibenzylphosphite in 2.5 ml of anhydrous acetonitrile 0.046 ml of anhydrous triethylamine was added dropwise at 0° C. under nitrogen atmosphere. The resulting mixture was stirred for 2 h at room temperature, then diluted to 20 ml with ethyl acetate, washed with water brine, dried over anhydrous magnesium sulfate, filtered off and evaporated to dryness under reduced pressure. The residue was purified by flash column chromatography (dichloromethane/ ethyl acetate, 9:1) to give the title compound as a colorless foam (0.13 g, 94%); $^1$H NMR (CDCl$_3$) δ 2.42 (s, 3H, Me-2); 3.83 (s, 1H, OMe); 3.93 (s, 3H, OMe); 5.33 (m, 4H, CH$_2$Ph); 6.89 (d, CH aromatic, J=8.7 Hz); 7.21 (dd, 1H, CH aromatic, J=8.72 Hz; J=1.2 Hz); 7.08 (s, 2H, CH aromatic); 7.29-7.43 (m, 10H, CH aromatic).

Step 2: Disodium 6-methoxy-2-methyl-3-(3,4,5-trimethoxybenzoyl)benzofuran-7-yl phosphate To a stirred solution of 0.122 g (0.193 mmol) of the product from Step 1 in 1 ml of anhydrous acetonitrile 0.075 ml (0.58 mmol) of bromotrimethylsilane was added at −5° C. under nitrogen atmosphere. The resulting mixture was stirred for 1 h at 0° C., then evaporated to dryness in vacuo. The residue was diluted to 5 ml with anhydrous methanol and pH of the solution was brought up about 10 by the addition of sodium methoxide. After evaporation of the resulting mixture under reduced pressure the solid residue was washed with anhydrous isopropanol (4×1.5 ml) and anhydrous ethanol (3×1.5 ml) and dried under vacuum to give 0.062 g (65% yield) of title compound as an colorless solid; $^1$H NMR (D$_2$O) δ 2.37 (s, 3H, Me-2); 3.76 (s, 6H, OMe); 3.79 (s, 3H, OMe); 3.82 (s, 3H, OMe); 4.66 (s, H$_2$O); 6.93 (d, 1H, CH aromatic, J=8.6 Hz); 7.04 (d, 1H, CH aromatic, J=8.6 Hz); 7.10 (s, 2H, CH aromatic).

Example 30

Preparation of (2-Hydroxy-6-methoxybenzofuran-3-yl)(3,4,5-trimethoxyphenyl)methanone

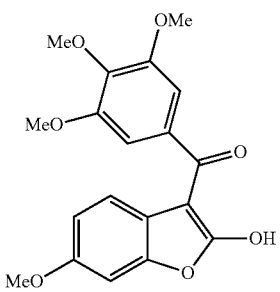 [SMILES: COc1ccc2c(C(=O)c3cc(OC)c(OC)c(OC)c3)c(O)oc2c1]

Step 1: 3-Oxo-3-(3,4,5-trimethoxyphenyl)propionic acid 10 ml of 2M solution of n-butyllithium in cyclohexane was added dropwise over 10 minutes to a stirred solution of 5.08 g (20 mmol) of bis(trimethylsilyl)malonate in 40 ml of anhydrous ether under nitrogen atmosphere at −60° C. The mixture was then allowed to warm to 0° C. and the solution of 2.3 g (10 mmol) of 3,4,5-trimethoxybenzoyl chloride in 20 ml of anhydrous ethyl ether was added in one portion. The resulting mixture was stirred for 10 min. at 0° C. then shaken with 100 ml of 5% aqueous sodium bicarbonate for 5 minutes. The aqueous phase was acidified to pH=~1 with cold 4N sulfuric acid and extracted with ethyl ether (3×100 ml). The combined extracts were dried over anhydrous magnesium sulfate, filtered off and evaporated to dryness to give the title compound as a creamy crystals (1.82 g, 71.6%); $^1$H NMR (CDCl$_3$) δ 3.8-3.92 (m, 9H, OMe); 4.03 (s, 1.8H, CH$_2$); 5.62 (s, 0.2H, CH enol); 7.2 (s, 2H, CH aromatic).

Step 2: 3-Methoxyphenyl 3-oxo-3-(3,4,5-trimethoxyphenyl)propanoate

To a mixture of 0.27 g (1.06 mmol) of the product of Step 1 and 0.13 g (1.06 mmol) of 3-methoxyphenol in 2 ml of anhydrous methylenechloride 0.16 ml (1.06 mmol) of diisopropylcarbondiimide was added at room temperature. The resulting mixture was stirred for 24 hours at room temperature and filtered off. The filtrate was evaporated to dryness and purified by flash column chromaytography (silica gel; methylene chloride) to give the title compound as a colorless crystals (0.185 g, 49%); $^1$H NMR (CDCl$_3$) δ 3.77 (s, 3H, OMe); 3.91 (s, 6H, OMe); 4.17 (s, 3H, OMe); 4.173 (s, 2H, CH₂); 6.6-6.8 (m, 3H, CH aromatic); 7.2-7.3 (m, 3H, CH aromatic).

Step 3: (2-Hydroxy-6-methoxybenzofuran-3-yl)(3,4,5-trimethoxyphenyl)methanone

The procedure of Baumm et al, Synthetic Communication 1987, 17(14), 1709-1716, was used. To a stirred solution of 0.0561 g (0.156 mmol) of the product of Step 2 and 0.041 g (0.171 mmol) of 4-acetamidobenzenesulfonyl azide in 2 ml of anhydrous acetonitrile 0.065 ml (0.47 mmol) of triethylamine was added at 0° C. After stirring for 3 hours at room temperature the solvent was evaporated to dryness under reduced pressure and the residue was purified by flash column chromatography (silica gel, methylene chloride) to give 0.059 g (98% yield) of 3-methoxyphenyl 2-diazo-3-oxo-3-(3,4,5-trimethoxyphenyl)propanoate. This was dissolved in 2 ml of anhydrous methylene chloride and 3.5 mg (7.9 µmol) of rhodium (III) acetate was added at room temperature under nitrogen atmosphere. The resulting mixture turned deep green after 1 h of stirring at room temperature. After filtration through Celite and washing with fresh methylene chloride, the filtrate was evaporated to dryness under reduced pressure to give the title compound as an deep yellow crystals (0.049 g, 91%); ¹H NMR (CDCl₃) δ 3.8 (s, 3H, OMe); 3.9 (s, 6H, OMe); 3.94 (s, 3H, OMe); 6.58 (dd, 1H, CH aromatic, J=2.4 Hz; 8.6 Hz); 6.76 (d, 1H CH aromatic; J=2.4 Hz); 7.04 (s, 2H, CH aromatic); 7.25 (d, 1H, CH aromatic, J=8.6 Hz).

Example 31

Preparation of 2-Butyl-3-(3,4,5-trimethoxyphenyl)-7-hydroxy-6-methoxy-benzo[b]furan

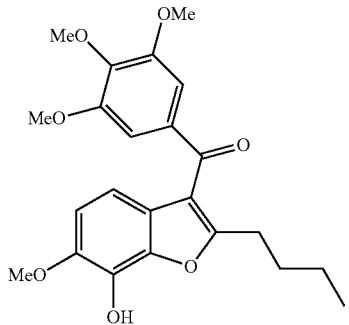 [SMILES: CCCCc1oc2c(O)c(OC)ccc2c1C(=O)c1cc(OC)c(OC)c(OC)c1]

This compound was prepared according to the procedure described for Example 12, except that butyllithium was used in place of methyllithium.

¹H NMR (300 MHz, CDCl₃) δ—7.10 (s, 2H, benzoyl Hs), 6.87 (d, J=8.61 Hz, 1H), 6.82 (d, J=8.58 Hz, 1H), 5.71 (s, 1H, OH), 3.94 (s, 3H, OMe), 3.93 (s, 3H, OMe), 3.82 (s, 6H, 2×OMe), 2.87 (t, 2H, J=7.54 Hz), 1.81-1.71 (m, 2H), 1.38-1.70 (m, 2H), 0.87 (t, 3H, J=7.37 Hz).

Example 32

Preparation of 2-Ethyl-3-(3,4,5-trimethoxyphenyl)-7-hydroxy-6-methoxy-benzo[b]furan

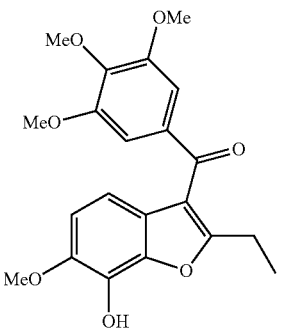 [SMILES: CCc1oc2c(O)c(OC)ccc2c1C(=O)c1cc(OC)c(OC)c(OC)c1]

This compound was prepared according to the procedure described for Example 12, except that ethyllithium was used in place of methyllithium.

¹H NMR (300 MHz, CDCl₃) δ—7.11 (s, 2H, benzoyl Hs), 6.91 (d, J=8.61 Hz, 1H), 6.83 (d, J=8.58 Hz, 1H), 3.93 (s, 3H, OMe), 3.92 (s, 3H, OMe), 3.82 (s, 6H, 2×OMe), 2.88 (q, 2H, J=15.00, 7.52 Hz), 1.33 (t, 3H, J=7.49 Hz).

Example 33

Preparation of 2-Bromomethyl-3-(3,4,5-tri-methoxybenzoyl)-6-methoxy-7-acetoxy-benzo[b]furan

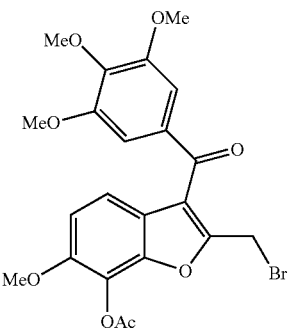 [SMILES: COc1cc(C(=O)c2c(CBr)oc3c(OC(C)=O)c(OC)ccc23)cc(OC)c1OC]

To a stirred solution of 2-methyl-3-(3,4,5-trimethoxybenzoyl)-6-methoxy-7-hydroxy-benzo[b]furan (Example 11) (985 mg, 2.65 mmol) in dry pyridine (10 mL) under nitrogen was added acetic anhydride (540 µL, 5.71 mmol) and after 0.5 hours more of acetic anhydride (540 µL, 5.71 mmol) was added and the solution was stirred for 1.5 hours. The solvent was distilled and the residue was taken in dichloromethane (20 mL), washed with 1M HCl. The organic layer was separated and dried over magnesium sulphate and solvent was distilled to gave the crude product which was purified over silica gel column to afford the title compound as a creamy solid (1.09 gm, 99%). ¹H NMR (300 MHz, CDCl₃) δ 7.28 (d, J=8.74 Hz, 1H), 7.09 (s, 2H, benzoyl Hs), 6.90 (d, J=8.69 Hz, 1H), 3.93 (s, 3H, OMe), 3.87 (s, 6H, 2×OMe), 3.84 (s, 3H, OMe), 2.51 (s, 3H), 2.43 (s, 3H). The 2-methyl-3-(3,4,5- trimethoxybenzoyl)-6-methoxy-7-O-acyl-benzo[b]furan (390 mg, 0.94 mmol, as obtained above) was dissolved in dry carbon tetrachloride (10 mL) and catalytic amount of benzoyl peroxide was added to it followed by the addition of N-bromosuccinamide (167 mg, 0.94 mmol). The mixture was stirred at reflux for 3 hours and the solvent was distilled under vacuum. The residue was dissolved in DCM (20 mL) and was washed with 10% sodium bicarbonate solution and water. The organic layer was separated, dried over magnesium sulphate and the solvent was distilled under vacuum to gave the title compound as creamy white solid (461 mg, 99%). $^1$H NMR (300 MHz, CDCl$_3$) δ 7.28 (d, J=8.76 Hz, 1H), 7.14 (s, 2H, benzoyl Hs), 6.95 (d, J=8.75 Hz, 1H), 4.6 (s, 2H), 3.94 (s, 3H, OMe), 3.89 (s, 3H, OMe), 3.86 (s, 6H, 2×OMe), 2.43 (s, 3H).

Example 34

Preparation of 2-Dimethylaminomethylene-3-(3,4,5-tri-methoxy-benzoyl)-6-methoxy-7-hydroxy-benzo[b]furan

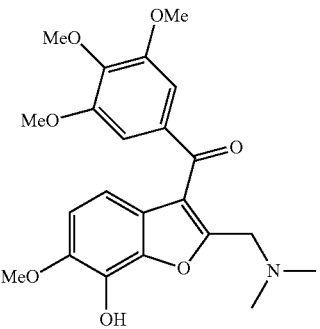 [SMILES: COc1cc(C(=O)c2c(CN(C)C)oc3c(O)c(OC)ccc23)cc(OC)c1OC]

To a stirred solution of 2-bromomethyl-3-(3,4,5-trimethoxybenzoyl)-6-methoxy-7-acetoxy-benzo[b]furan (Example 33) (25 mg, 0.051 mmol) in dry THF (0.5 mL) was added solution of dimethylamine (0.5 mL, excess, 2M solution in THF) and the mixture was stirred for 6 hours at room temperature (tlc). The solvent was distilled and the crude was purified over silica gel to afford the title compound as a light yellow solid (15 mg, 71%). $^1$H NMR (300 MHz, CDCl$_3$) δ—7.14 (s, 2H, benzoyl Hs), 6.85 (s, 2H, Ar—Hs), 3.93 (s, 3H, OMe), 3.92 (s, 3H, OMe), 3.81 (s, 6H, 2×OMe), 3.75 (s, 2H), 2.31 (s, 6H).

Example 35

Preparation of 2-(1H-Imidazol-1-yl)methyl-3-(3,4,5-trimethoxybenzoyl)-6-methoxy-7-hydroxy-benzo[b]furan

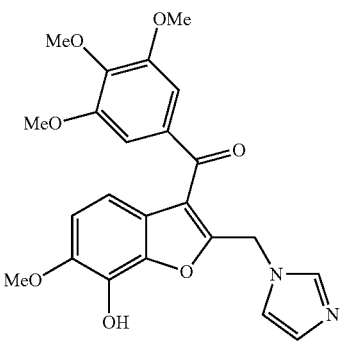 [SMILES: COc1cc(C(=O)c2c(Cn3ccnc3)oc3c(O)c(OC)ccc23)cc(OC)c1OC]

To a stirred suspension of 2-bromomethyl-3-(3,4,5-trimethoxy-benzoyl)-6-methoxy-7-acetoxy-benzo[b]furan (Example 33) (35 mg, 0.071 mmol) and potassium carbonate (20 mg, 0.15 mmol) in dry acetonitrile (1.5 mL) was added imidazole (19 mg, 0.28 mmol) and the reaction mixture was stirred for overnight (tlc). The solvent was distilled under vacuum and the crude was taken in ethyl acetate, filleted and purified over silica gel plate to afford the title compound as a light yellow solid (6 mg, 19%). $^1$H NMR (300 MHz, CDCl$_3$) δ—7.66 (s, 1H), 7.19 (s, 1H), 7.09 (s, 2H, benzoyl Hs), 7.07 (s, 1H), 6.85 (d, J=8.63 Hz, 1H), 6.74 (d, J=8.63 Hz, 1H), 5.37 (s, 2H), 4.00 (s, 3H, OMe), 3.95 (s, 3H, OMe), 3.79 (s, 6H, 2×OMe).

Example 36

Preparation of 2-(5-amino-2H-tetrazol-2-yl)-methyl-3-(3,4,5-tri-methoxy-benzoyl)-6-methoxy-7

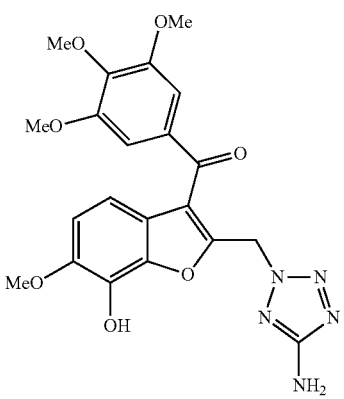 [SMILES: COc1cc(C(=O)c2c(Cn3nnc(N)n3)oc3c(O)c(OC)ccc23)cc(OC)c1OC]

When imidazole was replaced with aminotetrazole as in the above example the identical procedure afforded the title compound as a light yellow solid (2 mg, 9%). $^1$H NMR (300 MHz, CDCl$_3$) 7.20 (s, 2H, benzoyl Hs), 6.86 (d, J=8.71 Hz, 1H), 6.72 (d, J=8.48 Hz, 1H), 6.01 (s, 2H), 5.61 (s, 2H), 3.98 (s, 3H, OMe), 3.92 (s, 3H, OMe), 3.81 (s, 6H, 2×OMe).

Example 37

Preparation of 2-(4-Methylpiperazin-1-yl)methyl-3-(3,4,5-tri-methoxy-benzoyl)-6-methoxy-7-hydroxy-benzo[b]furan

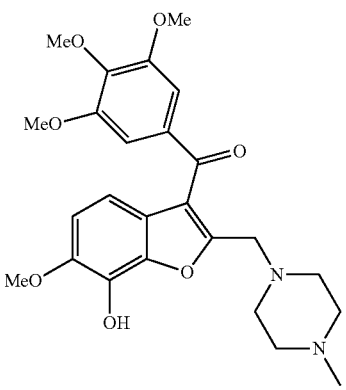 [SMILES: COc1cc(C(=O)c2c(CN3CCN(C)CC3)oc3c(O)c(OC)ccc23)cc(OC)c1OC]

To a stirred solution of 2-bromomethyl-3-(3,4,5-trimethoxybenzoyl)-6-methoxy-7-acetoxybenzo[b]furan (Example 33) (50 mg, 0.10 mmol) in dry THF (2 mL) at room temperature was added N-methylpiprazine (24 µL, 0.22 mmol) and the mixture was stirred for 2 hours and then added solution of dimethylamine (0.2 mL, 2M solution in THF, excess) and stirred for 4 hours. The solvent was distilled and the crude was purified over silica gel column and the product was crystallized from acetonitrile to afford the title compound as a light yellow crystalline solid (22 mg, 46%). $^1$H NMR (300 MHz, CDCl$_3$) δ 7.12 (s, 2H, benzoyl Hs), 6.89 (d, J=8.58 Hz, 1H), 6.85 (d, J=8.58 Hz, 1H), 3.93 (s, 6H, 2×OMe), 3.82 (s, 6H, 2×OMe), 2.57 (b, 4H), 2.39 (b, 4H), 2.23 (s, 3H, NMe).

Example 38

Preparation of 7-isopropoxy-6-Methoxy-2-methyl-3-(3,4,5-trimethoxybenzoyl)-1H-indole

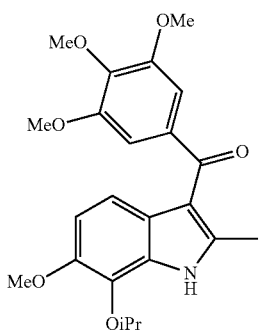

Step A: 2-isopropoxy-3-methoxyaniline

To a solution of 2-nitroguaiacol (Thompson, M. J.; Zeegerers, P. J. Tetrahedron, 1990, 46, 2661; 0.5062 g; 3 mmol) in anhydrous DMF (5 ml) K$_2$CO$_3$ (0.41 g; 3 mmol) was added and resulting mixture was stirred for 15 min under reduced pressure and saturated with N$_2$. To it, 2-bromopropane (1 ml; 10.6 mmol) was added and the reaction flask was sealed with septum and stirred overnight at 55° C. After evaporation of DMF under reduced pressure the residue was partitioned between diethyl ether (20 ml) and water (10 ml). The organic phase was washed with 2% aq. KOH (5 ml), brine, dried over anhydrous MgSO$_4$, filtered off and filtrate evaporated to dryness. The residue was dissolved in small volume of CH$_2$Cl$_2$ and filtered through short column with SiO$_2$, which was eluded with fresh CH$_2$Cl$_2$. The combined filtrates were evaporated to dryness under reduced pressure to give 2-isopropoxy-3-methoxynitrobenzene (0.62 g; 98% yield) as creamy syrup. $^1$H-NMR (CDCl$_3$) 1.26 (d, 6H, J=6.17 Hz); 3.87 (s, 3H); 4.61 (m, 1H, J=6.17 Hz); 7.06 (m, 2H); 7.26 (m, 1H). This was dissolved in ethanol (30 ml) and the resulting mixture was degassed under reduced pressure. To it 10% Pd on carbon (0.22 g) was added and the mixture was saturated with H$_2$ and stirred for 5 h under the balloon pressure of H$_2$. The catalyst was removed by filtration through Celite. The filtrate was evaporated to dryness to give the title compound (0.702 g; 92.5% yield) as colourless oil. $^1$H-NMR (CDCl$_3$) 1.28 (d, 6H, J=6.19 Hz); 3.7 broad s, 2H); 3.79 (s, 3H); 4.45 (m, 1H, J=6.19 Hz); 6.2-6.78 (m, 2H); 6.8 (m, 1H).

Step B: 6-iodo-2-isopropoxy-3-methoxy-N-trifluoroacetylaniline

To a suspension of CF$_3$CO$_2$Ag and the product of Step A (0.702 g; 3.88 mmol) in CH$_2$Cl$_2$ (30 ml) I$_2$ (0.99 g: 3.88 mmol) was added at 0° C. After stirring for 30 min at 0° C. the reaction mixture was filtered through Celite and filtrate washed with 5% aq Na$_2$S$_2$O$_5$ solution (2×15 ml), dried over anhydrous MgSO$_4$, filtered off and filtrate evaporated to dryness to give the crude 2-iodo-2-isopropoxy-3-methoxyaniline, which was used without further purification. This (0.84 g; 2.7 mmol) was dissolved in dry pyridine (5 ml) and to it trifluoroacetic anhydride (0.41 ml; 2.9 mmol) was added at room temperature. The resulting mixture was stirred for 2 h at room temperature and evaporated to dryness under reduced pressure. The residue was purified by flash column chromatography (SiO$_2$, hexane/ethyl acetate, 8:2) to give the title compound (0.675 g; 61% yield) as a colourless crystals. $^1$H-NMR (CDCl$_3$) 1.21 (d, 6H, J=6.16 Hz); 3.83 (s, 3H); 4.51 (m, 1H, J=6.16 Hz); 6.69 (d, 1H, J=8.86 Hz); 7.51 (d, 1H, d, 1H, J=8.86 Hz); 7.67 (broad s, 1H).

Step C: 2-isopropoxy-3-methoxy-6-(prop-1-ynyl)-N-trifluoroacetylaniline

A mixture of the product of Step B (0.275 g; 0.681 mmol), Cl$_2$Pd(PPh$_3$)$_2$ (0.058 g; 0.083 mmol); CuI (0.025 g; 0.13 µmol), anhydrous N,N-diisopropyl ethylamine (1 ml) in anhydrous DMF (5 ml) was cooled to −40° C., degassed under reduced pressure and saturated with dry N$_2$. To it, propyne gas (0.5 g; 12.4 mmol) was added at −40° C. The reaction flask was sealed with septum and allowed to warm up to room temperature and stirred overnight at room temperature than evaporated to dryness under reduced pressure. The residue was purified by flash column chromatography (SiO$_2$, hexane/ethyl acetate, 8:2) to give the title compound (0.171 g; 79% yield) as creamy solid. $^1$H-NMR (CDCl$_3$) 1.21 (d, 6H, J=6.16 Hz); 2.00 (s, 3H); 3.86 (s, 3H); 4.43 (m, 1H, J=6.16 Hz); 6.79 (d, 1H, J=8.67 Hz); 7.14 (d, 1H, J=8.67 Hz); 7.72 (broad s, 1H).

Step D: 7-isopropoxy-6-methoxy-2-methyl-3-(3,4,5-trimethoxybenzoyl)-1H-indole

A mixture of the product of Step C (0.171 g; 0.54 mmol), 3,4,5-trimethoxyphenyl iodide (0.191 g; 0.65 mmol), Cl$_2$Pd (PPh$_3$)$_2$ (0.044 g; 0.063 mmol); dry K$_2$CO$_3$ (0.23 g; 1.62 mmol in anhydrous DMF (5 ml) was degassed under reduced pressure and saturated with CO gas. The resulting mixture was vigorously stirred overnight at room temperature under CO balloon, then diluted to 50 ml with ethyl acetate and washed with water (3×15 ml), brine and dried over anhydrous MgSO$_4$, filtered off and filtrate evaporated to dryness. The residue was purified by flash column chromatography (SiO$_2$ CH$_2$Cl$_2$/ethyl acetate, 9:1) to give the title compound (0.143 g; 64% yield) as a yellow solid. $^1$H-NMR (CDCl$_3$) 1.27 (d, 6H, J=6.14 Hz); 2.51 (s, 3H); 3.79 (s, 6H); 3.85 (s, 3H); 3.90 (s, 3H); 4.69 (m, 1H, J=6.14 Hz); 6.76 (d, 1H, J=8.75 Hz); 7.04 (s, 2H); 7.11 (d, 1H, J=8.75 Hz); 8.83 (broad m, 1H).

Example 39

Preparation of 7-Hydroxy-6-methoxy-2-methyl-3-(3,4,5-trimethoxybenzoyl)-1H-indole

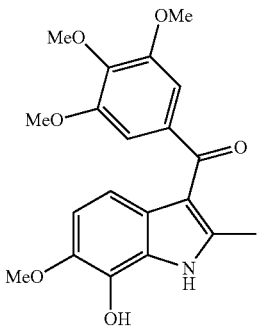 [SMILES: COc1cc(C(=O)c2c(C)[nH]c3c(O)c(OC)ccc23)cc(OC)c1OC]

To a solution of the product of Step D of above Example 38 (0.055 g; 0.133 mmol) in anhydrous $CH_2Cl_2$, $TiCl_4$ (0.04 ml; 0.36 mmol) was added at 0° C. The resulting mixture was stirred for 1 h and quenched by addition of $H_2O$ (3 ml). The two-phase mixture was diluted to 15 ml with $CH_2Cl_2$ and organic phase separated, dried over anhydrous $MgSO_4$, filtered off and filtrate evaporated to dryness. The residue was purified by flash column chromatography ($SiO_2$; $CH_2Cl_2$/ethyl acetate, 9:1) to give the title compound (0.0365 g; 74% yield) as a yellow solid. $^1$H-NMR ($CDCl_3$) 2.54 (s, 3H); 3.81 (s, 6H); 3.88 (s, 3H); 3.92 (s, 3H); 5.65 (s, 1H); 6.77 (d, 1H, J=8.71 Hz); 6.96 (d, 1H, J=8.71 Hz); 7.05 (s, 2H); 8.48 (s, 1H).

Example 40

Preparation of 3-(3,5-Dimethoxy-4-hydroxybenzoyl)-7-hydroxy-6-methoxy-2-methyl-1H-indole

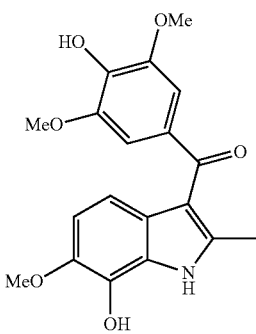 [SMILES: COc1cc(C(=O)c2c(C)[nH]c3c(O)c(OC)ccc23)cc(OC)c1O]

The title compound (0.003 g; 6.3% yield) was obtained as a by-product from the purification of Example 39, as a creamy solid. $^1$H-NMR ($CDCl_3$) 2.58 (s, 3H); 3.85 (s, 6H); 3.9 (s, 3H); 5.67 (s, 1H); 5.86 (s, 1H) 6.75 (d, 1H, J=8.7 Hz); 6.94 (d, 1H, J=8.71 Hz); 7.12 (s, 2H); 8.47 (s, 1H).

Example 41

Preparation of 6-Methoxy-2-methyl-3-(3,4,5-trimethoxybenzoyl)-7-tosyloxy-benzo[b]thiophene

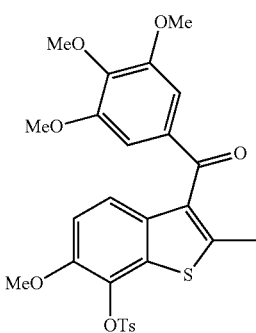

Step A: Benzyl 2-iodo-6-isopropoxy-5-methoxyphenyl sulfide

A mixture of the product of Step B, Example 37 (0.4 g; 1.16 mmol) in 20% solution of hydrazine in iPrOH (10 ml) was refluxed for 4 h under $N_2$ and evaporated to dryness under reduced pressure. The residue was diluted to 30 ml with diethyl ether, washed with $H_2O$ (2×5 ml), brine (10 ml), dried over anhydrous $MgSO_4$, filtered and filtrate evaporated to dryness under reduced pressure to give 2-amino-3-isopropoxy-4-methoxy-iodobenzene (0.256 g; 71%) which was used without further purification. This was stirred with the mixture of $H_2O$ (1.2 ml) and 48% $HBF_4$ (0.8 ml) for 15 min at room temperature. The resulting mixture was cooled to 0° C. and $NaNO_2$ (0.069 g; 1 mmol) in $H_2O$ (0.5 ml) was added to it drop wise at 0° C. during 10 min with stirring. This was allowed to warm up to room temperature and the precipitate filtered off, washed with $H_2O$ (1 ml), diethyl ether (1 ml) and dried in vacuo to give relevant diazonium intermediate (0.23 g; 69%). This was added portionwise to a solution of EtOC(S)SK (0.1 g; 0.62 mmol) in acetone (1.5 ml) at 0° C. during 10 min. After stirring for 30 min at 0° C., the stirring was continued for 45 min at room temperature and the mixture was evaporated to dryness under reduced pressure. The residue was diluted to 15 ml with diethyl ether, washed with $H_2O$ (10 ml), 2% KOH (2 ml), brine, dried over anhydrous $MgSO_4$, filtered and filtrate evaporated to dryness under reduced pressure. The residue was dissolved in MeOH (2 ml) and KOH (0.3 g; 5.3 mmol) was added. After stirring for 1 h at room temperature the mixture was evaporated to dryness under reduced pressure and the residue partitioned between $CH_2Cl_2$ (2 ml) and $H_2O$ (1 ml). Benzyl bromide (0.14 ml; 0.96 mmol) and n-$Bu_4NHSO_4$ (0.05 g;) was added to it, and the resulting mixture was vigorously stirred for 1 h, diluted to 15 ml with $CH_2Cl_2$. The organic phase was dried over anhydrous $MgSO_4$, filtered and filtrate evaporated to dryness under reduced pressure. The residue was purified by flash column chromatography ($SiO_2$; hexane/ethyl acetate 9.5:0.5) to give pure title compound (0.123 g; 52%) as colourless syrup. $^1$H-NMR ($CDCl_3$) 1.33 (d, 6H, J=6.18 Hz); 3.8 (s, 3H); 4.12 (s, 2H); 4.62 (m, 1H, J=6.18 Hz); 6.58 (d, 1H, J=8.71 Hz); 7.14-7.32 (m, 5H); 7.5 (d, 1H, J=8.71 Hz).

Step B: Benzyl 6-isopropoxy-5-methoxy-2-(prop-1-ynyl)phenyl sulfide

A mixture of the product of Step A (0.123 g; 0.296 mmol), $Cl_2Pd(PPh_3)_2$ (0.040 g; 0.057 mmol), CuI (0.014 g; 0.073 mmol) in anhydrous triethylamine (3 ml) was cooled to −40° C., degassed under reduced pressure and saturated with dry $N_2$. The propyne gas (0.45 g; 11.2 mmol) was added to it at −40° C. The reaction flask was sealed with septum and allowed to warm up to room temperature and stirred for 3 h at room temperature and diluted to 20 ml with diethyl ether and solid precipitated, filtered off. The filtrate was evaporated to dryness under reduced pressure and the residue, purified by flash column chromatography ($SiO_2$, hexane, hexane/ethyl acetate, 9:1) to give the title compound (0.065 g; 67% yield) as colourless syrup. $^1$H-NMR ($CDCl_3$) 1.26 (d, 6H, J=6.17 Hz); 2.09 (s, 3H); 3.79 (s, 3H); 4.2 (s, 2H); 4.44 (m, 1H, J=6.17 Hz); 6.73 (d, 1H, J=8.53 Hz); 7.12 (d, 1H, J=8.53 Hz); 7.15-7.4 (m, 5H).

Step C: 3-Iodo-7-isopropoxy-6-methoxy-2-methyl-benzo[b]thiophene

When the product of Step B was substituted for benzyl 5-methoxy-2-(prop-1-ynyl)phenyl sulfide in Step B of Comparator D, the identical process provided the title compound in 67% yield, as a heavy colourless syrup. $^1$H-NMR (CDCl$_3$) 1.32 (d, 6H, J=6.14 Hz); 2.53 (s, 3H); 3.9 (s, 3H); 4.69 (m, 1H, J=6.14 Hz); 7.07 (d, 1H, J=8.66 Hz); 7.28 (d, 1H, J=8.66 Hz).

Step D:
7-Isopropoxy-6-methoxy-2-methylbenzo[b]thiophene

When 3-iodo-7-isopropoxy-6-methoxy-2-methylbenzo[b]thiophene was substituted for 3-iodo-6-methoxy-2-methyl-benzo[b]thiophene in Step C of Comparator D, the identical process provided the title compound in 67% yield, as a heavy colourless syrup. $^1$H-NMR (CDCl$_3$) 1.33 (d, 6H, J=6.14 Hz); 2.51 (s, 3H); 3.88 (s, 3H); 4.69 (m, 1H, J=6.14 Hz); 6.84 (, 1H); 6.96 (d, 1H, J=8.51 Hz); 7.27 (d, 1H, J=8.51 Hz).

Step E:
6-methoxy-2-methyl-7-tosyloxy-benzo[b]thiophene

To a mixture of the product of Step D (0.033 g; 0.0941 mmol) in CH$_2$Cl$_2$ (1 ml) TiCl4 (0.02 ml; 0.182 mmol) was added at room temperature under N$_2$. After stirring for 10 min at room temperature, the mixture was diluted to 15 ml with CH$_2$Cl$_2$ and quenched with H$_2$O (5 ml) and the organic phase was dried over anhydrous MgSO$_4$, filtered and filtrate evaporated to dryness under reduced pressure to give 7-hydroxy-6-methoxy-2-methyl-benzo[b]thiophene (0.0256 g; 100%). This was diluted to 1 ml with CH$_2$Cl$_2$ and tosyl chloride (0.03 g; 0.158 mmol), followed by triethylamine 0.022 ml; 0.158 mmol) of were added to it. The resulting mixture was stirred for 1 h at room temperature, washed with H$_2$O, dried over anhydrous MgSO$_4$, filtered and filtrate evaporated to dryness under reduced pressure. The residue was purified by crystallization from hexane/ethyl acetate mixture (9.5:0.5) to give the title compound (0.035 g; 68%), as creamy crystals. $^1$H-NMR (CDCl$_3$) 2.45 (s, 3H); 2.48 (s, 3H); 3.63 (s, 3H); 6.83 (s, 1H); 7.32 (d, 2H, J=8.27 Hz); 7.43 (d, 1H, J=8.62 Hz); 7.87 (d, 2H, J=8.62 Hz).

Step F: 6-Methoxy-2-methyl-3-(3,4,5-trimethoxy-benzoyl)-7-tosyloxy-benzo[b]thiophene When 6-methoxy-2-methyl-7-tosyloxy-benzo[b]thiophene was substituted for 6-methoxy-2-methylbenzo[b]thiophene in Step D of Comparator C, the identical process provided the title compound in 68% yield, as a heavy colourless syrup. $^1$H-NMR (CDCl$_3$) 2.42 (s, 3H); 2.46 (s, 3H); 3.61 (s, 3H); 3.82 (s, 6H); 3.93 (s, 3H): 6.91 (d, 1H, J=8.87 Hz); 7.09 (s, 2H); 7.34 (d, 2H, J=8.19 Hz), 7.43 (d, 1H, J=8.87 Hz); 7.88 (d, 2H, J=8.19 Hz).

Example 42

Preparation of 7-Hydroxy-6-methoxy-2-methyl-3-(3,4,5-trimethoxybenzoyl)benzo[b]thiophene

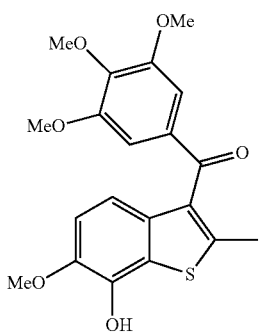

A mixture of the product of Example 41 (0.035 g; 0.00645 mmol) in THF (0.5 ml) and 1% NaOH in MeOH (0.52 ml; 0.0129 mmol) was stirred overnight at 30° C. under N$_2$ and acidified with the drop of CF$_3$CO$_2$H. This was evaporated to dryness and diluted to 15 ml with diethyl ether, washed with 0.1 M HCl (2 ml), 5% NaHCO$_3$ (2 ml), brine, dried over anhydrous MgSO$_4$, filtered and filtrate evaporated to dryness under reduced pressure. The residue was purified by flash column chromatography (SiO$_2$, CH$_2$Cl$_2$) to give pure title compound (0.007 g; 28%), as a colourless crystals. $^1$H-NMR (CDCl$_3$) 2.47 (s, 3H); 3.83 (s, 6H); 3.92 (s, 6H); 5.94 (s, 1H); 6.93 (d, 1H, J=8.69 Hz); 7.05 (d, 1H, J=8.69 Hz); 7.1 (s, 2H).

Example 43

Preparation of 2-[(N-Methyl-2-amino-aceticacid methyl ester)-methenyl)-3-(3,4,5-trimethoxybenzoyl)-6-methoxy-7-hydroxy-benzo[b]furan

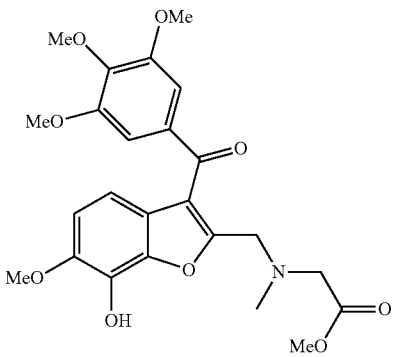 [SMILES: COC(=O)CN(C)Cc1oc2c(O)c(OC)ccc2c1C(=O)c1cc(OC)c(OC)c(OC)c1]

A mixture of 2-bromomethyl-3-(3,4,5-trimethoxybenzoyl)-6-methoxy-7-acetoxy-benzo[b]furan Example 33 (185 mg, 0.38 mmol) and sarcosine-methyl-ester-hydrochloride (156 mg, 1.11 mmol) in a mixture of dry DMF: DIEA (3 mL: 0.5 mL) was stirred at room temperature for overnight (tlc). The solvent was distilled and the crude residue was dissolved in THF (1 mL) and dimethylamine (0.5 mL, excess) was added to it and stirred for 2 hours at room temperature. The solvent was distilled and the crude product was purified over silica gel column to gave the product as a light yellow paste (132 mg, 75%). $^1$H NMR (300 MHz, CDCl$_3$) δ—7.13 (s, 2H, benzoyl Hs), 6.85 (s, 2H, Ar—Hs), 4.02 (s, 2H), 3.93 (s, 6H, 2×OMe), 3.81 (s, 6H, 2×OMe), 3.64 (s, 3H, OMe), 3.88 (s, 2H), 2.45 (s, 3H, NMe).

Example 44

Preparation of 2-[(N-Methyl-2-amino-aceticacid)-methenyl)-3-(3,4,5-trimethoxybenzoyl)-6-methoxy-7-hydroxy-benzo[b]furan

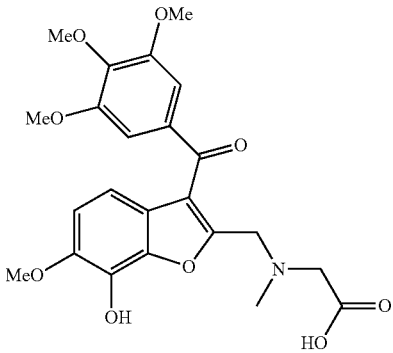 [SMILES: COc1cc(C(=O)c2c(CN(C)CC(=O)O)oc3c(O)c(OC)ccc23)cc(OC)c1OC]

The ester Example 43 above (120 mg, 0.25 mmol) was dissolved in THF:water (3 mL; 2:1), solution of LiOH (12 mg, 0.5 mmol in 0.25 mL of water) was added to it and the mixture was stirred for 3 hours at room temperature. The solvent was distilled to 1 mL and diluted with dichloromethane (10 mL). Tri-fluoro acetic acid (40 µL, 0.52 mmol) was added when the compound went into dichloromethane making the solution yellow colored. The organic layer was separated, dried over magnesium sulphate and solvent was distilled to gave the product as light yellow solid which was crystallized from hexane/DCM to gave the dirty colored solid (66 mg, 57%). $^1$H NMR (300 MHz, CDCl$_3$) δ—7.10 (s, 2H, benzoyl Hs), 7.07 (d, J=8.62 Hz, 1H), 6.63 (d, J=8.58 Hz, 1H), 4.69 (s, 2H), 4.00 (s, 2H), 3.92 (s, 3H, OMe), 3.82 (s, 3H, OMe), 3.76 (s, 6H, 2×OMe), 2.96 (s, 3H, NMe).

Example 45

Preparation of 2-N-(Aminoethanesulphonamide)-3-(3,4,5-trimethoxybenzoyl)-6-methoxy-7-hydroxy-benzo[b]furan

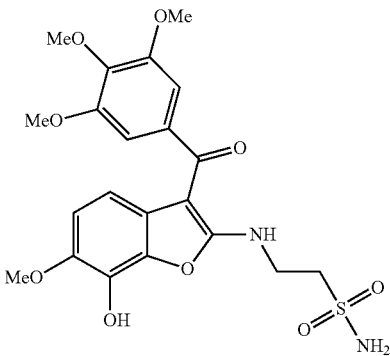 [SMILES: COc1cc(C(=O)c2c(NCCS(N)(=O)=O)oc3c(O)c(OC)ccc23)cc(OC)c1OC]

When benzyl-amine was substituted with aminoethane sulphonamide. HCl as in Example 19 step 1 the identical procedure afforded the title compound as a yellow solid (25 mg, 25%) along with 2-amino-3-(3,4,5-tri-methoxy-benzoyl)-6-methoxy-7-hydroxy-benzo[b]furan (Example 1927 mg, 35%). $^1$H NMR (300 MHz, CDCl$_3$) δ—9.21 (bs, 1H, NH), 6.94 (s, 2H, benzoyl Hs), 6.62 (d, J=8.61 Hz, 1H), 6.51 (d, J=8.47 Hz, 1H), 5.1 (b, 2H), 4.15 (q, 2H, J=12.32, 6.38 Hz), 3.91 (s, 3H, OMe), 3.86 (s, 3H, OMe), 3.83 (s, 6H, 2×OMe), 3.54 (t, 2H, J=6.18 Hz).

Example 46

Preparation of 3-(4-Hydroxy-3,5-di-methoxy-benzoyl)-7-hydroxy-6-methoxy-2-Methyl-benzo[b]furan

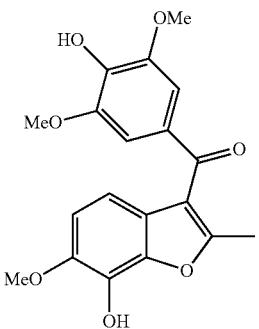

2-Methyl-3-(3,4,5-trimethoxybenzoyl)-7-hydroxy-6-methoxy-benzo[b]furan Example 11 (100 mg, 0.27 mmol) was dissolved in dry dichloromethane (5 mL) and solid aluminium trichloride (72 mg, 0.54 mmol) was added to it. The mixture was stirred for 2 hours when additional amount of aluminium trichloride (72 mg, 0.54 mmol) was added and the stirring was continued for 2 more hours (tlc). The reaction was quenched with saturated solution of ammonium chloride and diluted with DCM (20 mL) the organic layer was separated and washed with water, dried over magnesium sulphate and solvent was distilled to gave the crude product which was purified over silica gel column. The compound was crystallized from methanol to gave the product as white solid. (42 mg, 44%). $^1$H NMR (300 MHz, CDCl$_3$) δ 7.16 (s, 2H, benzoyl Hs), 6.91 (d, J=8.58 Hz, 1H), 6.83 (d, J=8.58 Hz, 1H), 5.94 (s, 1H, OH), 5.68 (s, 1H, OH), 3.91 (s, 3H, OMe), 3.87 (s, 6H, 2×OMe), 2.54 (s, 3H, Me).

Example 47

Further Alternative Method for the Preparation of 2-Methyl-3-(3,4,5-trimethoxybenzoyl)-6-methoxy-7-hydroxy-benzo[b]furan by Multi-component Coupling Step 1: 2-Methyl-3-(3,4,5-trimethoxybenzoyl)-6-methoxy-7-isopropoxy-benzo[b]furan To a stirred solution of 2-isopropoxy-3-methoxy-6-iodophenol (308 mg, 1.00 mmol) in dry tetrahydrofuran (2 mL) was added dropwise a solution of 1-propynyl magnesium bromide (5, 6 mL, 3 mmol, 0.5 M solution in THF) at 0° C. under nitrogen. Dichloro-bis-triphenylphosphine palladium catalyst (40 mg, 0.06 mmol) was added and the reaction mixture was heated to 70° C. for 3 hours (tlc). The solvent was removed under vacuum and the residue was dried under vacuum. Dry dimethylsulfoxide (8 mL) was added and the nitrogen atmosphere was replaced with carbon monoxide. 3,4,5-Trimethoxyiodobenzene 6 (310 mg 1.05 mmol) was added and the reaction mixture was stirred at 90° C. for 17 hours and then quenched with saturated ammonium chloride solution and extracted with ethyl acetate (2×25 mL). The organic layer was washed with water and dried over magnesium sulphate. The crude product was purified by flash chromatography (silica gel, eluent=hexane/diethyl ether; 8:2-7:3) to afford the title compound as a creamy white solid. The product was crystallized from methanol. Yield—290 mg, 70%; $^1$H NMR (300 MHz, CDCl$_3$) δ—7.10 (s, 2H, benzoyl Hs), 7.07 (d, 1H), 6.85 (d, 1H, J=8.57), 4.74-4.68 (m, 1H), 3.93 (s, 3H, OMe), 3.87 (s, 3H, OMe), 3.83 (s, 6H, 2×OMe), 2.52 (s, 3H, Me), 1.37 (d, 6H, J=6.18 Hz).

Step 2: 2-Methyl-3-(3,4,5-trimethoxybenzoyl)-6-methoxy-7-hydroxy-benzo[b]furan

To a stirred solution of 2-methyl-3-(3,4,5-trimethoxybenzoyl)-6-methoxy-7-isopropoxy-benzo[b]furan (30 mg, 0.073 mmol) at 0° C. in dry dichloromethane (1 mL) was added boron trichloride solution (1M solution in DCM, 73 µL, 0.073 mmol) and reaction mixture was warmed to room temperature and the stirring was continued for 2 hours (tlc). The reaction mixture was quenched with saturated ammonium chloride solution and diluted with dichloromethane (5 mL). the organic layer was separated and dried over magnesium sulphate. The solvent was distilled to gave the crude product as off white colored crystalline solid which was re-crystallized from methanol to gave the product as white crystalline material. Yield—25 mg, 93% (Note 1). $^1$H NMR (300 MHz, CDCl$_3$) δ—7.09 (s, 2H, benzoyl Hs), 6.93 (d, 1H, J=8.54 Hz), 6.83 (d, 1H, J=8.56 Hz), 5.70 (bs, 1H, OH), 3.93 (s, 3H, OMe), 3.92 (s, 3H, OMe), 3.83 (s, 6H, 2×OMe), 2.54 (s, 3H, 2-Me).

Note: A similar reaction when scaled-up with 2-methyl-3-(3,4,5-trimethoxybenzoyl)-6-methoxy-7-isopropoxy-benzo[b]furan (1.25 gm) and boron trichloride solution (1M solution in DCM, 3.1 mL) gave the title compound (930 mg, 83%).

Example 48

Further Alternative Method for the Preparation of 2-Methyl-3-(3,4,5-trimethoxybenzoyl)-6-methoxy-7-hydroxy-benzo[b]furan by Friedel-Crafts Acylation

Step 1: 2-Methyl-7-hydroxy-6-methoxy-benzo[b]furan

The solution of 3-iodo-6-methoxy-1,2-phenylene diacetate [(prepared by the iodination of diacetylglucinol with $I_2$ and $CF_3CO_2Ag$ (1 gm, 2.86 mmol) $^1H$ NMR (300 MHz, $CDCl_3$) δ—7.59 (d, 1H, J=8.88 Hz), 6.66 (d, 1H, J=8.94 Hz), 3.81 (s, 3H, OMe), 2.34 (s, 3H), 2.27 (s, 3H)] in a mixture of DMF/diisopropylethylamine (12 mL: 1.5 mL) was degassed with nitrogen gas and the solution was cooled to −40° C. Propyne gas (app wt. 3 gm, excess) was passed through this stirred solution over a period of 30 minutes. To this mixture was added $Pd(PPh_3)_2Cl_2$ (120 mg) followed by the addition of the copper (I) iodide (40 mg) and the mixture was allowed to come to room temperature and stirred for additional 40 hours (tlc). To this solution was added di-methyl-amine (4 mL, 1M solution in THF) and the mixture was stirred for another 18 hours at room temperature. The solvent was distilled in vacuum and the residue was taken in ethyl-acetate (50 mL). The organic layer was washed with water, dried over magnesium sulphate and the solvent was distilled to give the crude compound which was characterized as such by NMR. $^1H$ NMR (300 MHz, $CDCl_3$: $D_2O$ exchange) δ—6.82 (d, 1H, J=8.58 Hz), 6.39 (d, 1H, J=8.60 Hz), 3.85 (s, 3H, OMe), 2.08 (s, 3H, Me).

The above crude product was dissolved in dry THF (6 mL) and TBAF (1 mL, 1M solution in THF) was added to it and the mixture was stirred with refluxing for 8 hours. Solvent was distilled in vacuum and the residue was dissolved in DCM (20 mL) and washed with 1M HCl solution. The organic layer was separated, dried over magnesium sulphate and the crude was purified over silica gel column (eluent=Hexane: di-ethyl-ether; 100:0 to 60:40) to give the pure product (17) as light cream paste (390 mg, 77%). $^1H$ NMR (300 MHz, $CDCl_3$: $D_2O$ exchange) δ—6.89 (d, 1H, J=8.37 Hz), 6.39 (d, 1H, J=8.38 Hz), 6.26 (s, 1H, 3H), 5.61 (bs, 1H, OH), 3.91 (s, 3H, OMe), 2.42 (s, 3H, Me).

Step 2: 2-Methyl-6-methoxy-7-(4-toluoylsulphonate)-benzo[b]furan

2-Methyl-7-hydroxy-6-methoxy-benzo[b]furan, from Step 1 above, (180 mg, 1 mmol) was dissolved in dry pyridine (2 mL) and p-toulene-sulphonyl-chloride (228 mg, 1.2 mmol) and the mixture was stirred at 80° C. for 6 hours. Solvent was distilled and the crude was taken in ethyl-acetate (15 mL) and washed with water. The organic layer was dried over the magnesium sulphate and solvent was distilled to gave the crude which was purified over silica gel column (eluent=Hexane:ethyl-acetate:dieth-ylether; 80:0:20 to 70:10:20) to gave the compound (3, 128 mg, 39%+starting material) as light yellow paste solidify on standing at room temperature. $^1H$ NMR (300 MHz, $CDCl_3$: $D_2O$ exchange) δ—7.84 (d, 2H, J=7.71 Hz), 7.29 (d, 2H, J=8.05 Hz), 7.21 (d, 1H, J=8.49 Hz), 6.78 (d, 1H, J=8.47 Hz), 6.22 (s, 1H, 3H), 3.69 (s, 3H, OMe), 2.42 (s, 3H, Me), 2.25 (s, 3H, Me).

Step 3: 2-Methyl-3(3,4,5-trimethoxybenzoyl)-6-methoxy-7-(4-methyl-benzene-sulphonate)-benzo[b]furan 2-Methyl-6-methoxy-7-(4-methylbenzenesulphonate)-benzo[b]furan, from Step 2 above (65 mg, 0.2 mmol) was dissolved in dry dichloromethane (2 mL) and 3,4,5-trimethoxy-benzoyl-chloride (55 mg, 0.24 mmol) followed by the addition of tin(II) chloride (28 µL, 0.24 mmol) and the mixture was stirred at reflux for 8 hours, more acid chloride (20 mg) and reaction was continued for another 6 hours (tlc). Reaction was diluted with dichloromethane (15 mL) and organic layer was washed with sodium bicarbonate solution. The organic layer was separated, dried over the magnesium sulphate and solvent was distilled to gave the crude which was purified over silica gel column (eluent=Hexane:diethyl ether; 80:0 to 70:30) to gave the product (70 mg, 68%) as light yellow solid. $^1H$ NMR (300 MHz, $CDCl_3$: $D_2O$ exchange) δ 7.86 (d, 2H, J=8.31 Hz), 7.34-7.22 (overlapping doublets, 3H), 7.06 (s, 2H, benzoyl H), 6.83 (d, 1H, J=8.73 Hz), 3.93 (s, 3H, OMe), 3.84 (s, 6H, 2×OMe), 3.68 (s, 3H, OMe), 2.46 (s, 3H, Me), 2.39 (s, 3H, Me).

Note: The same reaction was run by using 240 mg of starting benzofuran, acid chloride 254 mg, tin (IV) chloride 101 uL. (Yield=297 mg, 78%).

Step 4: 2-Methyl-3-(3,4,5-trimethoxybenzoyl)-6-methoxy-7-hydroxy-benzo[b]furan (Example 11)

2-Methyl-3-(3,4,5-trimethoxybenzoyl)-6-methoxy-7-(4-methyl-benzene-sulphonate)-benzo[b]furan, from Step 3 above, was dissolved in a mixture of solvent (THF/MeOH; 4 mL: 10 mL) and sodium hydroxide (32 mg) was added to it and the mixture was stirred with refluxing for 6 hours. The solvent was distilled and the crude was taken in dichloromethane (20 mL) and washed with water (20 mL×2). The organic layer was separated and dried over magnesium sulphate and the solvent was distilled. The crude product was purified over silica gel column to give the product (150 mg, 76%).

Example 49

Alternative Method for the Preparation of Example 29 using $POCl_3$

To a solution of freshly distilled $POCl_3$ (0.125 ml; 1.34 mmol) in anhydrous $CH_2Cl_2$ (1 ml) a mixture of Example 11 (0.2 g; 0.54 mmol) and triethylamine (0.12 ml; 0.86 mmol) in anhydrous $CH_2Cl_2$ (1 ml) was added dropwise at −5 to 0° C. under $N_2$ with stirring. After stirring for 10 minutes at 0° C., the mixture was evaporated to dryness under reduced pressure. The residue was suspended in anhydrous toluene (2 ml), stirred for 5 minutes at room temperature and evaporated to dryness under reduced pressure. The residue was kept in vacuo for 30 minutes and then resuspended in acetonitrile (2 ml). This was added at once to 0.5 M aqueous NaOH (5 ml). The resulting mixture was evaporated to dryness under reduced pressure and the residue was suspended in water (2 ml). After adjusting the pH of the solution to ~10 with 0.5 M NaOH, the resulting solution was filtered through Whatman glass microfibre filter to remove any traces of solid material. The filtrate was concentrated to about 0.5 ml and acidified to pH ~1 with concentrated HCl. To facilitate the removal of water and the excess of HCl the mixture was repeatedly diluted to 5 ml with acetonitrile and evaporated to dryness (×3), followed by dilution with $CH_2Cl_2$ and evaporation. The residue formed, was kept in vacuo for 30 minutes and suspended in methanol/$CH_2Cl_2$ mixture (5:95; 10 ml) (NOTE 2)

and insoluble NaCl was filtered off. The filtrate was evaporated to dryness and the crystalline residue was washed with hexane/CH$_2$Cl$_2$ mixture (1:1; 10 ml) and dried to give free acid as a slightly creamy solid (0.209 g; 87%). $^1$HNMR (CDCl$_3$/CD$_3$OD 1:1) 2.5 (s, 3H); 3.29 (m, CD$_3$OD); 3.81 (s, 6H); 3.87 (s, 3H); 3.88 (s, 3H); 4.6 (s, HDO); 6.91 (d, 1H, J=8.7 Hz); 7.08 (s, 2H); 7.12 (d, 1H, J=8.7 Hz); 7.55 (s, CDCl$_3$); LC, retention time=1.19 min (+99%); MS 452.8 (MH$_2$+1). The free acid was suspended in methanol (2 ml) and the pH of the resulting suspension was adjusted to ~10 by addition of 0.5 M NaOH. During this process the mixture gradually become homogenous. This was concentrated to about 1 ml and the product was precipitated by the addition of acetonitrile (10 ml). The solid was washed with fresh acetonitrile, anhydrous ethyl ether and dried in vacuo until constant mass to give 0.215 g of pure title compound (94% yield) as a creamy solid. $^1$HNMR (D$_2$O), 7.02 (d, 6.91 (d, 1H, J=8.68 Hz), 4.66 (HDO), 3.8 (s, 3H), 3.79 (s, 3H), 3.75 (s, 6H), 2.36 (s, 3H). LC, retention time=1.19 (+99%). MS 452.8 (MH$_2$-2Na+1). Anal. Calculated for C$_{20}$H$_{19}$Na$_2$O$_{10}$P×0.5 H$_2$O: Na 9.10%; P 6.13%; Found Na 9.09%; P 9.26%.

Example 50

Comparator F

Preparation of 6-Methoxy-2-methyl-3-(3,4,5-trimethoxybenzoyl)-1H-indole

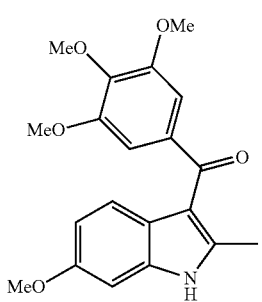 [SMILES: COc1ccc2c(C(=O)c3cc(OC)c(OC)c(OC)c3)c(C)[nH]c2c1]

A mixture of 2-iodo-5-methoxy-N-trifloroacetylaniline (Flynn et al, J. Med. Chem., 2002, 45(12), 2670; 0.508 g; 1.5 mmol), Cl$_2$Pd(PPh$_3$)$_2$ (0.102 g; 0.145 mmol); CuI (0.016 g; 0.085 mmol), anhydrous N,N-diisopropyl ethylamine (1 ml) in anhydrous DMF (10 ml) was cooled to −40° C., degassed under reduced pressure and saturated with dry N$_2$. The propyne gas (0.53 g; 13.3 mmol) was added to it at −40° C. The reaction flask was sealed with septum and allowed to warm up to room temperature and stirred for 3 h. After removal of excess of propyne under reduced pressure 3,4,5-trimethoxyphenyl iodide (0.5 g; 1.7 mmol) was added to it, followed by dry K$_2$CO$_3$ (0.621 g; 4.5 mmol). The resulting mixture was degassed in vacuo and saturated with CO gas and stirred for 3 h under CO balloon pressure. The mixture was diluted to 50 ml with diethyl ether, washed with H$_2$O (2×15 ml), brine (10 ml), dried over anhydrous MgSO$_4$, filtered and filtrate evaporated to dryness under reduced pressure. The residue was purified by flash column chromatography (SiO$_2$; CH$_2$Cl$_2$) to give pure title compound (0.295 g; 55%) as a yellow crystals:

$^1$H-NMR (CDCl$_3$) 2.52 (s, 3H,); 3.8 (m, 9H); 3.91 (s, 3H); 6.73 (dd, 1H, J=2.22, 8.75 Hz); 6.79 (d, 1H, J=2.22 Hz); 7.06 (s, 2H); 7.35 (d, 1H, J=8.75 Hz); 8.6 (broad s, 1H, NH).

Example 51

Comparator G

Preparation of 6-Methoxy-2-methyl-3-(3,4,5-trimethoxybenzoyl)benzo[b]thiophene

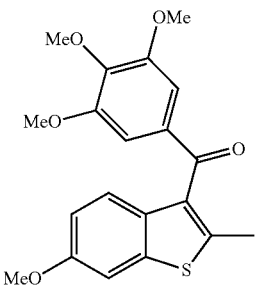 [SMILES: COc1ccc2c(C(=O)c3cc(OC)c(OC)c(OC)c3)c(C)sc2c1]

Step A: Benzyl 5-methoxy-2-(prop-1-ynyl)phenyl sulfide

When benzyl 2-iodo-5-methoxyphenyl sulfide (Flynn et al, Org. Lett. 2001, 3(5), 651) was substituted for 6-iodo-2-isopropoxy-3-methoxy-N-trifluoroacetylaniline in Step C of Example 38 and reaction time was extended to 72 h, the similar process provided the title compound in 69% yield as a creamy solid. $^1$H-NMR (CDCl$_3$) 2.1 (s, 2H); 3.7 (s, 3H); 4.17 (s, 2H); 6.61 (dd, 1H, J=2.53, 8.5 Hz); 6.72 (d, 1H, J=2.53 Hz); 7.2-7.33 (m, 5H); 7.38 (d, 1H, J=8.5 Hz).

Step B: 3-Iodo-6-methoxy-2-methylbenzo[b]thiophene

To a solution of the product of Step A (0.156 g; 0.58 mmol) in CH$_2$Cl$_2$ 1 ml) I$_2$ (0.147 g: 0.58 mmol) was added and the mixture was stirred for 1 h at room temperature, then washed with 5% aq Na$_2$S$_2$O$_5$ solution (2×5 ml), dried over anhydrous MgSO$_4$, filtered off and filtrate evaporated to dryness to give the crude 2-iodo-2-isopropoxy-3-methoxyaniline, which was purified by flash column chromatography (SiO$_2$, hexane, hexane/ethyl acetate 9.5:0.5) to give the title compound (0.0863 g; 47%) as colourless syrup. $^1$H-NMR (CDCl$_3$) 2.58 (s, 3H); 3.85 (s, 3H); 6.99 (dd, 1H, J=2.33, 8.8 Hz); 7.19 (d, 1H, J=2.33 Hz); 7.51 (d, 1H, J=8.8 Hz).

Step C: 6-Methoxy-2-methylbenzo[b]thiophene t-BuLi (1.7 M in pentane; 0.32 ml; 0.54 mmol) was added to a solution of the 3-iodo-6-methoxy-2-methylbenzo[b]thiophene (0.0863 g; 0.27 mmol) in anhydrous THF (2.5 ml) at −78° C. under N$_2$. The mixture was allowed to warm up to 0° C. and quenched by the addition of saturated NH$_4$Cl (1 ml). This was diluted to 15 ml with diethyl ether and washed with 5% NaHCO$_3$ (10 ml), dried over anhydrous MgSO$_4$, filtered off and filtrate evaporated to dryness. The residue was purified by flash column chromatography (SiO$_2$, hexane, hexane/ethyl acetate 9.5:0.5) to give the title compound (0.024 g; 50% yield) as colourless solid. $^1$H-NMR (CDCl$_3$) 2.53 (s, 3H); 3.84 (s, 3H); 6.86 (s, 1H); 6.92 (dd, 1H, J=2.24, 8.87 Hz); 7.222 (d, 1H, J=2.24 Hz); 7.51 (d, 1H, J=8.67 Hz).

Step D: 6-Methoxy-2-methyl-3-(3,4,5-trimethoxybenzoyl)benzo[b]thiophene

To a mixture of 6-methoxy-2-methylbenzo[b]thiophene (0.024 g; 0.132 mmol) and 3,4,5-trimethoxybenzoyl chloride (0.052 g; 0.225 mmol) in 1,2-dichloroethane (1 ml) SnCl₄ (0.023 ml) was added. The resulting mixture was stirred for 1 h at 40° C., quenched with H₂O (1 ml), diluted to 15 ml with diethyl ether, washed with 5% NaHCO₃ (5 ml), brine (10 ml), dried over anhydrous MgSO₄, filtered and filtrate evaporated to dryness under reduced pressure. The residue was purified by flash column chromatography (SiO₂; hexane/ethyl acetate 9:1) to give pure title compound (0.020 g; 41%) as a colourless crystals. ¹H-NMR (CDCl₃) 2.47 (s, 3H); 3.8 (s, 6H); 3.84 (s, 3H); 3.93 (s, 3H); 6.90 (dd, 1H, J=2.4, 8.89 Hz); 7.1 (s, 2H); 7.24 (d, 1H, J=2.4 Hz); 7.42 (d, 1H, J=8.89 Hz).

Example 52

Preparation of 3-(3,5-Dimethoxybenzoyl)-7-hydroxy-6-methoxybenzo[b]furan

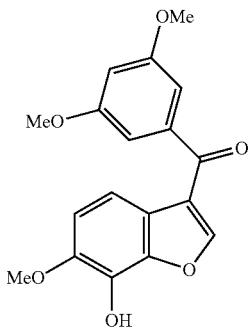 [SMILES: COc1cc(OC)cc(C(=O)c2coc3c(O)c(OC)ccc23)c1]

Step 1: 2-t-Butyldimethylsilanyl-3-(3,5-dimethoxybenzoyl)-6-methoxy-7-isopropoxy-benzo[b]furan When 3,4,5-trimethoxyiodobenzene was replaced by 3,5-di-methoxyiodobenzene as in Example 4 (step 3) the identical procedure afforded the title compound as a light yellow paste (102 mg, 49%). ¹H NMR (300 MHz, CDCl₃) δ 7.00 (d, J=2.32 Hz, 2H), 6.81 (d, J=8.30 Hz, 1H), 6.71 (d, J=8.61 Hz, 1H), 6.67 (t, J=2.31 Hz, 1H), 4.74 (m, 1H), 3.86 (s, 3H, OMe), 3.78 (s, 6H, 2×OMe), 1.38 (d, 6H, J=6.16 Hz), 1.01 (s, 9H), 0.27 (s, 6H).

Step 2: 3-(3,5-Dimethoxybenzoyl)-6-methoxy-7-isopropoxy-benzo[b]furan

The procedure same as in Example 6 (Step 1) afforded the title compound (57 mg, 83%). ¹H NMR (300 MHz, CDCl₃) δ 8.02 (s, 1H, C₂H), 7.82 (d, 1H, J=8.59 Hz), 7.04 (d, J=8.63 Hz, 1H), 6.99 (d, J=2.31 Hz, 2H), 6.67 (t, J=2.30 Hz, 1H), 4.71 (m, 1H), 3.91 (s, 3H, OMe), 3.83 (s, 6H, 2×OMe), 1.36 (d, 6H, J=6.15 Hz).

Step 3: 3-(3,5-Dimethoxybenzoyl)-7-hydroxy-6-methoxybenzo[b]furan

The procedure same as in Example 6 (Step 2) afforded the title compound as a creamy crystalline solid (21 mg, 49%). ¹H NMR (300 MHz, CDCl₃) δ 8.05 (s, 1H, C₂H), 7.69 (d, J=8.56 Hz, 1H), 7.02 (d, J=8.59 Hz, 1H), 6.99 (d, J=2.03 Hz, 2H), 6.67 (broad t, 1H), 5.70 (broad s, 1H, OH), 3.97 (s, 3H, OMe), 3.83 (s, 6H, 2×OMe); ¹³C NMR (75 MHz, CDCl₃) δ 189.48 (CO), 160.50, 152.09, 144.56, 143.32, 140.79, 130.84, 120.87, 120.48, 112.53, 109.22, 106.27, 104.28, 56.84, 55.25.

Example 53

Preparation of 3-(Pentafluorobenzoyl)-6-methoxy-7-hydroxybenzo[b]furan

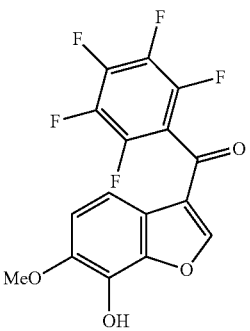 [SMILES: COc1ccc2c(C(=O)c3c(F)c(F)c(F)c(F)c3F)coc2c1O]

Step 1: 2-t-Butyldimethylsilanyl-3-(pentafluorobenzoyl)-7-isopropoxy-6-methoxybenzo[b]furan When 3,4,5-trimethoxyiodobenzene was replaced by pentafluoroiodobenzene as in Example 4 (step 3) the identical procedure was used for nucleophilic addition, however, the oxidation step was different and was as follow [180 mg of the crude material obtained was co-distilled with toluene and dissolved in dry dichloromethane (5 mL) and pyridine-dichromate (266 mg, 0.71 mmol) was added to in portions and the reaction mixture was stirred for overnight (tlc). The solution was diluted with dichloromethane, solvent was decanted and washed with water. The organic layer was separated, dried over magnesium sulphate and the solvent was distilled to give the crude product, which was purified over silica gel column to afford the title compound as a light yellow paste (156 mg, 35%)] ¹H NMR (300 MHz, CDCl₃) δ 6.82 (d, J=8.67 Hz, 1H), 6.31 (d, J=8.64 Hz, 1H), 4.71 (m, 1H), 3.86 (s, 3H, OMe), 1.37 (d, 6H, J=6.15 Hz), 1.03 (s, 9H), 0.42 (s, 6H).

Step 2: 3-(Pentafluorobenzoyl)-6-methoxy-7-isopropoxy-benzo[b]furan

The procedure same as in Example 6 (Step 1) afforded the title compound as a light yellow paste (31 mg, 83%). ¹H NMR (300 MHz, CDCl₃) δ 7.89 (s, 1H, C₂H), 7.83 (d, J=8.58 Hz, 1H), 7.07 (d, J=8.61 Hz, 1H), 4.69 (m, 1H), 3.93 (s, 3H, OMe), 1.35 (d, 6H, J=6.16 Hz).

Step 3: 3-(Pentafluorobenzoyl)-6-methoxy-7-hydroxybenzo[b]furan

The procedure same as in Example 6 (step 2) afforded the title compound as a creamy crystalline solid (21 mg, 63%). ¹H NMR (300 MHz, CDCl₃) δ 7.93 (s, 1H, C₂H), 7.70 (d, J=8.55 Hz, 1H), 7.05 (d, J=8.56 Hz, 1H), 5.73 (bs, 1H, OH), 3.98 (s, 3H, OMe).

What is claimed:
1. A compound that is
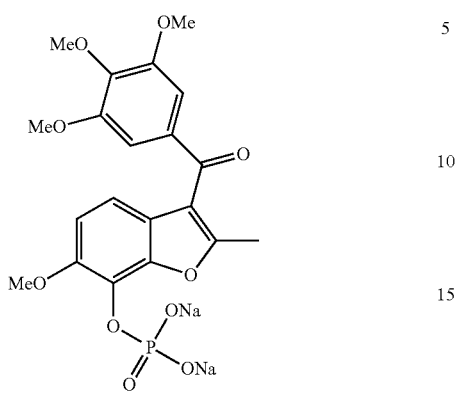
disodium 6-methoxy-2-methyl-3-(3,4,5-trimethoxybenzoyl)-benzofuran-7-yl phosphate.
2. A composition comprising a compound according to claim 1 and a pharmaceutically acceptable carrier, diluent, or excipient.
* * * * *